United States Patent [19]
Nakanishi et al.

[11] Patent Number: 6,001,824
[45] Date of Patent: Dec. 14, 1999

[54] BUTYRYL-TYROSINYL SPERMINE, ANALOGS THEREOF AND METHODS OF PREPARING AND USING SAME

[75] Inventors: Koji Nakanishi; Danwen Huang, both of New York, N.Y.; Seok-Ki Choi, Cambridge, Mass.; Aristotle Kalivretenos, Columbia, Md.; Robert Goodnow, Upper Montclair, N.J.

[73] Assignee: The Trustees of Columbia University, New York, N.Y.

[21] Appl. No.: 08/376,924

[22] Filed: Jan. 23, 1995

Related U.S. Application Data

[63] Continuation-in-part of application No. 08/275,336, Jul. 14, 1994, Pat. No. 5,770,625, which is a continuation of application No. 07/701,223, May 16, 1991, abandoned, which is a continuation-in-part of application No. 07/153,151, Feb. 8, 1988, abandoned.

[51] Int. Cl.$^6$ ........................ A61K 31/655; C07C 247/16
[52] U.S. Cl. ........................ 514/151; 514/415; 514/419; 548/469; 548/503; 552/8
[58] Field of Search ........................ 552/1, 8; 435/184; 564/153, 157; 514/616, 151, 415, 419; 260/404.5; 548/469, 503

[56] References Cited

U.S. PATENT DOCUMENTS

| | | | |
|---|---|---|---|
| 3,888,898 | 6/1975 | Koppe et al. | 558/420 |
| 5,218,000 | 6/1993 | Usherwood et al. | 514/617 |

FOREIGN PATENT DOCUMENTS 0156540  10/1985  European Pat. Off. .

OTHER PUBLICATIONS

Anis, N., et al., "Structure–Activity Relationships of Philanthotoxin Analogs and Polyamines on N–Methyl–D–Aspartate and Nicotininc Acetylcholine Receptors," *J. Pharmacol. Exp. Ther.*, 254, 764–772 (1990); U.S.A.

Eldefrawi, A., et al., "Structure and sythesis of a potent glutamate receptor antagonist in wasp venom," *Proc. Natl. Acad. Sci. USA*, 85, 4910–4913, 1988.

Goodnow, R., et al., "Sythesis of Glutamate Receptor Antagonist Philanthotoxin–433 (PhTX–433) and Its Analogs," *Tetrahedron*, 46, 3267–3286 (1990); Great Britain.

Kalivretenos, A.G., and Nakanishi, K., *J. Org. Chem.*, 58, 6596–6608 (1993); U.S.A.

Kitts, K.S., and Piek, T., "Action of the Polyamine B–Philanthotoxin an Neuromuscular Transmission in Insects," *Neuropharmacology*, 25, 1089–1093 (1986); Great Britain.

Nakanishi, K., et al., "Philanthotoxin —433 (PhTX–433), a non–competitive glutamate receptor inhibitor," *Pure & Appl. Chem.*, 62, 1223–1230 (1990); Great Britain.

Piek, T., et al., "Neuromuscular Block in Honeybees by the Venom of the Bee Wolf Wasp (*Philanthus triangulum* F.)," *Toxicon*, 13, 199–201 (1975); Great Britain.

Van Wilgenburg, H., et al., "Ion Channel Block in Rat Diaphragm by the Venom of the Digger Wasp *Philanthus triangulum*," *Comp. Biochem. Physiol.*, 79C, 205–211 (1984); Great Britain.

*Primary Examiner*—Shailendra Kumar
*Attorney, Agent, or Firm*—John P. White; Cooper & Dunham LLP

[57] ABSTRACT

The present invention provides a compound having the structure:

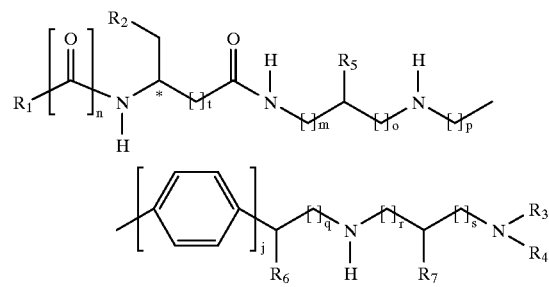

wherein $R_1$ is a saturated or unsaturated linear or branched chain alkyl group, or a cholestanyl group; wherein $R_2$ is a 2-indolyl, 3-indolyl, 4-indolyl, 5-indolyl, 4-hydroxyphenyl, 4-(arylalkyloxy)phenyl, 3,4-dihalophenyl, 4-hydroxy-3,5-dihalophenyl, 4-azidophenyl or 4-halophenyl group; wherein $R_3$ is H, a linear or branched chain alkyl or alkenyl group, or a phenyl, 2-azidophenyl, 3-azidophenyl, 4-azidophenyl group, or an a alkenylacyl, 3-amino-3-butylpropyl, N-[N-(N-{4-azidobenzoyl}aminopropyl)aminopropyl], cis- or trans-cinnamyl, 2-amino-2-[(4'-azidophenyl)acetyl, (trifluoromethyl)aminoacetyl or D- or L-arginyl group bonded through the α-carbonyl moiety thereof; $R_4$ is H, or a linear or branched chain alkyl group; wherein $R_5$, $R_6$ and $R_7$ are independently the same or different and are H, a linear or branched chain alkyl group, an aryl group or an arylalkyl group; wherein n, j and t are each 0 or 1; wherein m, o, p, q, r and s are independently the same or different and are 0, 1 or 2; wherein r+s and m+o are each equal to 2; wherein, if j is 0, p+q is 2; wherein, if j is 1, then p is 1, q is 0 and $R_6$ is H; and wherein * denotes a D or L configuration. The invention also provides a method of synthesizing the compound. Another aspect of the invention concerns a method of treating a subject afflicted by a disorder associated with binding of an etiological agent to a glutamate receptor.

9 Claims, 12 Drawing Sheets

FIGURE 3A
1 PhTX-433 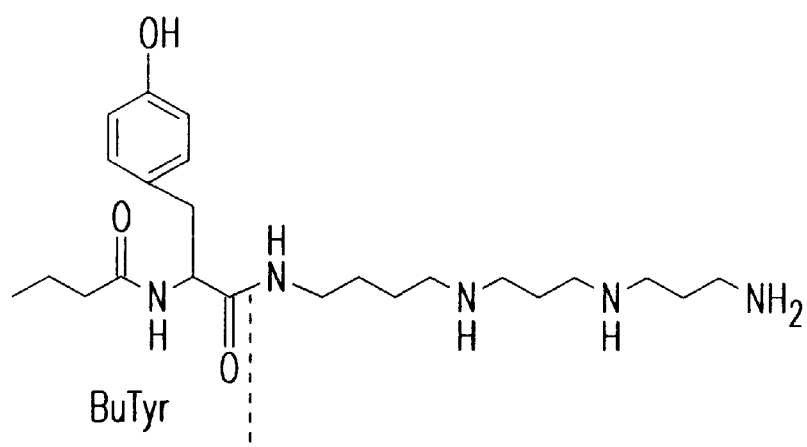
2 PhTX-334 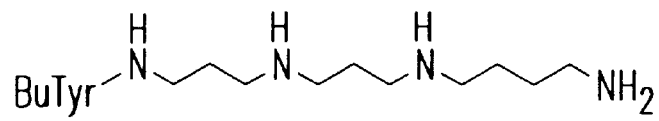
3 PhTX-343 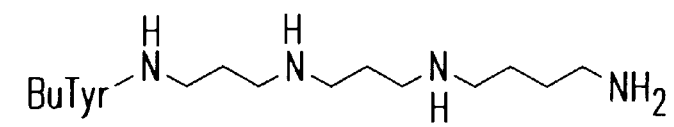

reagents: a. CH₂=CHCN; b. (Boc)₂O; c. LiAlH₄;
d. CbzCl/Et₃N; e. TFA reagents: a. TFA; b. BuCl/Et₃N

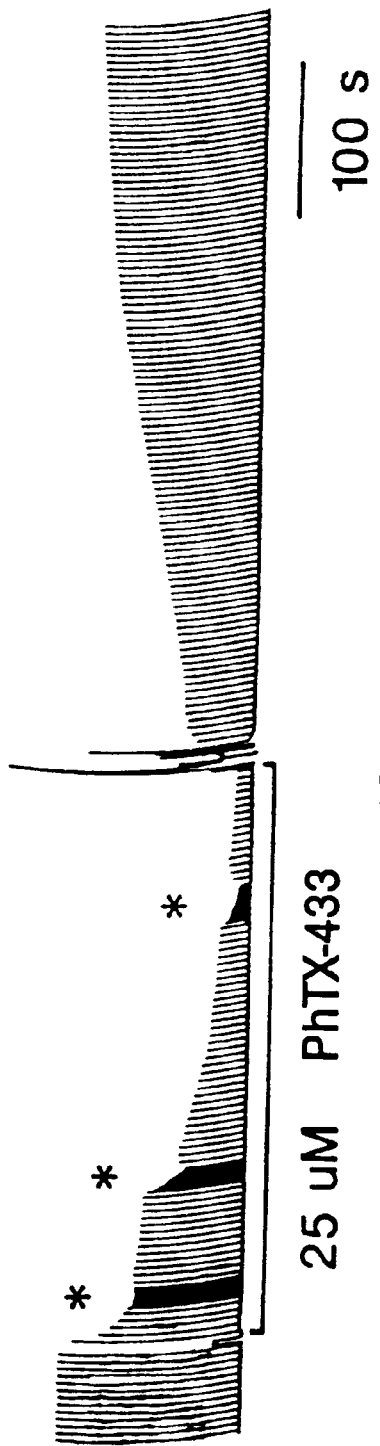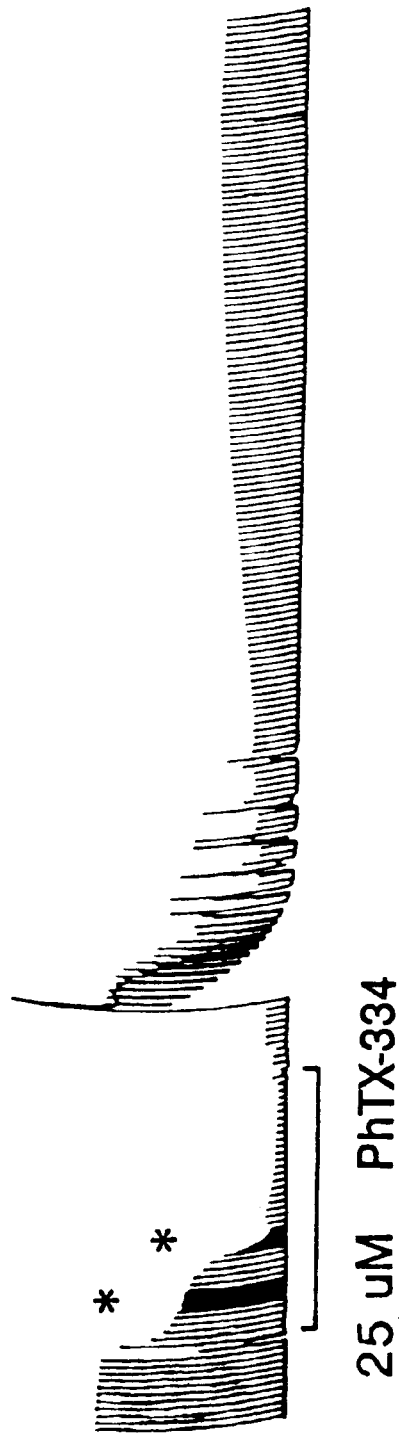

Method A

FIGURE 7B
Method B
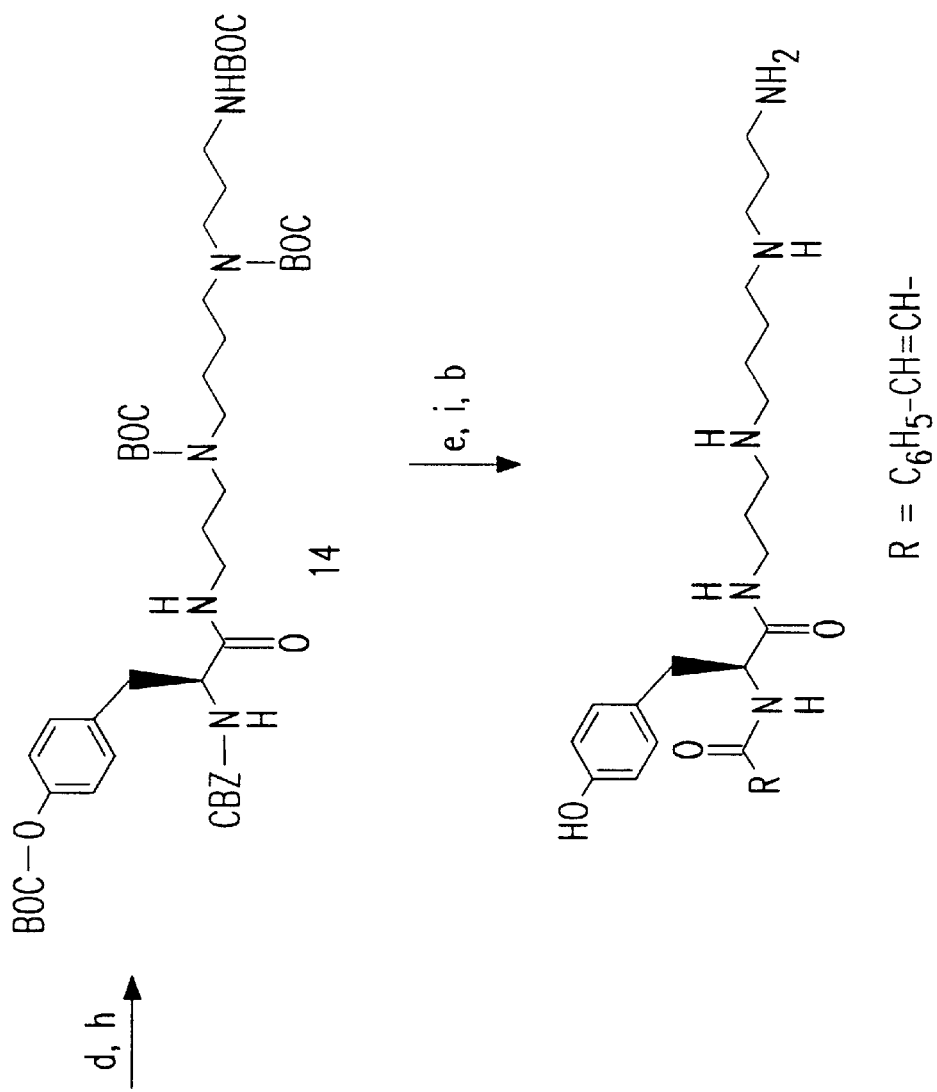
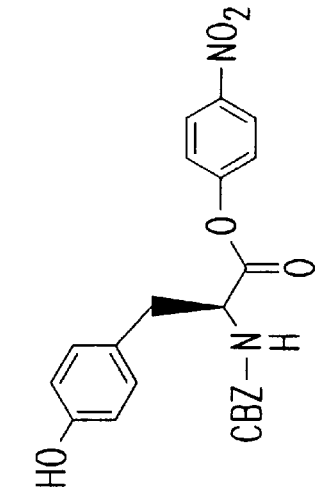

(a) halogens: $I_2 > Br_2 > Cl_2 > F$; modifications to hydroxyl give variable activities (b) S configuration is better than R (c) polyamine chain essential (d) longer chain with $N^+$ increases activity (e) hydrophobicity and/or aromaticity increases activity but long aliphatic chains lead to insolubility; site for (photo)affinity labels (f) n-butyl here increases activity

BUTYRYL-TYROSINYL SPERMINE, ANALOGS THEREOF AND METHODS OF PREPARING AND USING SAME

This application is a continuation-in-part of U.S. Ser. No. 08/275,336, filed Jul. 14, 1994, now U.S. Pat. No. 5,770,625, which is a continuation of U.S. Ser. No. 07/701,223, filed May 16, 1991, now abandoned, which is a continuation-in-part of the U.S. Ser. No. 07/153,151, filed Feb. 8, 1988, now abandoned, the contents of which are hereby incorporated by reference into the present application.

The invention described herein was made in the course of work under Grant No. INT-8610138 from the National Science Foundation, and Grant Nos. AI 10187, ES 02594, and E504977 from the National Institute of Health, U.S. Department of Health and Human Services. Accordingly, the U.S. Government has certain rights in the invention.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed in this application.

Glutamate receptors are believed to be the principal excitatory neurotransmitter receptors in the central nervous system (CNS). Based on the chemicals that activate glutamate receptors, such receptors are generally divided into three major subtypes: quisqualate (QUIS-R), N-methyl-D-aspartate (NMDA-R), and kainate (KAIN-R). These receptors are involved in development, learning and neuropathology and likely mediate the neurodegenerative consequences of hypoxemia, epilepsy, Alzheimer's disease, and Huntington's disease (1–5). There is considerable interest in developing agents that block glutamate receptors, particularly antagonists of the NMDA type receptor because of their anticonvulsant action and possible protection from ischemic brain damage (7). NMDA receptors are involved in a variety of neurological and psychiatric disorders, and antagonists of this receptor may be therapeutically valuable in movement disorders, such as epilepsy, and in various acute and chronic neurodegenerative disorders.

Studies of glutamate receptors, in particular studies employing biochemical techniques, have been made difficult by the relative paucity of potent antagonists for these receptor proteins. Selective, competitive and non-competitive antagonists of the NMDA receptor have become available during the past few years, but the search for antagonists of the L-quisqualate-sensitive receptor has only recently shown signs of success (8–10). Quisqualate-sensitive glutamate receptors are distributed widely in excitable tissues of multicellular animals (11) and studies of the effects of the venoms of certain wasps and spiders on vertebrate and invertebrate neurons and muscle fibers suggest that one source of antagonists for this class of receptor might be the venoms of some species of predaceous arthropods (12–17).

The solitary digger wasp *Philanthus triangulum F.*, which is a sphecid wasp that preys on honey bees, manufactures a venom which blocks glutamate receptors on locust skeletal muscle (16,17). Piek and colleagues have shown that the venom of this wasp contains a component (termed δ-philanthotoxin) which exhibits a number of pharmacological properties including open channel block of junctional glutamate receptors (18) and extrajunctional glutamate D-receptors (19) of locust leg muscle, most of which are quisqualate-sensitive (20). However, Piek and colleagues did not isolate or determine the active compound of the venom component.

In order to deduct the active ingredient contained in venom from the wasp *Philanthus triangulum F.*, a series of extractions were performed to isolate an active fraction. Based on a structure deduced from chemical analysis of the fraction, a series of related compounds were synthesized and their activities and chemical properties compared to those of the venom extract fraction. This resulted in the unexpected discovery of the active compound of the venom. The present invention concerns the active ingredient contained in venom from the wasp *Philanthus triangulum F.*, the chemical structure of this active ingredient, a method for synthesizing the ingredient, designated philanthotoxin-433 PhTX-433, and the use of PhTX-433 as a potent inhibitor of the glutamate receptors. In addition, the present invention involves the synthesis of pharmacologically active analogs of this ingredient, e.g., PhTX-334, PhTX-343 and many others (wherein the numerals denote the number of methylenes between the amino groups of the spermine moiety).

SUMMARY OF THE INVENTION

The present invention provides a compound having the structure:

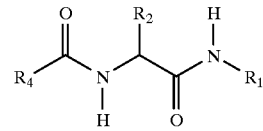

wherein $R_1$ is hydrogen or a branched or unbranched, substituted or unsubstituted aminoalkyl having from two to twenty atoms in the chain; $R_2$ is hydrogen, methyl, a branched or unbranched, substituted or unsubstituted alkyl having from two to twenty atoms in the chain or $CH_2R_3$; $R_3$ is a substituted or unsubstituted aryl; and $R_4$ is methyl, a branched or unbranched, substituted or unsubstituted alkyl, alkenyl, alkynyl, alkenynyl, or cycloalkyl having from two to twenty atoms in the chain, or a substituted or unsubstituted aryl group.

The subject invention further provides a compound having the structure:

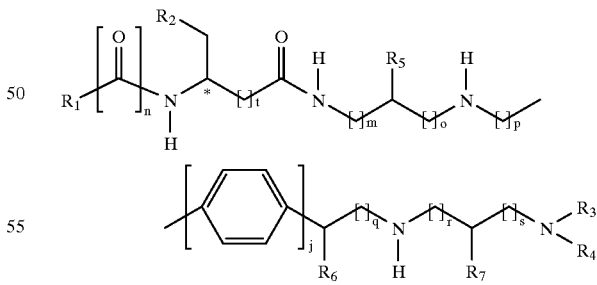

wherein $R_1$ is a saturated or unsaturated linear or branched chain alkyl group, or a cholestanyl group; wherein $R_2$ is a 2-indolyl, 3-indolyl, 4-indolyl, 5-indolyl, 4-hydroxyphenyl, 4-(arylalkyloxy)phenyl, 3,4-dihalophenyl, 4-hydroxy-3,5-dihalophenyl, 4-azidophenyl or 4-halophenyl group; wherein $R_3$ is H, a linear or branched chain alkyl or alkenyl group, or a phenyl, 2-azidophenyl, 3-azidophenyl, 4-azidophenyl group, or an a alkenylacyl, 3-amino-3-butylpropyl, N-[N-(N-{4-azidobenzoyl}aminopropyl)

aminopropyl], cis- or trans-cinnamyl, 2-amino-2-[4'-azidophenyl)acetyl, (trifluoromethyl)amino-acetyl or D- or L-arginyl group bonded through the α-carbonyl moiety thereof; $R_4$ is H, or a linear or branched chain alkyl group; wherein $R_5$, $R_6$ and $R_7$ are independently the same or different and are H, a linear or branched chain alkyl group, an aryl group or an arylalkyl group; wherein n, j and t are each 0 or 1; wherein m, o, p, q, r and s are independently the same or different and are 0, 1 or 2; wherein r+s and m+o are each equal to 2; wherein, if j is 0, p+q is 2; wherein, if j is 1, then q is 0 and $R_6$ is H; and wherein * denotes a D or L configuration.

The invention also concerns a method of preparing the compound which comprises treating venom, venom sacs or venom glands or the wasp *Philanthus triangulum F.* to produce an aqueous extract, and recovering the compound from the resulting aqueous extract. Additionally, the invention provides a method of preparing the compound which comprises contacting a branched- or unbranched- chain alkylamine having from two to twenty atoms in the chain and having hydrogen or a protection group attached to each nitrogen atom of the chain with a compound having the structure:

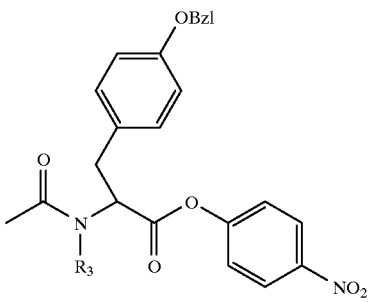

wherein $R_3$ and $R_4$ are the same or different and is hydrogen or a lower alkyl group so as to form a product, treating the product to produce the compound and recovering the compound.

Another aspect of the invention concerns a method of treating a subject afflicted by a disorder associated with binding of an etiological agent to a glutamate receptor which comprises administering to the subject an amount of the compound effective to inhibit binding of the etiological agent to the receptor. The invention also concerns a method of treating a subject afflicted by a stroke-related disorder associated with excessive binding of glutamate to glutamate receptors which comprises administering to the subject an amount of the compound effective to inhibit the excessive binding of the glutamate to the receptors. Lastly, the invention provides an insecticidal composition which comprises an effective amount of the compound and a suitable carrier and a method of combatting insects which comprises administering to the insects an amount of the insecticidal composition effective to produce paralysis in the insects.

Brief Description of Figures

FIG. 4. Effects of PhTX-433 (A) and PhTX-334 (B) on the neurally-evoked twitch contraction of locust metathoracic retractor urguis muscle. (A) and (B) are data from different nerve-muscle preparations dissected from the same adult, female locust (*Schistocerca gregaria*). The nerve-muscle preparations were superfused with standard locust saline (23) for 30 min before the toxins were applied. The retractor unguis nerve was stimulated with single, brief (0.1 s), supramaximal stimuli applied at a constant, low frequency, before and after toxin application (in locust saline), but during the period of toxin application the stimulation frequency was sometimes reversed temporarily.

DETAILED DESCRIPTION OF THE INVENTION

Figure 1:
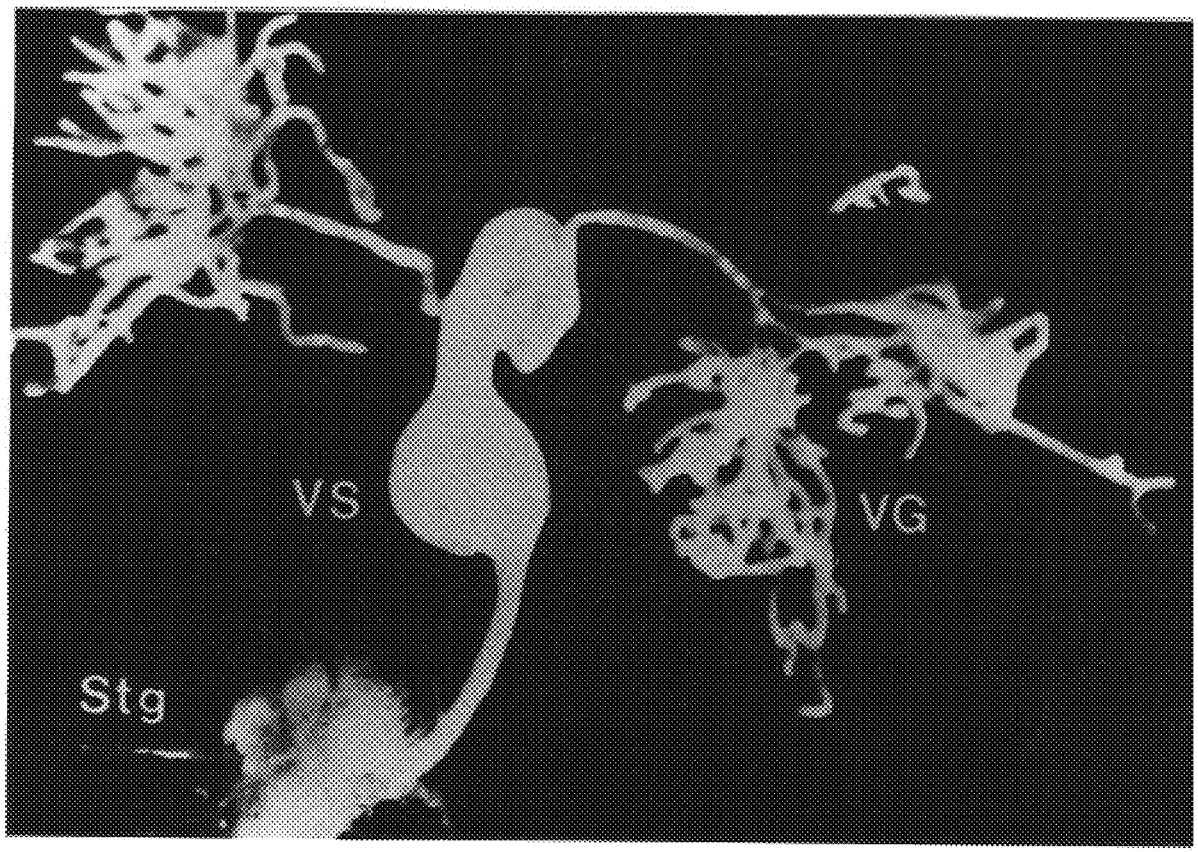
FIG. 1. Venom sac (VS), gland (VG) and the sting apparatus (Stg) dissected from *Philanthus triangulum.*

The present invention provides a compound having the structure.

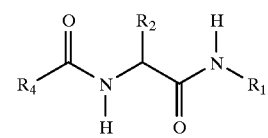

wherein $R_1$ is hydrogen or a branched or unbranched, substituted or unsubstituted aminoalkyl having from two to twenty atoms in the chain; $R_2$ is hydrogen, methyl, a branched or unbranched, substituted or unsubstituted alkyl having from two to twenty atoms in the chain or CH$_2$R$_3$; R$_3$ is a substituted or unsubstituted aryl; and R$_4$ is methyl, a branched or unbranched, substituted or unsubstituted alkyl, alkenyl, alkynyl, alkenynyl, or cycloalkyl having from two to twenty atoms in the chain, or a substituted or unsubstituted aryl group.

Examples of R$_1$ include but are not intended to be limited to hydrogen,
—CH$_2$(CH$_2$)$_2$NH(CH$_2$)$_4$NH(CH$_2$)$_3$NH$_2$,
—CH$_2$(CH$_2$)$_3$NH(CH$_2$)$_3$NH(CH$_2$)$_3$NH$_2$,
—CH$_2$(CH$_2$)$_2$NH(CH$_2$)$_3$NH(CH$_2$)$_4$NH$_2$,
—CH$_2$(CH$_2$)$_3$NH(CH$_2$)$_3$NH$_2$,
—CH$_2$(CH$_2$)$_3$NH$_2$,
—CH$_2$(CH$_2$)$_3$NHCH$_2$CH (CH$_3$) CH$_2$NH(CH$_2$)$_3$NH$_2$,
—CH$_2$(CH$_2$)$_3$NHCH$_2$CH (C$_4$H$_9$) CH$_2$NH(CH$_2$)$_3$NH$_2$,
—CH$_2$(CH$_2$)$_3$N$^+$(CH$_3$)$_2$(CH$_2$)$_4$N$^+$(CH$_3$)$_2$(CH$_2$)$_3$N$^+$(CH$_3$)$_3$,
—CH$_2$(CH$_2$)$_2$NH(CH$_2$)$_4$NH(CH$_2$)$_3$NHCOCH$_3$,
—CH$_2$(CH$_2$)$_2$NH(CH$_2$)$_4$NH(CH$_2$)$_3$NHCOCH$_2$NH$_2$,
—CH$_2$(CH$_2$)$_2$NH(CH$_2$)$_4$NH(CH$_2$)$_3$NHCO (CH$_2$)$_3$NH$_2$,
—CH$_2$(CH$_2$)$_2$NH(CH$_2$)$_4$NH(CH$_2$)$_3$NHCOCH$_2$(NH$_2$) (CH$_2$)$_{42}$,
—CH$_2$(CH$_2$)$_2$NH(CH$_2$)$_4$NH(CH$_2$)$_3$NHCOCH$_2$(NH$_2$) (CH$_2$)$_3$ NHCH (NH) NH$_2$, or
—(CH$_2$)$_3$NH(CH$_2$)$_4$NH(CH$_2$)$_3$NHCOCH$_2$(NH$_2$) (CH$_2$)$_4$ NHCOCH$_2$(NH$_2$) (CH$_2$)$_4$NH$_2$ In addition, R$_2$ may be H, —CH$_3$, —CH$_2$CH (CH$_3$)$_2$ or —CH$_2$R$_3$. When R$_2$ is —CH$_2$R$_3$, R$_3$ may be a hydroxyphenyl group, a phenyl group, an acetyloxyphenyl group, a benzyloxyphenyl group, 4-hydroxy-3,5-diiodophenyl, an indolyl moiety, 4-nitro-5-hydroxyphenyl, 4-fluoro-5-hydroxyhenyl, 4-hydroxy-3,5-dichlorophenyl, or 4-hydroxy-3,5-dibromophenyl.

R$_4$ may be CH$_3$(CH$_2$)$_2$—, CH$_3$—, CH$_3$(CH$_2$)$_5$—, CH$_3$(CH$_2$)$_8$—, CH$_3$CH=CHCH=CH—, a cyclohexyl group, a benzyl group, a benzylmethyl group, a benzylethenyl group, an N$_3$-benzyl group, F$_3$CC (N$_2$) CONH(CH$_2$)$_3$—,

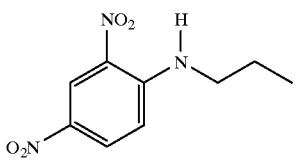

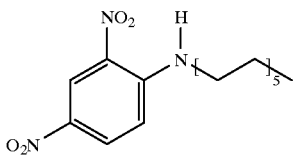

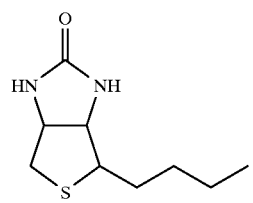

-continued

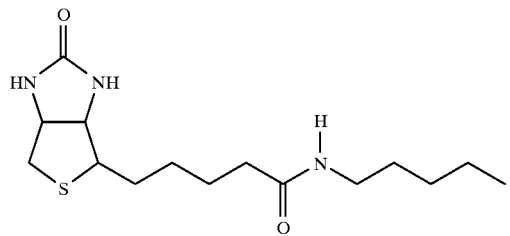

In one embodiment of the invention, the compound above has the structure:

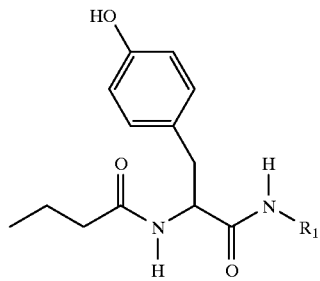

wherein R$_1$ is hydrogen,

—CH$_2$(CH$_2$)$_2$NH(CH$_2$)$_4$NH(CH$_2$)$_3$NH$_2$,
—CH$_2$(CH$_2$)$_3$NH(CH$_2$)$_3$NH(CH$_2$)$_3$NH$_2$,
—CH$_2$(CH$_2$)$_2$NH(CH$_2$)$_3$NH(CH$_2$)$_4$NH$_2$,
—CH$_2$(CH$_2$)$_3$NH(CH$_2$)$_3$NH$_2$,
—CH$_2$(CH$_2$)$_3$NH$_2$,
—CH$_2$(CH$_2$)$_3$NHCH$_2$CH (CH$_3$) CH$_2$NH(CH$_2$)$_3$NH$_2$,
—CH$_2$(CH$_2$)$_3$NHCH$_2$CH (C$_4$H$_9$) CH$_2$NH(CH$_2$)$_3$NH$_2$,
—CH$_2$(CH$_2$)$_3$N$^+$(CH$_3$)$_2$(CH$_2$)$_4$N$^+$(CH$_3$)$_2$ (CH$_2$)$_3$N$^+$(CH$_3$)$_3$,
—CH$_2$(CH$_2$)$_2$NH(CH$_2$)$_4$NH(CH$_2$)$_3$NHCOCH$_3$,
—CH$_2$(CH$_2$)$_2$NH(CH$_2$)$_4$NH(CH$_2$)$_3$NHCOCH$_2$NH$_2$,
—CH$_2$(CH$_2$)$_2$NH(CH$_2$)$_4$NH(CH$_2$)$_3$NHCO (CH$_2$)$_3$NH$_2$,
—CH$_2$(CH$_2$)$_2$NH(CH$_2$)$_4$NH(CH$_2$)$_3$NHCOCH$_2$(NH$_2$) (CH$_2$)$_4$ NH$_2$,
—CH$_2$(CH$_2$)$_2$NH(CH$_2$)$_4$NH(CH$_2$)$_3$NHCOCH$_2$(NH$_2$) (CH$_2$)$_3$ NHCH (NH)NH$_2$, or
—(CH$_2$)$_3$NH(CH$_2$)$_4$NH(CH$_2$)$_3$NHCOCH$_2$(NH$_2$) (CH$_2$)$_4$ NHCOCH$_2$(NH$_2$)(CH$_2$)$_4$NH$_2$

In the preferred embodiment of the above compound, R$_1$ is
—CH$_2$(CH$_2$)$_2$NH(CH$_2$)$_4$NH(CH$_2$)$_3$NH$_2$,
—CH$_2$(CH$_2$)$_3$NH(CH$_2$)$_3$NH(CH$_2$)$_3$NH$_2$,
—CH$_2$(CH$_2$)$_2$NH(CH$_2$)$_3$NH(CH$_2$)$_4$NH$_2$, or
—CH$_2$(CH$_2$)$_3$NHCH$_2$CH(C$_4$H$_9$)CH$_2$NH(CH$_2$)$_3$NH$_2$.

In another embodiment of the invention, the compound above has the structure:

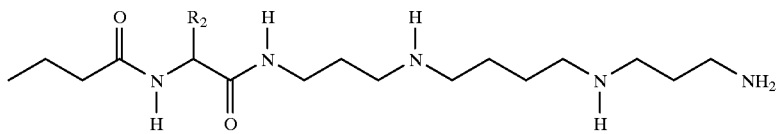

wherein $R_2$ is hydrogen, methyl, —$CH_2CH(CH_3)_2$ or —$CH_2R_3$; $R_3$ is hydrogen, a hydroxyphenyl group, a phenyl group, an acetyloxyphenyl group, a benzyloxyphenyl group, 4-hydroxy-3,5-diiodophenyl, an indolyl moiety, 4-nitro-5-hydroxyphenyl, 4-fluoro-5-hydroxyphenyl, 4-hydroxy-3,5-dichlorophenyl, or 4-hydroxy-3,5-dibromophenyl. In the preferred embodiment of the above compound, $R_2$ is $CH_2R_3$ and $R_3$ is a phenyl group, 4-hydroxy-3,5-diiodophenyl, or an indolyl moiety.

In yet another embodiment of the present invention, the compound above has the following structure:

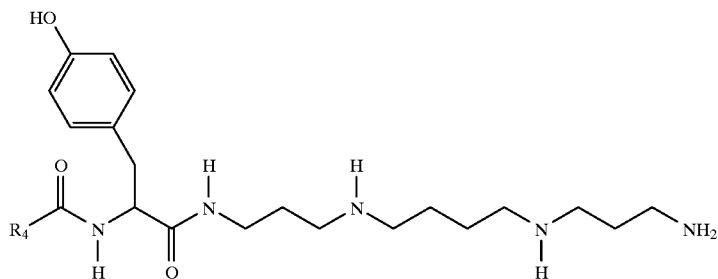

wherein $R_4$ is $CH_3(CH_2)_2$—, $CH_3$—, $CH_3(CH_2)_5$—, $CH_3(CH_2)_8$—, $CH_3CH=CHCH=CH$—, a cyclohexyl group, a benzyl group, a benzylmethyl group, a benzylethenyl group, an $N_3$-benzyl group, $F_3CC(N_2)CONH(CH_2)_3$—,

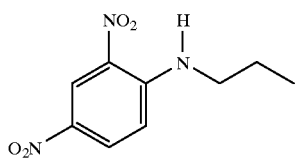

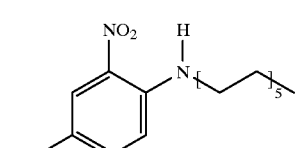

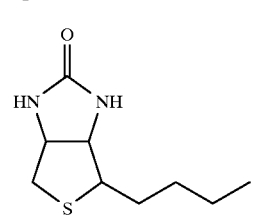

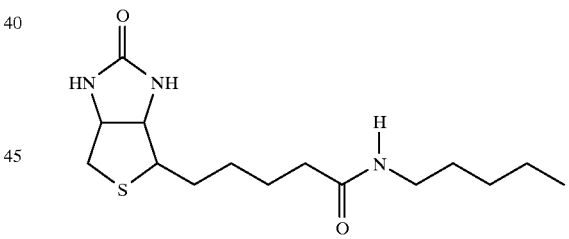

Preferably, $R_4$ is $CH_3(CH_2)_8$—, $CH_3CH=CHCH=CH$—, a benzyl group, a benzylethenyl group, or $N_3$-benzyl group.

The present invention also provides a compound wherein $R_1$ is

—$CH_2(CH_2)_2NH(CH_2)_4NH(CH_2)_3NHCOCH(NH_2)(CH_2)_4NH_2$ or

—$CH_2(CH_2)_2NH(CH_2)_4NH(CH_2)_3NHCOCH(NH_2)$ $(CH_2)_3NHC(NH)NH_2$;

$R_3$ is 4-hydroxy-3,5-diiodophenyl, a hydroxyphenyl group, or an indolyl moiety; and $R_4$ is $CH_3(CH_2)_8$—, $CH_3(CH_2)$—, or an $N_3$-benzyl group.

Preferably, the compound above has one of the following structures:

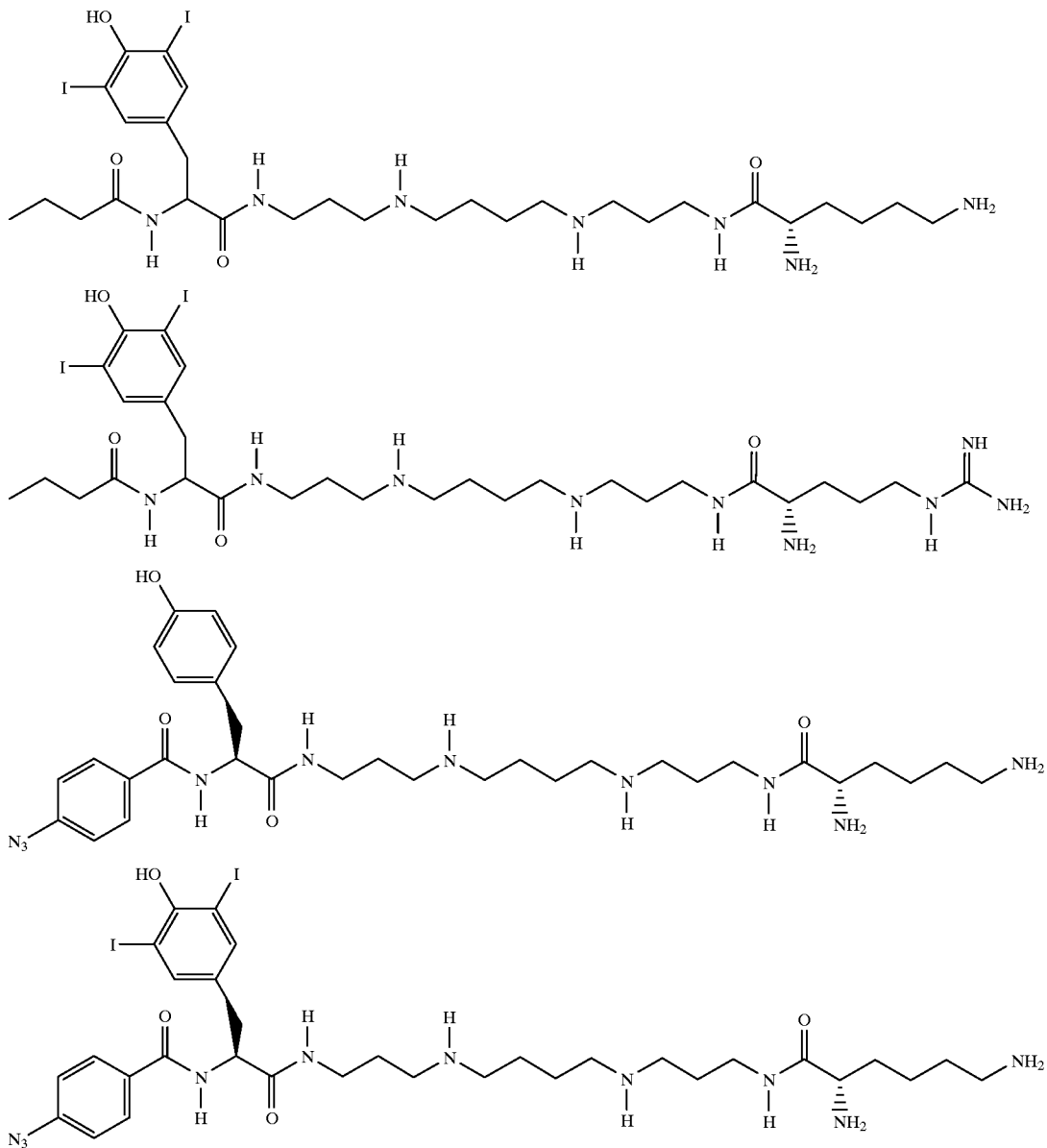
Additionally, the present invention provides for a compound having the structure:
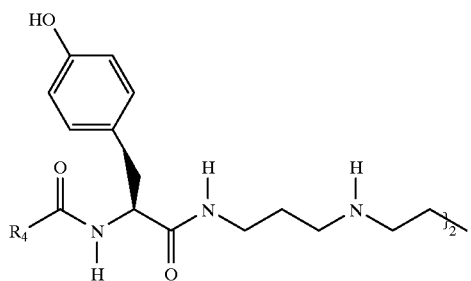
where in $R_4$ is $CH_3$—, $CH_3(CH_2)_2$—, $CH_3(CH_2)_5$—, $CH_3(CH_2)_7CH_2$—, or a benzyl group.
The present invention also provides a compound having the structure:
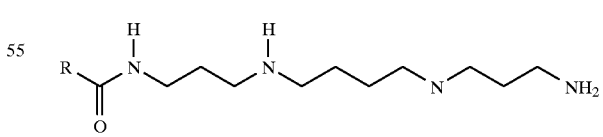
wherein R is $CH_3(CH_2)_2$—, $CH_3(CH_2)_5$—, or $CH_3(CH_2)_8$—.
The present invention also provides a compound having the structure:

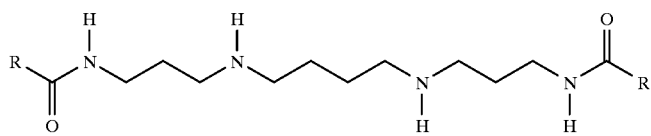

wherein R is $CH_3(CH_2)_2—$, $CH_3(CH_2)_5—$, or $CH_3(CH_2)_8—$.

The invention also provides a method of preparing or isolating the compound above. The method comprises treating venom, venom sacs or venom glands of the wasp *Philanthus triangulum* F. to produce an aqueous extract, and recovering the compound from the resulting aqueous extract. The recovery may be effected by a variety of separation techniques known to those skilled in the art to which the invention pertains, such as filtration, centrifugation, and chromatography. The treating of the venom, venom sacs, or venom glands may be effected by extraction with numerous organic solvents, such as 50% $CH_3CN—H_2O$. Preferably, a series of extractions is performed wherein each subsequent extraction is performed on the fraction resulting from the previous extraction.

The invention also provides a method of synthesizing the compound described hereinabove which comprises contacting a branched- or unbranched-chain alkylamine, having from two to twenty atoms in the chain and having hydrogen or a protection group attached to each nitrogen atom of the chain, with a compound having the structure:

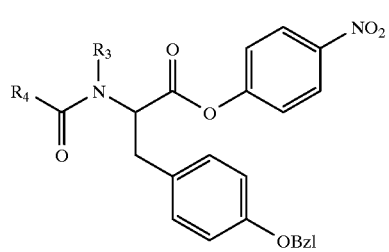

wherein $R_3$ and $R_4$ are the same or different and are hydrogen or a lower alkyl group, so as to form a product, treating the product to produce the compound and recovering the compound. The treating of the product may comprise deprotection with trifluoroacetic acid or hydrogen. Presently, the component having the structure:

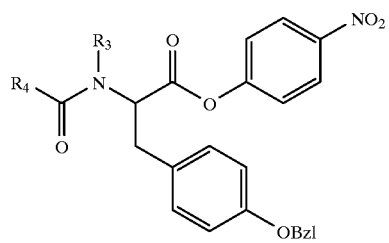

is obtained by the treatment of N-tert-butoxycarbonyl-o-benzyl-L-tyrosine p-nitrophenylester (preferably with trifluoroacetic acid) to remove the tert-butoxycarbonyl group followed by acylation (preferably with butyryl chloride). In certain embodiments, the alkylamine has the formula:

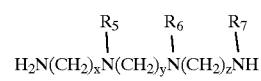

wherein each of x, y, z is the same or different and is an integer from 1 to 6 and each of $R_5$, $R_6$ and $R_7$ is the same or different and is hydrogen or a protection group. Several types of protection groups may be used in the practice of the present invention and these protection groups are well-known to those skilled in the art to which the invention pertains. Examples of useful protection groups include tert-butoxycarbonyl and carbobenzoxy groups and derivatives thereof. In the presently preferred embodiments, the alkylamine has the structure:

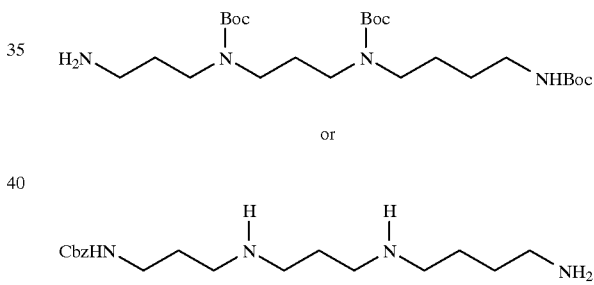

wherein Boc is a tert-butoxycarbonyl group and Cbz is a carbobenzoxy group. Such an alkylamine may be obtained by contacting acrylonitrile with a spermidine derivative having the structure:

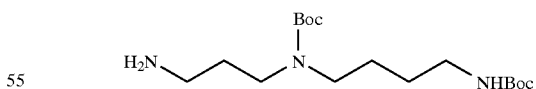

so as to produce a nitrile, and reducing the nitrile and treating it with $(Boc)_2O$ or carbobenzoxy chloride. In another preferred embodiment, the alkylamine has the structure:

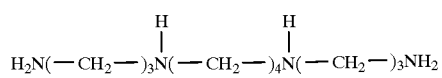

The present invention provides a compound having the structure:

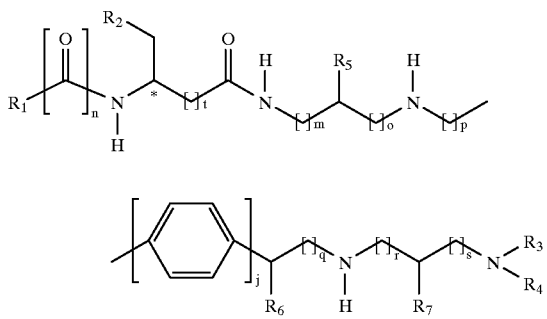

wherein $R_1$ is a saturated or unsaturated linear or branched chain alkyl group, or a cholestanyl group; wherein $R_2$ is a 2-indolyl, 3-indolyl, 4-indolyl, 5-indolyl, 4-hydroxyphenyl, 4-(arylalkyloxy)phenyl, 3,4-dihalophenyl, 4-hydroxy-3,5-dihalophenyl, 4-azidophenyl or 4-halophenyl group; wherein $R_3$ is H, a linear or branched chain alkyl or alkenyl group, or a phenyl, 2-azidophenyl, 3-azidophenyl, 4-azidophenyl group, or an a alkenylacyl, 3-amino-3-butylpropyl, N-[N-(N-{4-azidobenzoyl}aminopropyl)aminopropyl], cis- or trans-cinnamyl, 2-amino-2-[(4'-azidophenyl)acetyl, (trifluoromethyl)aminoacetyl or D- or L-arginyl group bonded through the α-carbonyl moiety thereof; $R_4$ is H, or a linear or branched chain alkyl group; wherein $R_5$, $R_6$ and $R_7$ are independently the same or different and are H, a linear or branched chain alkyl group, an aryl group or an arylalkyl group; wherein n, j and t are each 0 or 1; wherein m, o, p, q, r and s are independently the same or different and are 0, 1 or 2; wherein r+s and m+o are each equal to 2; wherein, if j is 0, p+q is 2; wherein, if j is 1, then q is 0 and $R_6$ is H; and wherein * denotes a D or L configuration. In a preferred embodiment, the present invention provides a compound having the above structure wherein j is 0 or 1. In another preferred embodiment, the present invention provides a compound having the above structure wherein k is 0 or 1.

The present invention also provides a compound having the structure:

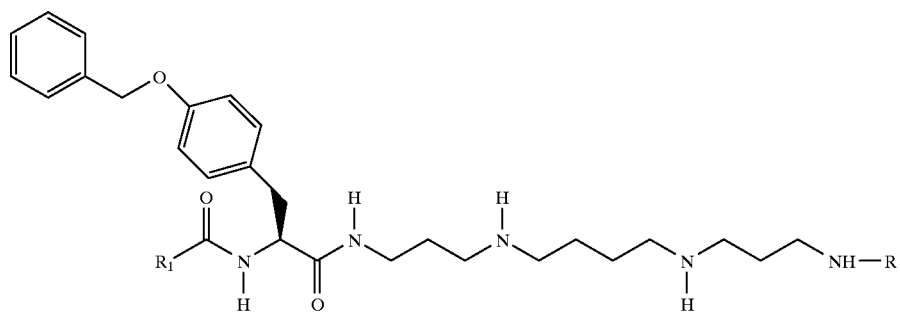

wherein R is selected from a group consisting of H, linear alkyl, linear acyl, arylalkyl, phenyl,

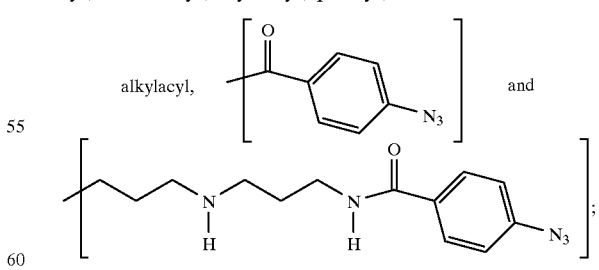

and wherein $R_1$ is a $C_9$ or $C_{10}$ linear alkyl group. In a preferred embodiment, the present invention provides a compound having the above structure wherein R is H and $R_1$ is $C_9H_{19}$. In another embodiment, the present invention provides a compound having the structure:

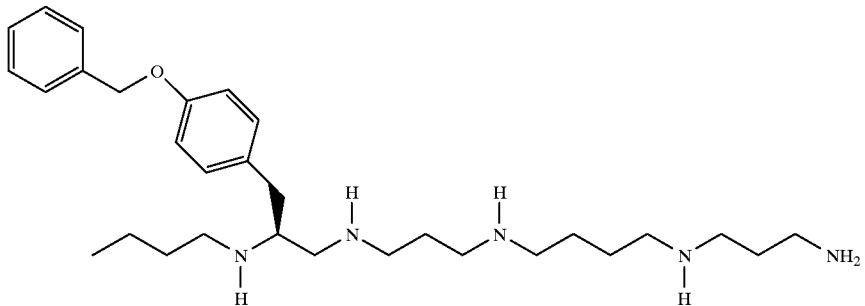

15

The present invention also provides a compound having the structure:

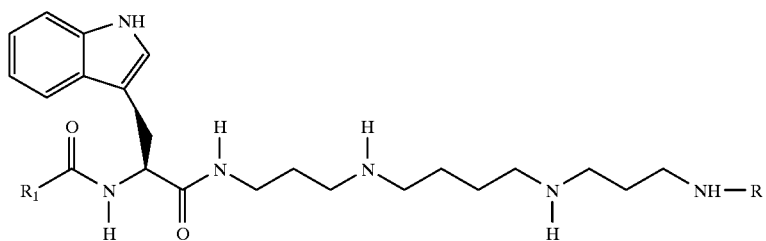

30 wherein R is selected from a group consisting of H,

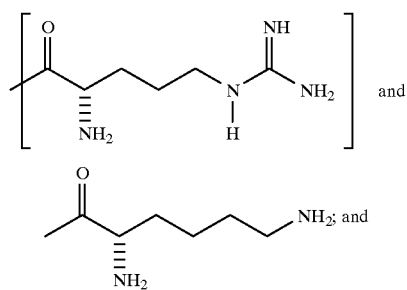

wherein $R_1$ is a $C_9$ or $C_{10}$ linear alkyl group. In one embodiment, the invention provides a compound having the above structure wherein R is H and $R_1$ is $C_9H_{19}$. In another embodiment, the present invention provides a compound having the above structure wherein R is

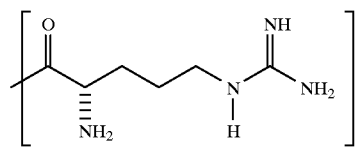

and $R_1$ is $C_9H_{19}$.

The present invention further provides a compound having the structure:

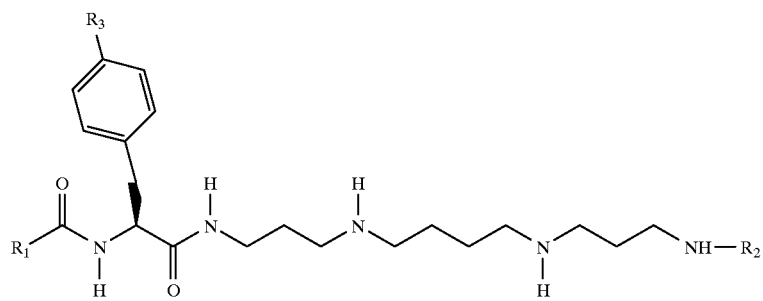

wherein $R_1$ is a $C_9$ or $C_{10}$ linear saturated or unsaturated alkyl group; wherein $R_2$ is selected from a group consisting of H, $H_2^+$,

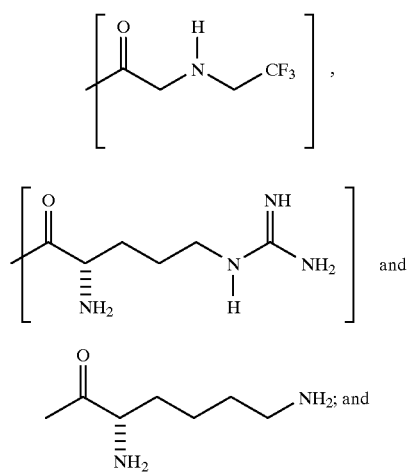

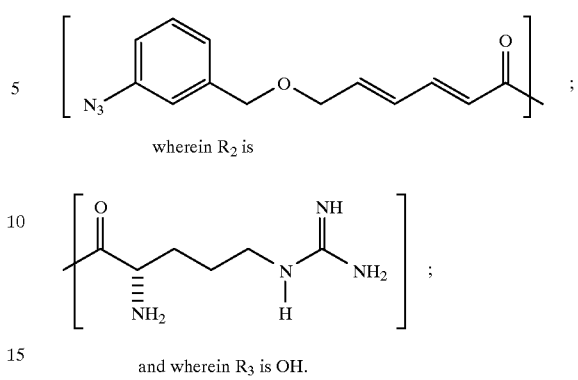

wherein $R_2$ is and wherein $R_3$ is OH.

The present invention also provides a compound having the structure:

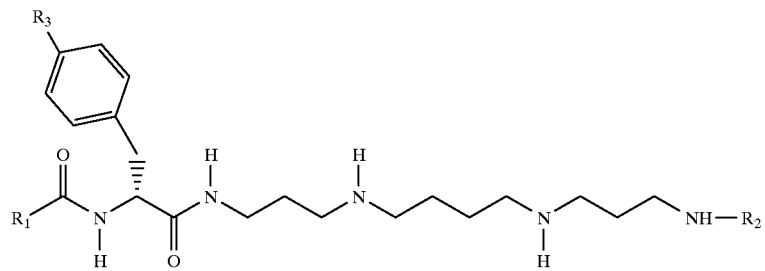

wherein $R_3$ is selected from a group consisting of F, OH and $N_3$. In one embodiment, the present invention provides a compound having the above structure wherein $R_1$ is a $C_9H_{19}$;
wherein $R_2$ is

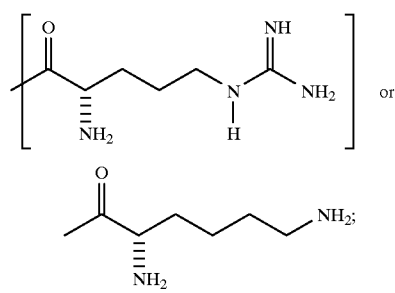

and wherein $R_3$ is OH.

In a preferred embodiment, the present invention provides a compound having the above structure wherein $R_1$ is wherein $R_1$ is a $C_9$ or $C_{10}$ linear saturated or unsaturated alkyl group; wherein $R_2$ is selected from a group consisting of H, $H_2^+$, and wherein $R_3$ is selected from a group consisting of F, OH and $N_3$. In one embodiment, the invention provides a compound having the structure:

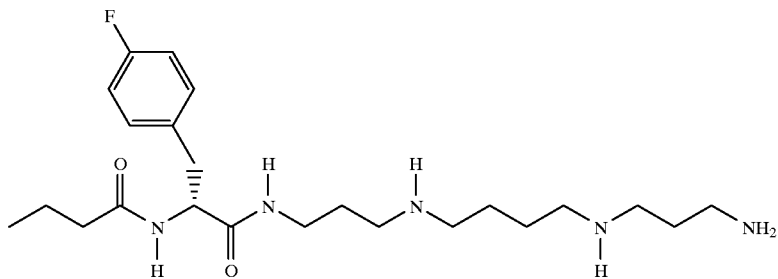

In another embodiment, the present invention provides a compound having the structure:

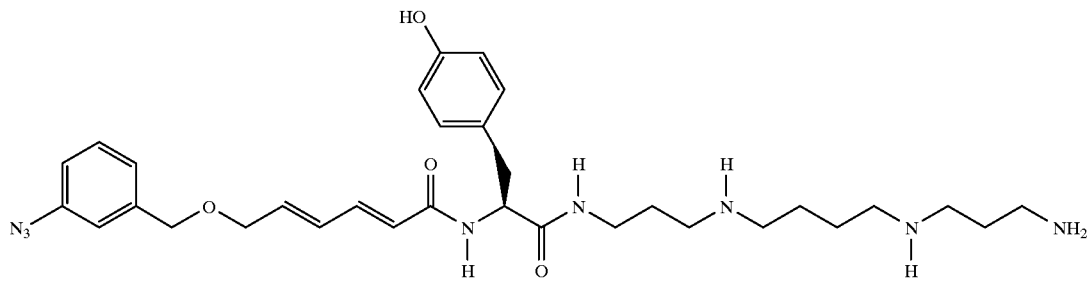

In another embodiment, the present invention provides a compound having the structure:

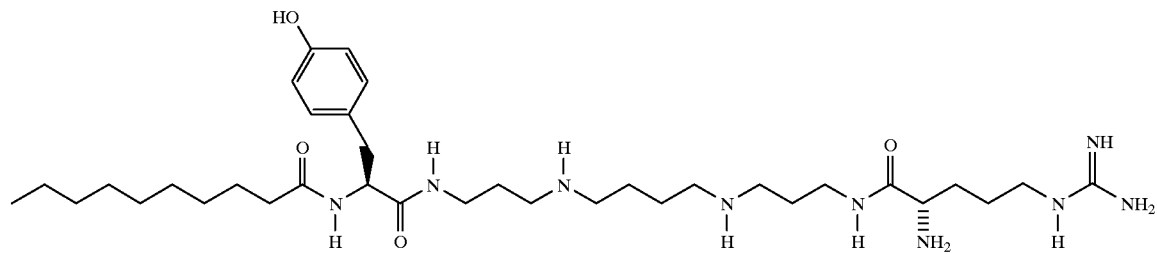

In another embodiment, the present invention also provides a compound having the structure:

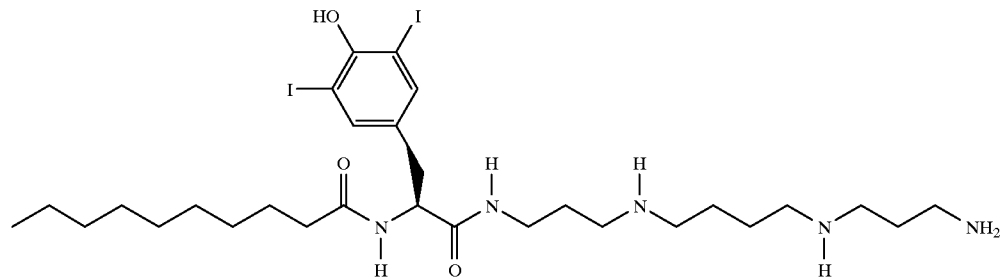

In an additional embodiment, the present invention provides a compound having the structure:

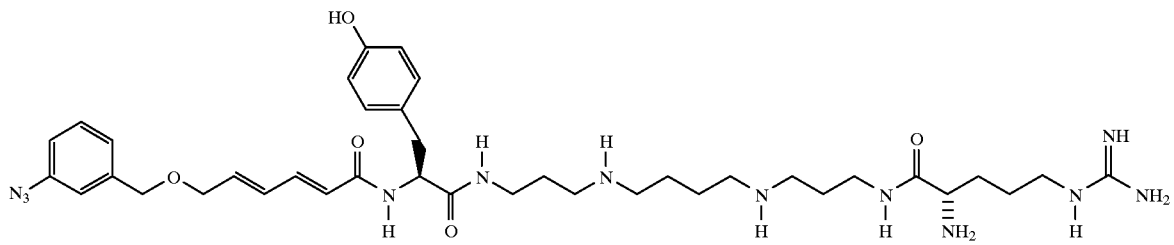

In another embodiment, the present invention provides a compound having the structure:

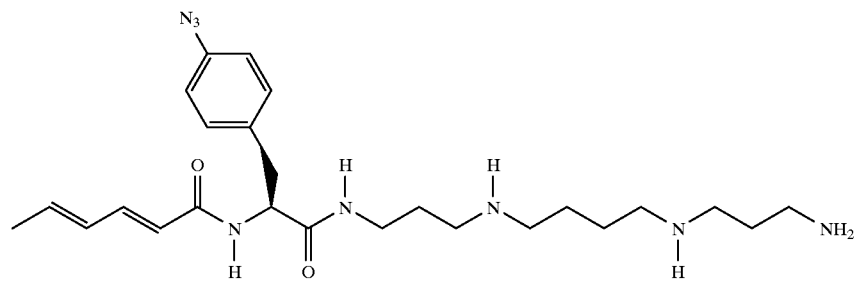

In another embodiment, the present invention also provides a compound having the structure:

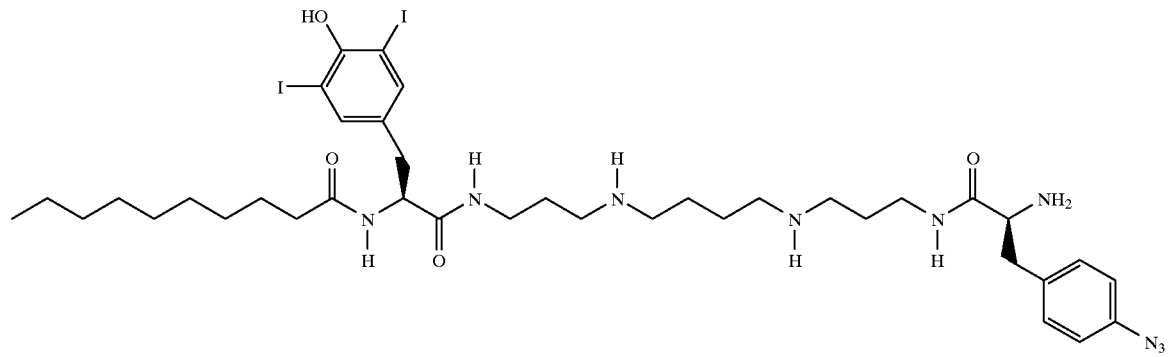

It is also contemplated that any of the compounds of the present invention may be radioactively labelled or be formulated into a pharmaceutical composition or an insecticidal composition comprising an effective amount of any one of the compounds and a suitable carrier. The compounds may also be mixed with glutamate to form an admixture which in turn may be mixed with a carrier to provide a pharmaceutical composition. The compounds may also be useful as an anticonvulsant.

Another aspect of the invention concerns a method of inhibiting binding to a glutamate receptor which comprises contacting the receptor with a binding-inhibiting amount of any of the compounds described hereinabove or the admixture of the compounds with glutamate. Such methods of inhibiting binding to a glutamate receptor may prove useful in medical applications, agricultural applications or as research tools for the study of humans and animals. In one embodiment, the invention provides a method of treating a subject afflicted by a disorder associated with binding of an etiological agent to a glutamate receptor which comprises administering to the subject an amount of any one of the compounds or the admixture effective to inhibit binding of the etiological agent to the receptor. The method is particularly useful where the receptor is the quisqualate or the NMDA receptor. In medical applications, the present invention may have therapeutic value in epilepsy, in movement disorders, in protection from ischemic brain damage and in various neurodegenerative disorders. The method may be useful where the neurodegenerative disorder is Huntington's disease, Parkinson's disease or Alzheimer's disease. Another embodiment provides a method of treating a subject afflicted by a stroke-related disorder associated with excessive binding of glutamate to glutamate receptors which comprises administering to the subject an amount of any one of the compounds or admixture effective to inhibit the excessive binding of the glutamate to the receptors.

As previously noted, the compounds may be mixed with a suitable carrier to form an insecticidal composition and the insecticidal composition may be used in a method of combating insects which comprises administering to the insects an amount of the insecticidal composition effective to induce paralysis in the insects.

This invention is illustrated in the Experimental Details section which follows. This section is set forth to aid in an understanding of the invention but is not intended to, and should not be construed to, limit in any way the invention as set forth in the claims which follow thereafter.

Experimental Details
A. Collection and Synthesis of PhTX-433

Collection of Wasp Venom and Bioassay. Female *Philanthus triangulum F.* were collected from Dakhla oasis in the great Sahara desert in Egypt in the late summer when the population of this wasp is very high. The wasps were restrained by chilling at 4° C. and their venom sacs and glands, with the sting apparati attached (FIG. 1), were removed and placed in liquid nitrogen, before being lyophilized and stored at −20° C. To test the biological activity of the crude venom preparation (water extract of the lyophilized venom glands), it was injected into honey bees. Honey bee workers (1–3 weeks old) were restrained by chilling at 4° C. then placed on their backs in a Lucite holder (16 bees to a holder) and injected in the ventral thorax behind the first pair of legs with 1 μl of water extract of the venom glands and immediately transferred to holding cages supplied with 40% sucrose solution. Controls received phosphate buffered Ringer.

HPLC fractionation of venom extracts. Venom glands were extracted with 50% $CH_3CN/H_2O$ and the extracts passed through a reverse-phase HPLC, YMC-ODS column 20×280 mm. A 5% to 95% linear gradient of $CH_3CN/H_2O$ containing 0.1% TFA was used for 30 min at a flow rate of 8 ml/min. The fraction of highest pharmacological activity was further purified on a reverse-phase YMC-ODS column 4×280 mm, developed by 15% $CH_3CN/H_2O$ containing 0.1% TFA for 15 min at a flow rate of 1 ml/min.

Electrophysiological studies. The metathoracic retractor unguis nerve-muscle preparation of the locust *Schistocerca gregaria* was dissected and mounted in a small Perspex bath as described previously (21). The muscle apodeme was attached to a Grass FT 10 strain gauge with a short strand of terylene and the muscle stretched to maximal body length. The total volume of the bath, including inlet and outlet reservoirs, was about 2.2 ml and the contents could be replaced within 1 sec. The dissection and setting up procedure were performed in continuously flowing saline. The muscle was stimulated indirectly through a fine (40–80μ) platinum wire electrode, insulated to its tip and placed on the retractor unguis nerve. The venom fractions were dissolved in locust saline of the following composition: NaCl, 140 mM; KCl, 10 mM; $CaCl_2$, 2 mM; $NaH_2PO_4$, 4 mM; $NaH_2PO_4$, 6 mM, and buffered at pH 6.8. The nerve muscle preparation was perfused with this saline at a flow rate of 5–10 ml/min at 19° C.

Experimental Results. Honey bees injected with water extracts of the venom glands were paralyzed in a dose-dependent manner. Time for recovery from paralysis was 15±3 min and 55±8 min for bees injected with 0.2 and 1.2 venom units (a unit is the extract from 1 wasp gland), respectively. Although all bees recovered within 1 hour, a dose-dependent mortality was evident after 24 hours (30, 80 and 100% mortality for bees injected with 0.4, 0.8 and 1.2 venom units). Polyacrylamide disc gel electrophoresis showed that the water extract of the venom glands contained a large number of proteins, all of which were precipitated by heating the extract at 100° C. for 10 min. The boiled extracts retained full activity when assayed on the locust nerve-muscle preparation or on honeybees.

Figure 2A:
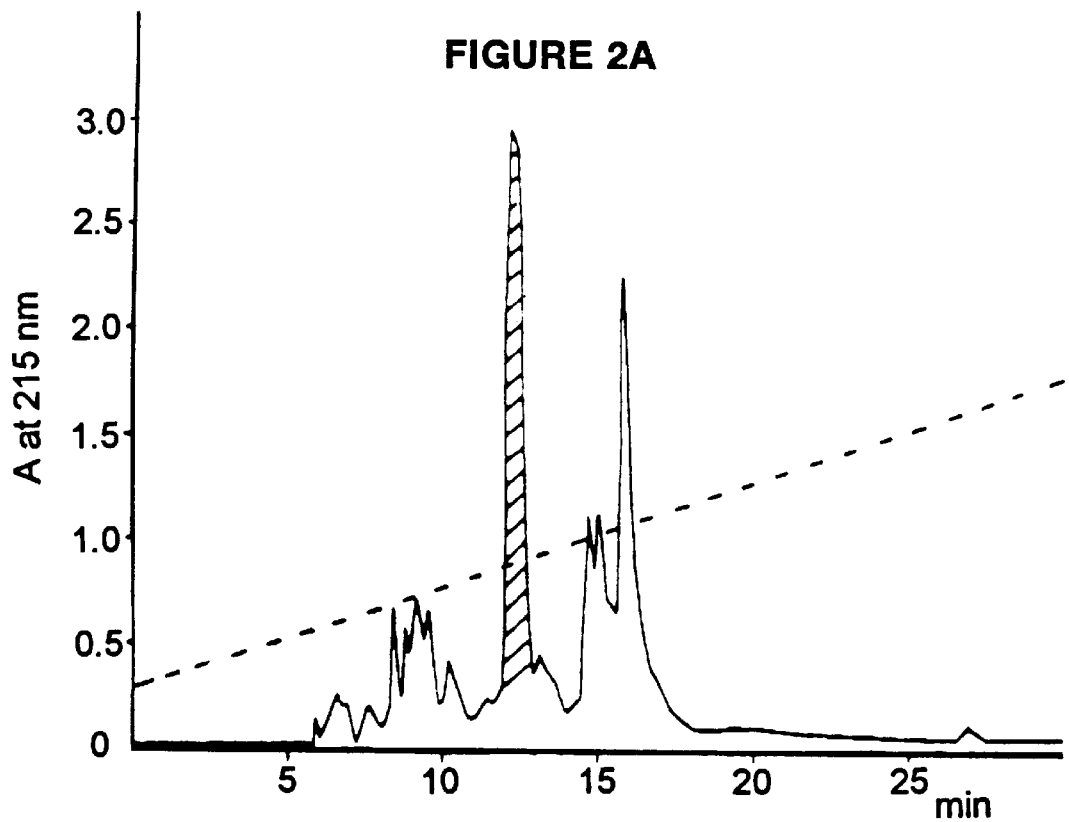
FIG. 2. Fractionation of Philanthus venom by reverse phase high pressure liquid chromatography (HPLC). (A) Fractionation of lyophilyzed venom glands, extracted in 50% acetonitrile/water. 450 µl (representing extracts of 225 wasps) were chromatographed on a YMC-ODS 20×280 mm column and developed by a linear gradient of 5% $CH_3CN$/ 0.1% TFA-95% $CH_3CN$/0.1% TFA for 30 min at a flow rate of 8 ml/min. UV absorption was monitored at 215 nm. (B) Fractionation of main toxic fraction (hatched peak in FIG. 2A).
Figure 2B:
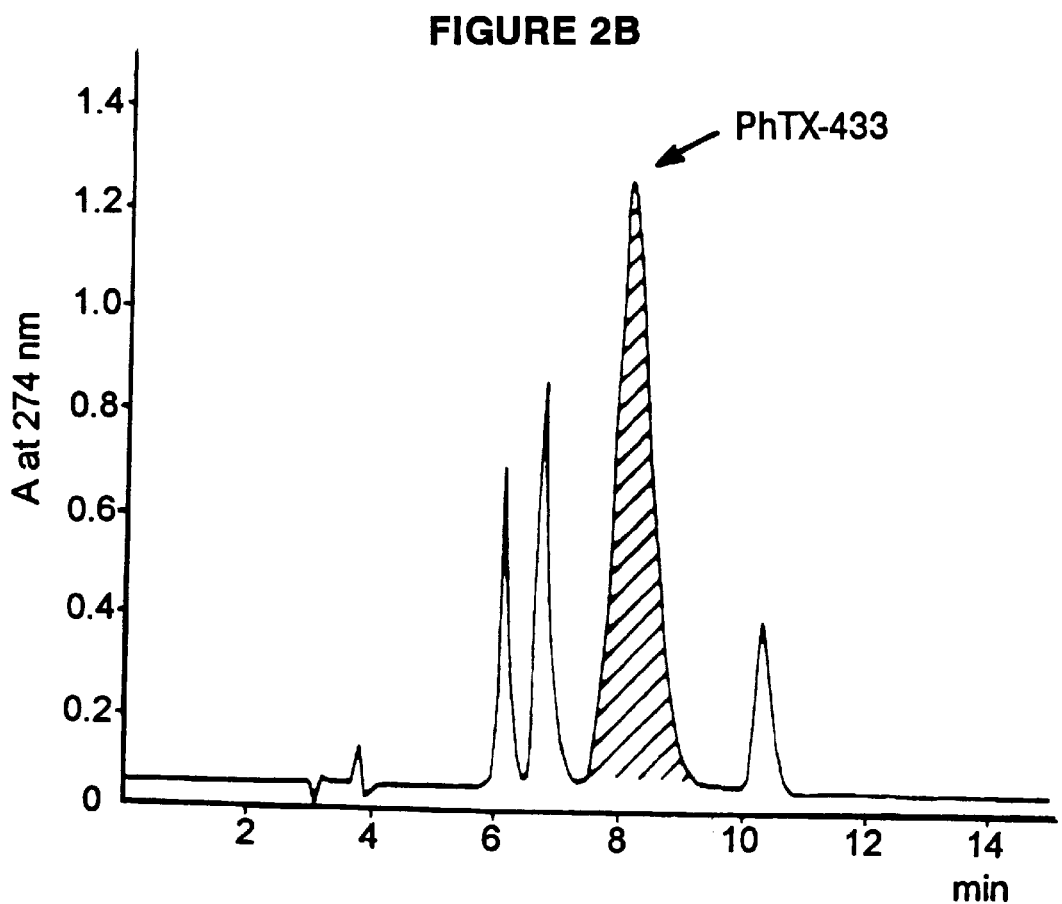

The extract of each batch of 1000 venom glands was fractionated by reverse-phase HPLC and 30 fractions collected. Each of the 30 fractions was tested for pharmacological activity on the locust nerve muscle preparation, using reduction in neurally evoked twitch amplitude as the measure of activity. Ten fractions were pharmacologically active. The most active fraction was the one collected at retention time 13 min (hatched peak in FIG. 2A). Further purification of this fraction by reverse-phase HPLC gave four peaks (FIG. 2B), the most pharmacologically was in the major peak (hatched FIG. 2B). This fraction gave 1.1 mg of toxin as amorphous powder.

The UV spectrum of 1 has a maximum of 274 nm, which shifts to 290 nm at pH 12, suggesting the presence of a tyrosine residue. This was supported by $^1$H-NMR (250 MHz in $D_2O$), δ3.00 (2H, d, J=7.8 Hz), 4.43 (1H, t, J=7.8 Hz), 6.88 (2H, d, J=8.7 Hz), 7.18 (2H, d, J=8.7 Hz). The presence of a butyrl group was also clear from $^1$H-NMR, δ0.83 (3H, t, J=7.2 Hz), 1.57 (2H, quin, J=7.2 Hz), 2.26 (2H, t, J=7.2 Hz). The $^1$H-NMR signal corresponding to six methylenes α to nitrogen at δ3.0–3.3 (12H, m) and four methylenes β to nitrogen at δ1.4–1.6(4H, m) and 2.1–2.2(4H, m) (22), together with the FAB-MS (M+H)$^+$ peak at m/z 436, showed the remainder of the molecule to be a polyamine of the spermine type. $^1$H-NMR measured in DMSO-$d_6$ (500 MHz) clarified the connectivity of the butyryl, tyrosyl and polyamine moieties; namely, two amide protons were observed at δ7.82 and 7.86 as a doublet and triplet, respectively, indicating that the former is due to tyrosine and the latter to polyamine. This leads to a butyryl/tyrosyl/polyamine sequence as shown in 1, 2 and 3 of FIG. 3A, but since spectroscopic evidence was ambiguous to differentiate the three, all isomers were synthesized.

Figure 3B:
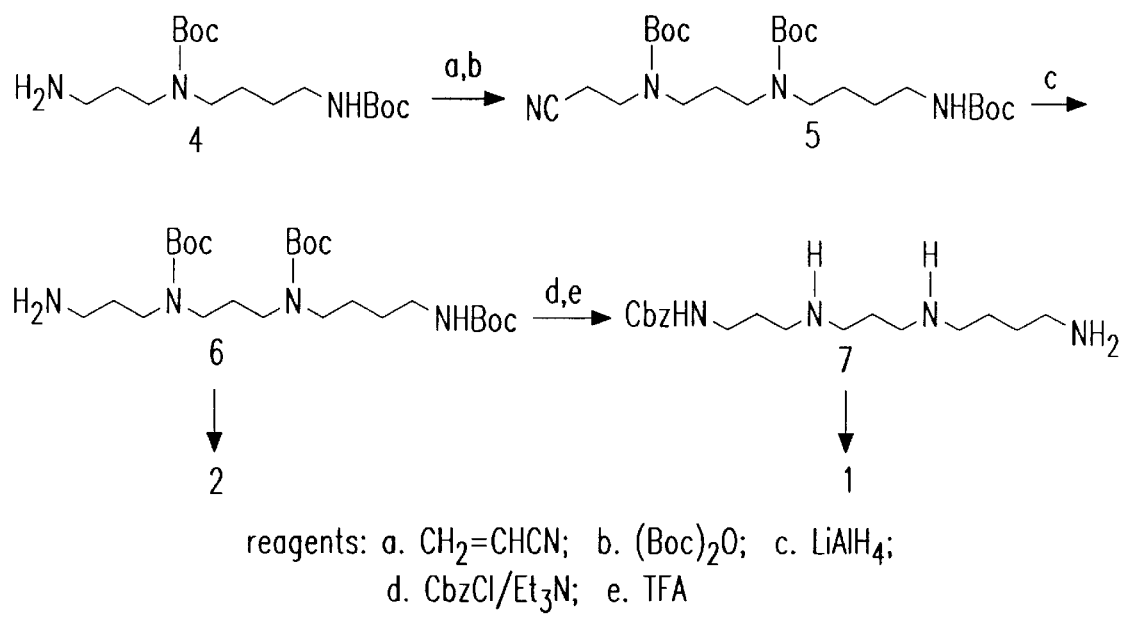
FIG. 3. The chemical structures and synthesis of the natural philanthotoxin PhTX-433 and two isomers PhTX-334 and PhTX-343. (A) The structures of the three toxins. (B) Synthesis of intermediates of compounds 1 and 2. (C) The final steps in synthesis of the three toxins.
Figure 3C:
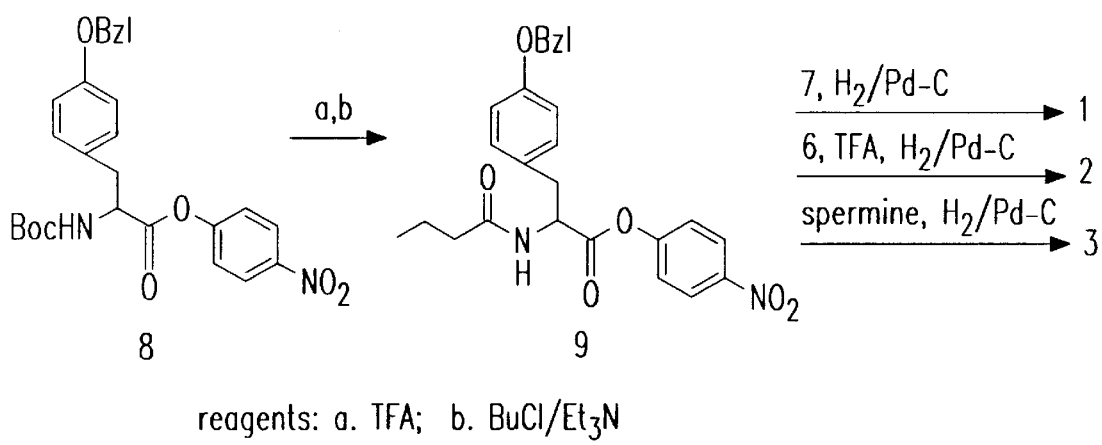

Chemical synthesis of the three isomers is illustrated in FIGS. 3B and C. The protected polyamine III was obtained from spermidine derivative I (23) through (i) Michael addition to acrylonitrile (76%); (ii) Boc-protection (81%); and (iii) reduction of the nitrile (70%). Further Cbz-protection and Boc-deprotection of III yielded partially protected polyamine IV (Boc represents tertbutoxycarbonyl and Cbz represents carbobenzoxy). Deprotection of N-Boc-O-benzyl-L-tyrosine p-nitrophenylester V (FIG. 3C) with trifluoroacetic acid (TFA) followed by acylation with butyryl chloride gave key intermediate VI in 85% yield. Coupling of VI with protected polyamines IV, III and commercial spermine (1,12-diamino-4,9-diazadodecane) (24), ca. 65% yield, followed by deprotection gave PhTX 1 and analogs, 2 (PhTX-334) and 3 (PhTX-343) (ca. 80% yield). Synthetic material derived from IV was found to be identical with the natural product in all respects ($^1$H-NMR, MS, CD, HPLC and biological activities). Thus the chemical structure of the major naturally-occurring philanthotoxin is 1, which is designated PhTX-433, the numerals denoting the number of methylene groups between the amino groups of the spermine moiety. All three of the synthetic end-products were biologically active, PhTX-334 having a higher potency than the natural PhTX-433 toxin, while PhTX-343 being somewhat less active.

Preliminary pharmacological studies with PhTX-433 suggested that its action on a locust nerve-muscle preparation was both time- and concentration-dependent. The effects of this toxin on the neurally-evoked twitch contraction of the locust retractor unguis muscle were investigated using toxin concentrations of 1–10 μM (21). It was clear from the data presented in FIG. 4A that PhTX-433 exerted a number of actions on the locust nerve-muscle system. There was an initial reduction in twitch amplitude, which was stimulus frequency independent. This was followed by a further reduction in the twitch height, the extent of this charge being directly proportional to the frequency at which the retractor unguis nerve was stimulated. Prolonged applications of PhTX-433 abolished the twitch. Immediately following removal of the toxin there was a brief period of operated and prolonged contractions in response to a single stimulus applied to the retractor unguis nerve before the twitch slowly returned to normal. PhTX-433 also reduced the response of the retractor unguis muscle to L-glutamate (0.1 $\mu$M; bath applied), which suggests that at least part of the reduction in twitch amplitude was due to the antagonism of postjunctional, quisqualate-sensitive glutamate receptors. PhTX-334(FIG. 4B) and PhTX-343 influenced the twitch contraction in the same qualitative fashion as PhTX-433. The physiological activity of PhTX-343 and PhTX-334 were, respectively, 80% and 125% that of PhTX-433 as measured by the locust muscle twitch inhibition concentration.

The natural philanthotoxin and its synthetic counterpart PhTX-433 and analogs PhTX-334 and PhTX-343(FIG. 3A) represent a new class of chemicals that are active biologically and inhibit allosterically the quisqualate-sensitive glutamate receptor in insect skeletal muscle (FIG. 4). They are smaller in molecular weight (435 daltons) than the toxins isolated from orb web spider venoms, the argiotoxins (>600 daltons) and easier to synthesize. (14,15,17,25).

Binding PhTX-433 to NMDA Receptor. The NMDA receptor is identified by its high affinity for the compound (+)-5-methyl-10,11-dihydro-5H-dibenzocyclohepten-5,10-imine maleate (MK-801). This compound is an anticonvulsant introduced by Merck Sharp & Dohme Co. and is a potent non-competitive antagonist of the NMDA receptor. Binding of [$^3$H]MK-801 to synaptic membranes from rat brain after thorough washing is extremely poor. However, the binding (measured by a filtration assay) is potentiated by glutamate in a dose-dependent manner and reaches maximal potentiation at 10 $\mu$M glutamate (26). The increase in binding of [$^3$H]MK-801 resulting from addition of glutamate has been used as an index of NMDA receptor binding. Philanthotoxin (PhTX-433) inhibited the binding of [$^3$H] MK-801 to NMDA receptors (FIG. 6) with an $EC_{50}$ (the concentration that inhibits 50% of binding) of 25 $\mu$M. Because of the difference in the maximal glutamate-induced [$^3$H]MK-801 binding in absence and presence of PhTX-433 (FIG. 5), it is suggested that MK-801 and PhTX-433 may affect the NMDA receptor by binding to distinct allosteric sites on the receptor protein.

B. Synthesis of PhTX-343 Analogs

A structure-activity study was undertaken in order to increase the inhibitory effect of an analog at a particular concentration ($IC_{50}$) in the locust muscle assay, operating on the assumption that an increase in activity would be observed as inhibition of muscle contraction at lower ligand concentrations. Spermine was used for the synthesis of most analogs because the biological activity of PhTX-343 was similar to that of natural PhTX-433 (80%) and because of its commercial availability. Furthermore, its symmetric structure makes it unnecessary to differentiate the two terminal amino groups when coupling to the p-nitrophenol activated esters; apparently only primary amines were reactive in this coupling since no product arising from the reaction of secondary amines were reactive in this coupling since no product arising from the reaction of secondary amines could be detected.

Figure 5:
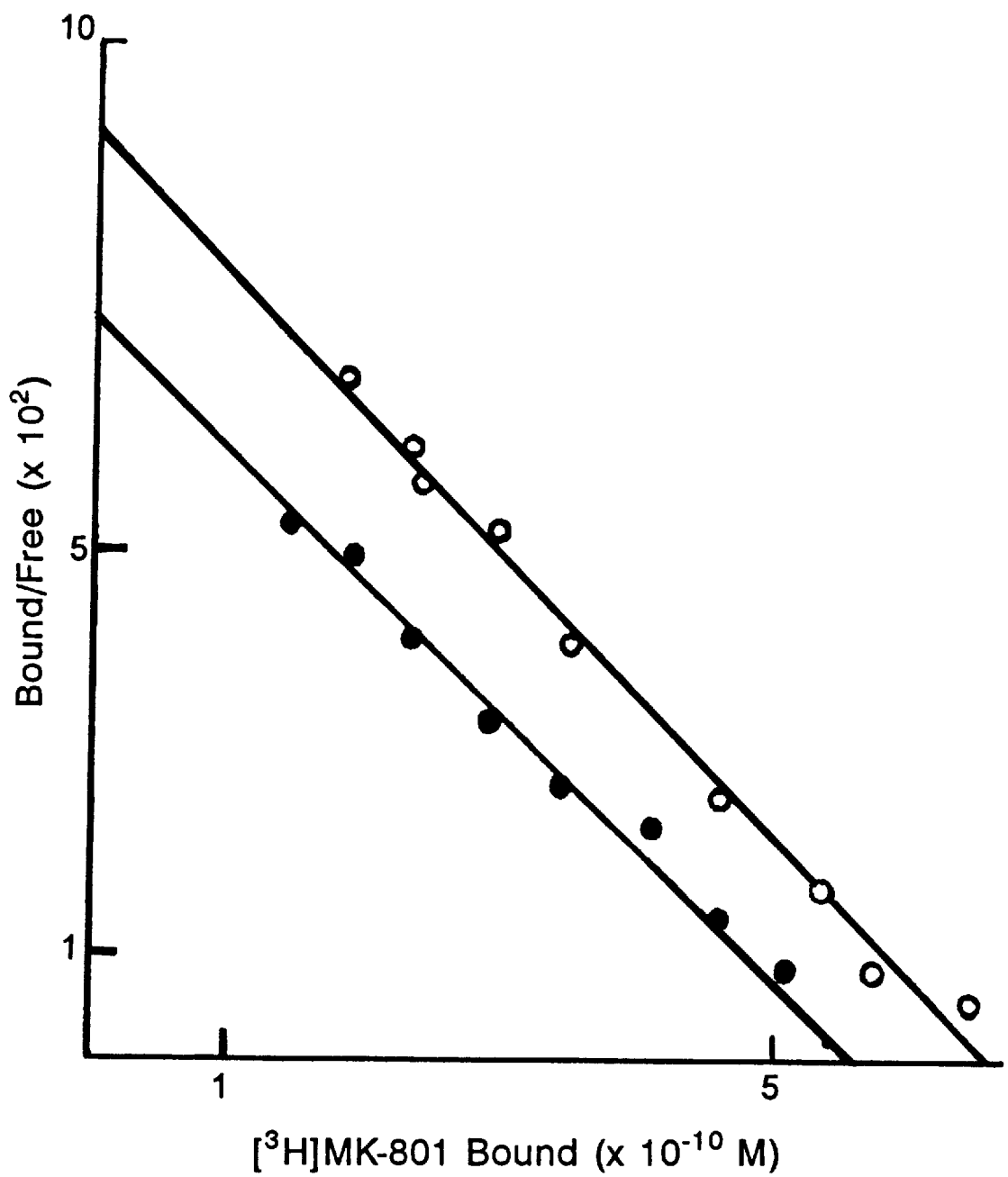
FIG. 5. Scatchard analysis of glutamate-induced [$^3$H]MK-801 binding in absence (○), and presence of (●) 25 µm PhTX.
Figure 6:
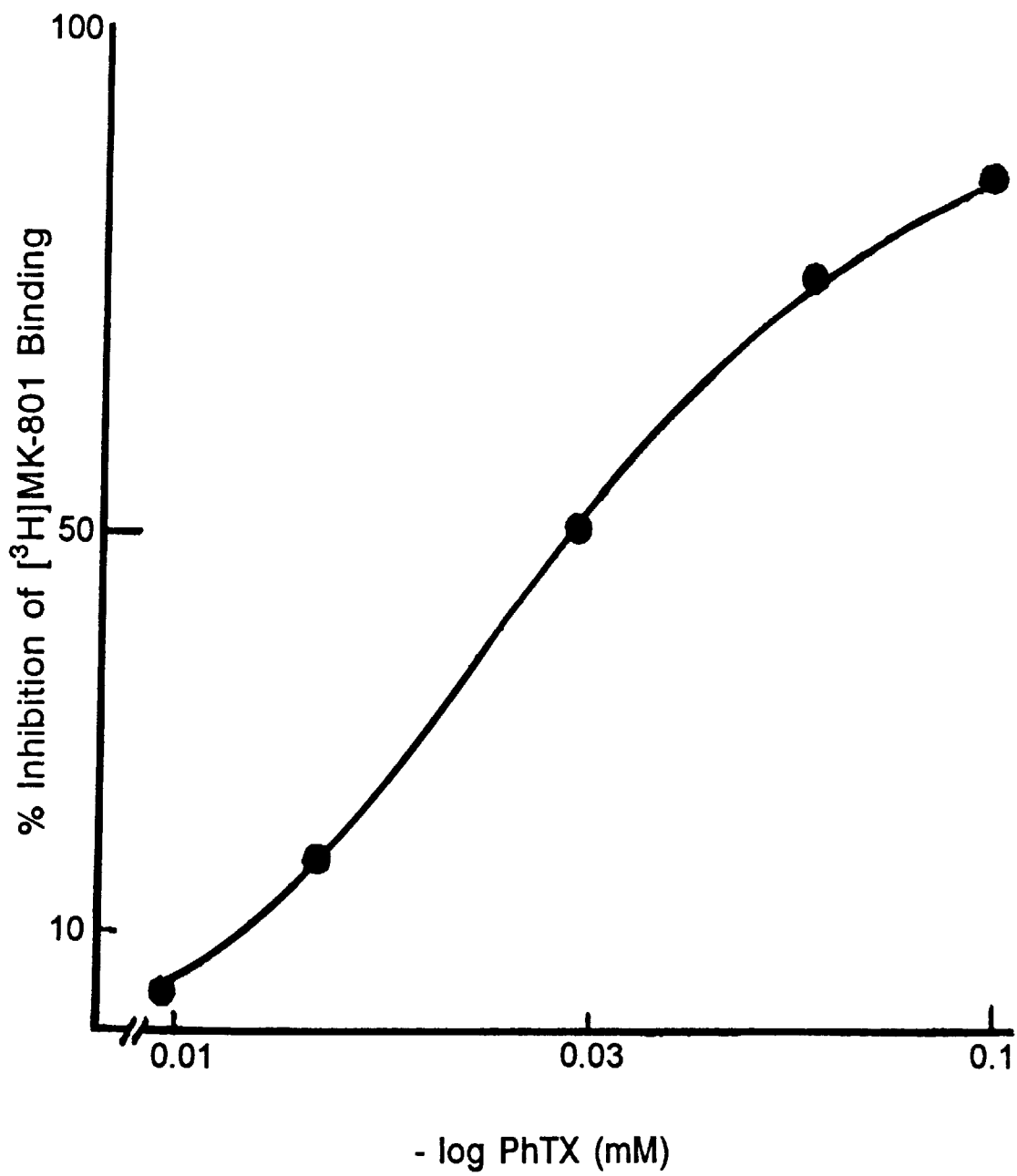
FIG. 6. Dose-dependent inhibition of the glutamate-induced [$^3$H]MK-801 binding to NMDA receptors of rat brain.
Figure 7A:
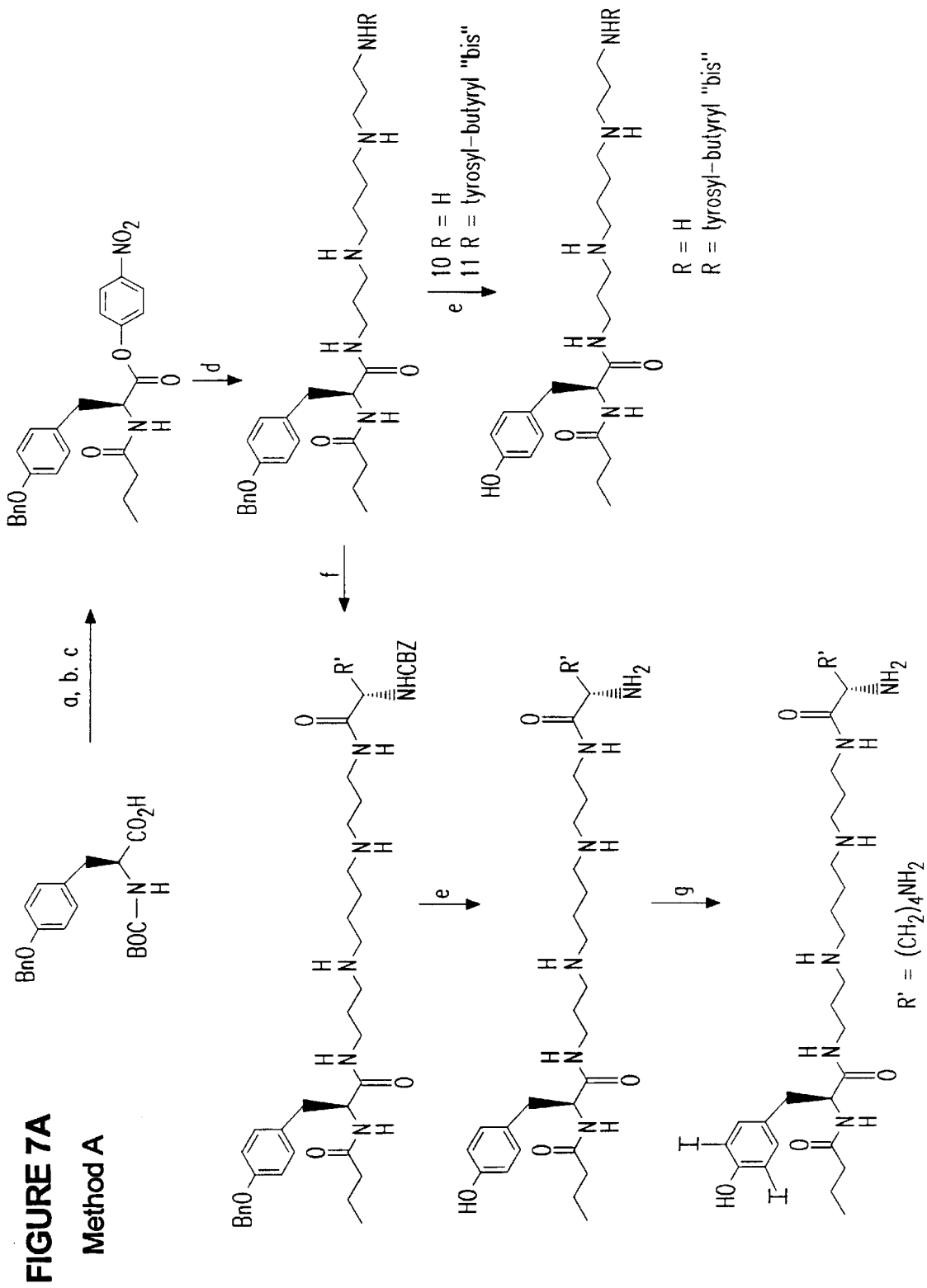
FIG. 7. Method A and Method B for preparing the analogs. a. p-nitrophenol, DCC, EtOAc; b. TFA, $CHCl_3$; c. $Et_3N$, butyryl chloride, $CHCl_3$; d. spermine, $CH_3OH$; e. $H_2$, 5% Pd/C, $CH_3OH$; f. N-α, ε-di-CBZ-L-lysine p-nitrophenol ester, DMF; g. NBS, KI, $K_2HPO_4$, $CH_3OH/H_2O$ (5:1); h. $(Boc)_2O$, $CH_3OH$,cat. pyridine; i. cinnamoyl chloride, $Et_3N$, $CHCl_3$.
Figure 8:
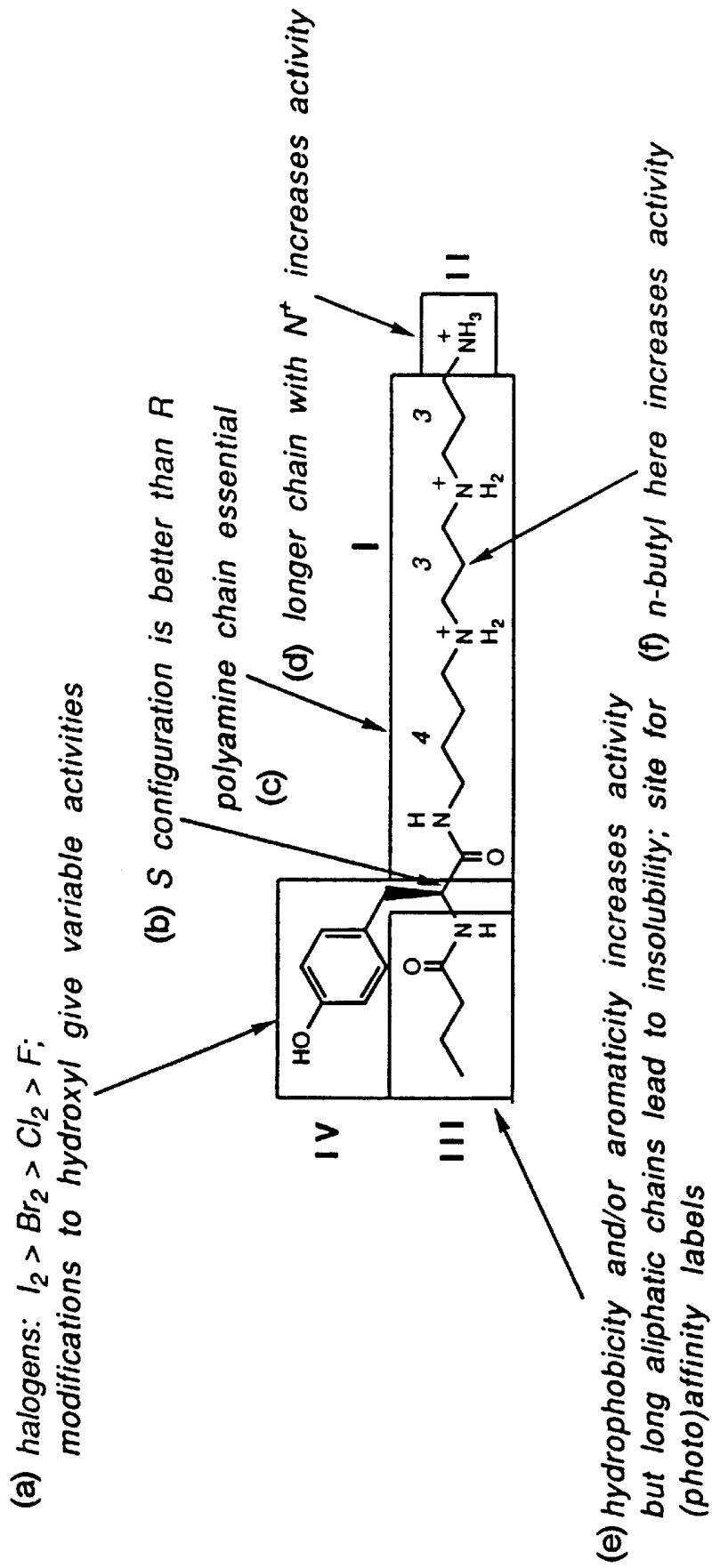
FIG. 8. (a) halogens: $I_2 > Br_2 > Cl_2 > F$; modifications to hydroxyl give variable activities. (b) S configuration is better than R. (c) polyamine chain essential. (d) longer chain with $N^+$ increases activity. (e) hydrophobicity and/or aromaticity increases activity but long aliphatic chains lead to insolubility; site for (photo) affinity labels. (f) n-butyl here increases activity. These structure activity relationships reflect general trends. Simultaneous modifications in regions II and IV are multiplicative or better, while regions II and III are less than multiplicative. When III=n-$C_9H_{19}CONH$—, further change reduces activity.
Figure 9:
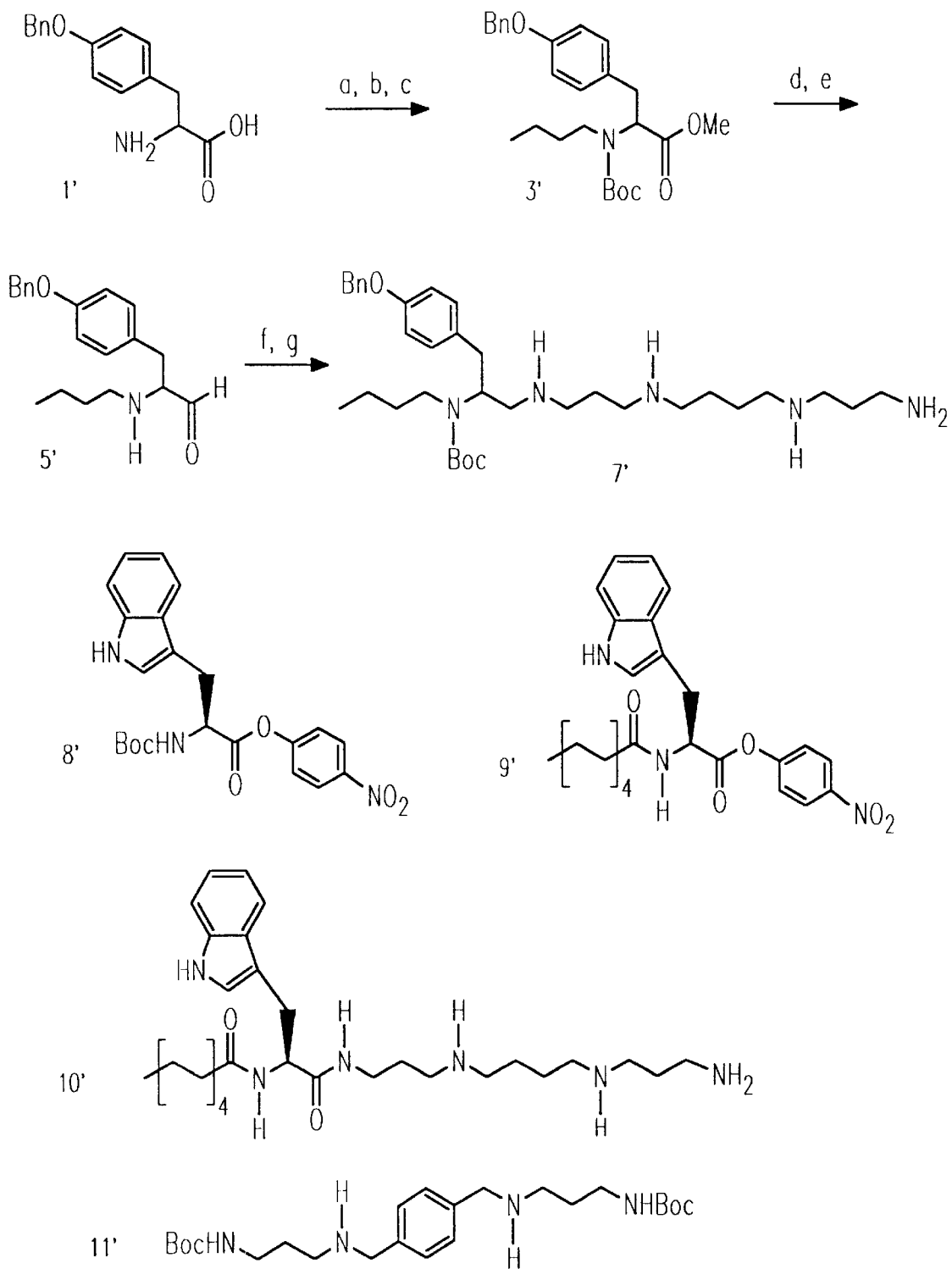
FIG. 9. Synthesis of 7'. a. $SOCl_2$, MeOH; b. Butyl bromide, KF/celite, $CH_3CN$; c. $(Boc)_2O$, $CH_2Cl_2$; d. DIBAL, $CH_2Cl_2$/hexane; e. $(CO)_2Cl_2$, DMSO, $Et_3N$, $CH_2Cl_2$; f. spermine, $Na_2SO_4$, $NaBH_4$; g. TFA, $CH_2Cl_2$. Compounds 8', 9', 10' and 11'.
Figure 10:
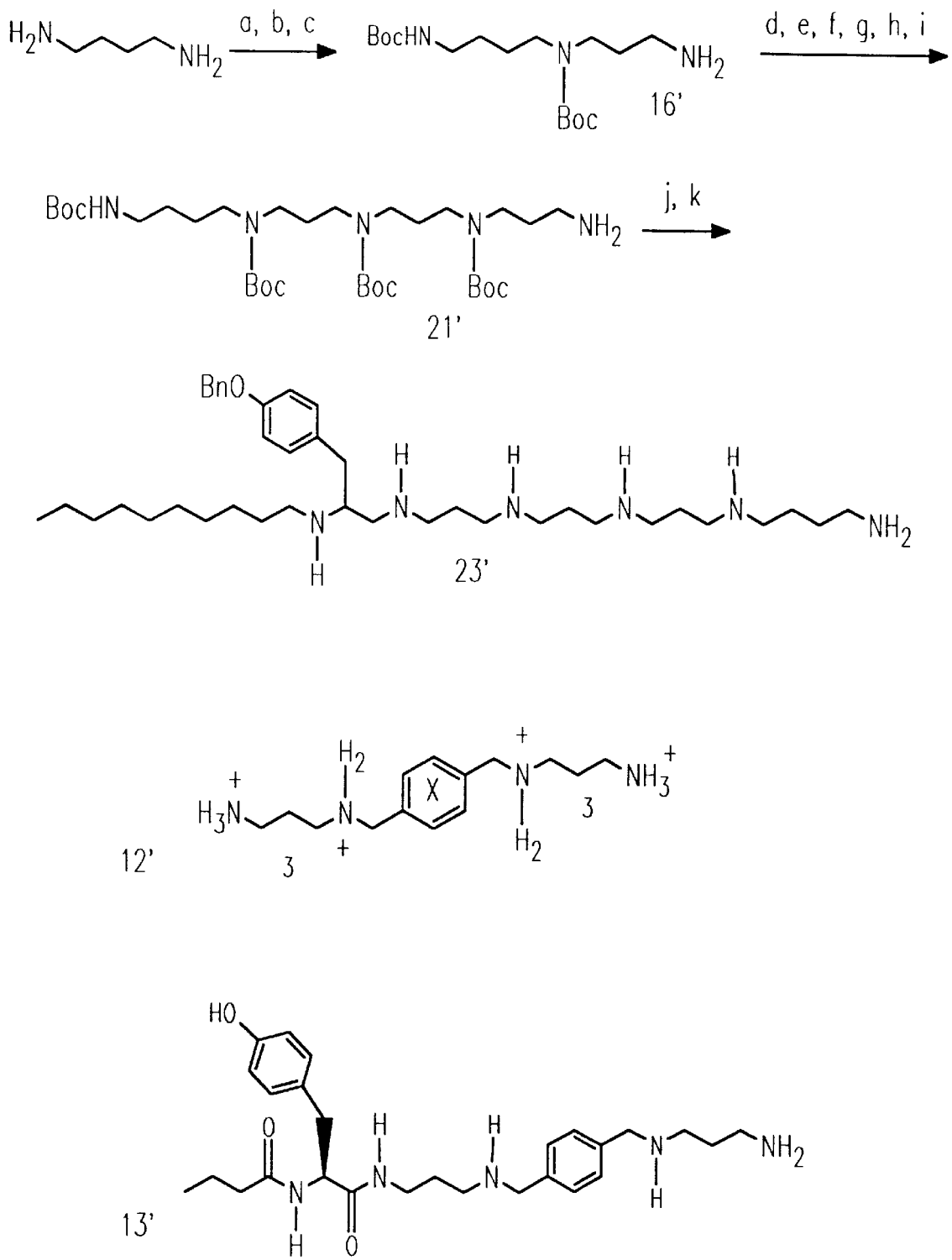
FIG. 10. Synthesis of 23'. a. acrylonitrile, MeOH; b. $(Boc)_2O$, $CH_2Cl_2$; C. $H_2$, 50 psi, $Pd(OH)_2$, AcOH; d. acrylonitrile, MeOH; e. $(Boc)_2O$, $CH_2Cl_2$; f. $H_2$, 50 psi, $Ph(OH)_2$, AcOH; g. acrylonitrile, MeOH; h. $(Boc)_2O$, $CH_2Cl_2$; i. $H_2$, 50 psi, $Pd(OH)_2$, AcOH; j. o-benzyl-Boc-decanoyl amine-tyrosine aldehyde, $Na_2SO_4$, $NaBH_4$; k. TFA, $CH_2Cl_2$. Compounds 12' and 13'.

The majority of analogs were synthesized according to Method A shown in FIG. 5 with only slight modifications if necessary. Taking into account the structural similarity between PhTX-433 and other neurologically active spider toxins, the molecule was divided into four moieties, A, B, C and D in order to assess the structure activity relation in a systematic manner. In Moiety C the butyryl moiety of the natural PhTX-433 suggests the possible necessity of a hydrophobic region in the molecule. Thus, analogs 18–24 were synthesized by exchanging butyryl chloride with the appropriate acyl chloride. In order to investigate the affect of the tyrosyl moiety in Moiety B, analogs 10–17 were prepared by the coupling of spermine and the p-nitrophenol esters of the corresponding N-butyryl amino acids. Analog 1 was obtained by treating N-BOC-tyrosine with acetic anhydride and triethyl amine before proceeding with Method A. Analogs 4 and 5 of Moiety A were obtained through coupling of polyamine intermediates and then hydrogenolysis; mixing ammonium acetate and hydrogenolysis yielded 6. Analogs 7 and 8 with branchings were prepared in order to examine the effects of alternating hydrophobic and hydrophilic regions and branching in the polyamine moiety; if active, a group suited for affinity binding to a solid support could be linked to the terminus of the branching. They were made by coupling of an ester and an alkylated 433-type polyamine; such alkyl polyamines were synthesized in the same manner as thermospermine (433) except that the an alkyl group was introduced by bromo-alkyl quenching of the lithiated anion $\alpha$ to the nitrile of the BOC-protected Michael adduct of diamino butane and acrylonitrile. These intermediates were then transformed into polyamines analogous to polyamine.

Arginine and other amino acids were linked to Moiety D, since in the spider toxins argiopine (28), NSTX-3 (29), argiotoxin 659 (25), and argiotoxin 673 (25), which show similar inhibition of locust muscle contraction (27), the polyamine moiety contains an additional arginine residue. Thus analogs 33–37 were synthesized by coupling O-benzyl-PhTX-343 with the p-nitrophenol esters of the corresponding amino acids, or in the case of 36, with commercially available $(CBZ)_3$-arginine N-hydroxysuccinimide ester followed by deprotection under hydrogenolysis conditions.

Analogs 25, 26, 28, 30, 40, and 41 were prepared to check the possibility of converting Moiety C into groups that could be used for photoaffinity labelling:26, 40, 41 or affinity labelling:28, 30. As these functionalities are sensitive to the hydrogenolysis conditions employed for O-benzyl deprotection, they were synthesized according to Method B shown in FIG. 5. Thus N-carbobenzyloxylation (Method B) instead of N-butoxycarbonylation (Method A) allowed hydrogenolysis to be performed prior to attachment of the functionality sensitive to reduction. N-tyrosyl acylation was achieved with either the free acid and diphenylphosphoryl azide or with the N-hydroxysuccinimide ester, depending on availability; in all cases the N-tyrosyl acylation preceded the BOC deprotection step.

The coupling reaction of p-nitrophenol esters with spermine (Method A, FIG. 5) invariably led to some formation of bis adducts, i.e., spermines acylated on both amino terminals. These bis analogs were easily separated, and upon hydrogenolysis yielded a series of bis-type PhTX analogs 42–46. These analogs were used in order to determine whether the effect of PhTX-type molecules on receptor/ membrane complexes is a channel-blocking mechanism or a membrane stabilization mechanism. It was also of interest to investigate the biological activities of simple mono- and bis-acylated spermine-343 molecules. Thus, three sets of mono- and bis-acyl spermine analogs 47–52 were similarly synthesized by reacting the appropriate p-nitrophenol esters with excess spermine.

Finally, radio-labelled analogs are necessary both for use in direct pharmacological characterization of receptors as well as for isolation of the glutamate receptor by photoaffinity labelling or affinity labelling. It was fortunate that introduction of iodine, which we had hoped to use for radio-labelling of the tryosyl moiety, also increased the biological activity approximately ten-fold. Cold iodinated analogs 13, 38, 39, 41 were prepared by use of NBS and KI on a milligram scale, while radioactive $^{125}$I analogs were prepared with Na$^{125}$I and chloramine T in buffered solution on a micro-scale and purified by reverse phase HPLC.

Experimental

CI-MS (NH$_3$) spectra were obtained on a Nermag-10 spectrometer while FAB-MS (3-nitrobenzyl alcohol matrix) spectra were obtained with a JOEL DX-303. Proton NMR spectra were recorded on a Brucker WM-250 instrument using residual proton solvent peaks of either CDCl$_3$ at 7.24 ppm or CD$_3$OD at 4.68 ppm as an internal standard. NMR spectra were measured in CD$_3$OD and as free bases unless specified. The solvents DMF and i-PrNH$_2$ and the reagents Et$_3$N and pyridine were distilled at atmospheric pressure over CaH$_2$. Acrylonitrile was distilled neat at atmospheric pressure. HPLC was used to identify the correct isomer of the natural product with the following column and conditions. Column: YMC-ODS, 4.6×250 mm; solvent: (12.5% CH$_3$CN, 0.1% TFA)/H$_2$O; flow rate: 1 mL/min.; detection: 274 nm.

2-(Diaminobutyl)-ethylnitrile

Acrylonitrile (3.1 g, 58.4 mmol) in 1.5 mL CH$_3$OH solution was added to 1.5 mL CH$_3$OH solution of diaminobutane (4.3 g, 48.8 mmol) at 0° and was stirred for 12 hr. The reaction was terminated by evaporation of the solvent and the oil was applied directly to a silica gel flash column, eluting with 3:1 CHCl$_3$:CH$_3$OH and 15:5:1, CHCl$_3$/CH$_3$OH/i-PrNH$_2$. The product was obtained as a clear oil in 65% yield. CI-MS (C$_7$H$_{15}$N$_3$): m/z 142 (M+1)$^+$; $^1$H NMR: δ1.32 (4H, complex) 1.53 (2H, br s), 1.65 (1H, s), 1.82 (1H, s), 2.35 (2H, t, J=6.6 Hz), 2.46 (3H, complex), 2.75 (2H, t, J=6.6 Hz).

2-(N,N'-di-BOC-diaminobutyl)-ethylnitrile

A solution of 2.82 g (20.0 mmol) of the above ethylnitrile and 4.8 g (22 mmol) of BOC anhydride in 70 mL of CH$_2$Cl$_2$ was stirred at room temperature for 12 hr.

The reaction was worked up by pouring the mixture into water and extracting with EtOAC three times. The combined organic layers were washed with aqueous NaHCO$_3$ and saturated NaCl solutions. After drying the solution over MgSO$_4$ and evaporating the solvent, the crude oil was chromatographed on silica with CHCl$_3$, followed by 1% CH$_3$OH/CHCl$_3$, yielding 4.2 g (75%) of the desired product. CI-MS (C$_{17}$H$_{31}$N$_3$O$_4$): m/z 342 (M+1)$^+$; NMR: δ1.40 (9H, s) 1.43 (9H, s) 2.57 (2H, br s), 3.08 (2H, q, J=6.1 Hz), 3.24 (2H, t, J=7.4 Hz), 3.42 (2H, t, J=6.7 Hz), 4.58 (1H, br s).

N',N"-di-BOC-polyamine-34

To a suspension of 0.062 g (1.63 mmol) of lithium aluminum hydride (LAH) in 10 mL of Et$_2$O was added 0.158 g (0.463 mmol) of the above nitrile at 0° C., and the mixture was stirred at 0° C. for 30 min. The excess LAH was quenched with 1 N NaOH at 0° C. and the resulting white suspension was filter through celite and washed with Et$_2$O. The filtrate was washed with water and the water layers were extracted with Et$_2$O. The combined Et$_2$O layers were washed with brine, dried over MgSO$_4$, and evaporated to yield the 0.108 g (68%) of the crude oil that was carried on to the next reaction without further purification. CI-MS (C$_{17}$H$_{35}$N$_3$O$_4$): m/z 346 (M+1)$^+$; NMR: δ1.37 (9H, s) 1.38 (9H, s), 2.61 (2H, t, J=6.7 Hz), 3.06 (4H, t, J=6.7 Hz), 3.18 (2H, br s), 4.65 (1H, br, s).

Di-BOC-polyamine-34-ethylnitrile

A mixture of 2.20 g (6.38 mmol) of the above N',N"-di-BOC-polyamine-34 and 0.63 mL (9.57 mmol) of acrylonitrile in 10 mL of CH$_3$OH was stirred at room temperature for 12 hr. The reaction was worked up by evaporation of solvent and chromatographed on silica gel with 1% then to 2% CH$_3$OH/CHCl$_3$ from which was obtained 2.47 g (97%) of the desired product. CI-MS (C$_{20}$H$_{38}$N$_4$O$_4$): m/399 (M+1)$^+$: NMR δ1.39 (9H, s), 1.40 (oH, s), 1.65 (2H, quintet, J=6.9 Hz), 2.47 (2H, t, J=6.8 Hz), 2.58 (2H, t, J=6.8 Hz), 2.87 (2H, t, J=6.8 Hz), 3.10 (4H, t, J=6.3 Hz), 3.20 (1H, br s), 4.58 (1H, br s).

Tri-BOC-polyamine-34-ethylnitrile

To a 20 mL CH$_3$OH solution of the above di-BOC-nitrile, 2.47 g (6.21 mmol) was added 1.62 g (7.45 mmol) of BOC anhydride. This mixture was stirred for 12 hr. The reaction was worked up on the same manner as for 3-(Di-N,N'-BOC-diaminobutyl)-ethylnitrile yielding 3.06 g (98%). CI-MS (C$_{25}$H$_{46}$N$_4$O$_6$): m/z 499 (M+1)$^+$; NMR: δ1.39 (9H, s), 1.40 (9H, s), 1.42 (9H, s), 1.71 (2H, quintet, J=7.4 Hz), 2.57 (2H, br s), 3.12 (4H, complex), 3.22 (2H, t, J=7.3 Hz), 3.43 (2H, t, J=6.7 Hz), 4.61 (1H, br s).

2',3',4'-tri-N-BOC-thermospermine

A CHCl$_3$ solution of the above tri-BOC-nitrile, 5.2 g (10.1 mmol) was treated with 2.4 g of LAH as described in the procedures for synthesis of N',N"-di-BOC-polyamine-34. The polyamine was obtained after silica column chromatography, 1:10 CH$_3$OH/CHCl$_3$ in 91% yield (4.61 g).

4'-N-CBZ-1',2',3'-tri-N-BOC-thermospermine

To a 10 mL CHCl$_3$ of 1 g (2.0 mmol) of the above 2',3',4'-tri-N-BOC-thermospermine and Et$_3$N (0.33 mL, 2.4 mmol) was added 0.34 mL (2.4 mmol) of CBZ-Cl and this mixture was stirred for 30 min at room temperature. The mixture after evaporation of the solvent was directly chromatographed on silica with 1% CH$_3$OH/CHCl$_3$. The desired product was obtained in 94% (1.12 g) yield. CI-MS (C$_{33}$H$_{56}$N$_4$O$_8$): m/z 637 (M+1)$^+$; NMR: δ0.79 (27H, s), 1.06 (4H, quintet, J=6.8 Hz), 2.46 (12H, complex), 4.41 (2H, s), 6.68 (5H, m).

Method A

N-BOC-O-benzyl-L-tyrosine-p-nitrophenol ester

To a solution of 3.33 g (9.0 mmol) of N-BOC-O-benzyl-L-tyrosine (Sigma) in 35 mL of EtOAc was added 1.25 g (9.0 mmol) of p-nitrophenol and 1.95 g (9.45 mmol) dicyclohexylcarbodiimide. The solution was stirred at room temperature for 1.5 hr and then filtered through celite. The resulting filtrate was extracted with water and sat. NaHCO$_3$. The aqueous extracts were then extracted three times with EtOAc. The combined organic layers were shaken 3 times with saturated NaCl solution, dried over MgSO$_4$, filtered, and evaporated to a slightly yellow, white powder. The powder was recrystallized from EtOH, to yield after filtration and washing with cold EtOH 3.44 g (78%) of a white powder. EI-MS (C$_{27}$H$_{28}$N$_2$O$_7$): m/z 492 (M$^+$); NMR: δ1.44 (9H, s), 3.15 (2H, d, J=5 Hz), 4.73 (3H, t, J=5 Hz), 5.10 (2H, s), 6.94 (2H, d, J=10.4 Hz), 7.12 (4H, d, J=10.4 Hz), 7,38 (5H, m), 8.22 (2H, d, J=10.4 Hz).

N-butyryl-O-benzyl-L-tyrosine-p-nitrophenol ester

To a solution of 2.95 g (6.0 mmol) of N-BOC-O-benzyl-L-tyrosine-p-nitrophenol ester in 30 mL of CHCl$_3$ was added 15 mL of trifluoroacetic acid (TFA) and this mixture was stirred at room temperature. After roughly 2 hr when all of the starting material was consumed according to TLC (silica, 35% EtOAc/hexane), the solution was evaporated to dryness. The resulting solid was suspended in 10 mL of CHCl$_3$ with stirring and to this suspension was added simultaneously 0.75 mL (7.20 mmol) of butyryl chloride and 2.50 mL (18.0 mmol) of Et$_3$N. The slightly yellow solution was stirred at room temperature. After 90 min the solution was evaporated to a slightly yellow solid and recrystallized with EtOH or chromatographed on silica with CHCl$_3$ yielding 2.0 g (72%) of the desired product. CI-MS (C$_{26}$H$_{26}$N$_2$O$_6$): m/z 463 (M+1)$^+$; NMR: δ1.05 (3H, t, J=7.8 Hz), 1.80 (2H, m, J=5.7 Hz), 2.58 (2H, t, J=5.7 Hz), 3.3 (2H, m), 5.15 (1H, m), 5.18 (2H, s), 6.94 (2H, d, J=10.4 Hz), 7.12 (4H, d, J=10.4 Hz), 7.38 (5H, m), 8.25 (2H, d, J=10.4 Hz).
N-butyryl-O-benzyl-L-tyrosine-spermineamide and Bis-spermineamide To a 10 mL CH$_3$OH solution of 0.36 g (0.78 mmol) of the previously made N-butyryl-O-benzyl-L-tyrosine-p-nitrophenol ester was added dropwise a 10 mL CH$_3$OH solution of 0.19 g (0.94 mmol) of spermine with stirring at room temperature. After 1 hour, the reaction mixture was evaporated to a yellow, semi-crystalline oil and 10 mL of CHCl$_3$/CH$_3$OH (1:1) was added to enhance crystallization of the p-nitrophenol. This suspension was filtered through celite and washed with 10 mL of CHCl$_3$/CH$_3$OH (1:1) solution. The filtrate was evaporated to a clear yell$_{\text{ow}}$ ow oil and then chromatographed on 25 g of silica with a step gradient system of 9:1 CHCl$_3$/CH$_3$OH, 15:5:1 CHCl$_3$/CH$_3$OH/i-PrNH$_2$ eluting the "Bis" adduct (11) 0.003 g (20%). CI-MS (C$_{50}$H$_{68}$N$_6$O$_4$): m/z 849 (M+1)$^+$; NMR: δ0.63 (6H, t, J=5.2 Hz), 1.32 (4H, q, J=6.8 Hz), 1.94 (4H, t. J=7.8 Hz), 4.25 (2H, t, J=7.8 Hz), 4.83 (4H, s), 6.70 (4H, d, J=8.3 Hz), 6.93 (4H, d, J=8.3 Hz), 7.19 (10H, m). The column elution with 4:4:1 CHCl$_3$/CH$_3$OH/i-PrNH$_2$ yielding 0.127 g (38.4%) of a clear, light yellow oil the previously made N-butyryl-O-benzyl-L-tyrosine-spermineamide. CI-MS (C$_{30}$H$_{47}$N$_5$O$_3$): m/z 526 (M+1)$^+$; NMR: δ0.72 (3H, t, J=5.2 Hz), 1.50 (10H, complex), 2.01 (2H, t, J=5.2 Hz), 2.55 (12H, complex), 4.48 (1H, t, J=7.8 Hz), 4.92 (2H, s), 6.88 (2H, d, J=8.3 Hz), 7.04 (2H, d, J=8.3 Hz), 7.27 (5H, m).
PhTX-343

To a 15 mL CH$_3$OH solution containing 0.20 g of (10) was added 0.2 g of 5% Pd/C. This solution was purged several times with hydrogen. The starting material was usually consumed after 2 to 3 hr. The reaction was terminated by filtration through celite and careful washing of the carbon with copious volumes of CH$_3$OH After evaporation of the solvent, the clear oil was chromatographed on 10 g of silica with 10:1 CHCl$_3$/CH$_3$OH and 4:4:1 CHCl$_3$/CH$_3$OH/i-PrNH$_2$. The desired product, 0.164 g (99%) was obtained as a clear oil. CI-MS (C$_{23}$H$_{41}$N$_5$O$_3$): m/z 436 (M+1)$^+$; NMR: δ0.74 (3H, t, J=5.2 Hz), 2.05 (2H, t, J=5.2 Hz), 4.33(1H, t, J=5.2 Hz), 6.58(2H, d, J=7.8 Hz), 6.94 (2H, d, J=7.8 Hz); HPLC retention time: 8.30 min, natural product 9.63 min.
Bis-PhTX-343 (43)

A 10 mL CH$_3$OH solution of 0.208 g (0.245 mmol) of (11) was treated in the same manner as for the synthesis of (2) above with 0.05 g of 5% Pd/C. The reaction mixture was purified on a silica flash column with 15:5:1 CHCl$_3$/CH$_3$OH/i-PrNH$_2$ yielding 0.124 g (76%) of the desired product. CI-MS (C$_{36}$H$_{56}$N$_6$O$_6$): m/z (M+1)$^+$; NMR: δ0.68 (6H, t, J=5.2 Hz), 1.98 (4H, t, J=5.2 Hz), 4.52 (2H, t, J=5.5 Hz), 6.77 (4H, d, J=8.8 Hz), 7.12, (4H, d, J=8.8 Hz).
O-benzyl-PhTX-2'3'-N,N-BOC-334

To a stirred solution of 0.022 g (0.44 mmol) of the above 2',3',4'-tri-N-BOC-thermospermine in 0.4 mL of CH$_3$OH was added 0.018 g (0.04 mmol) of the previously made N-butyryl-O-benzyl-tyrosine-p-nitrophenol ester and the mixture was stirred for 15 min. After evaporation of the solvent, the mixture was loaded onto a silica flash column and eluted with 1% CH$_3$OH/CHCl$_3$ yielding 13 mg (39%) of the desired product.
PhTX-334

To a stirred solution of 0.195 g (0.25 mmol) of O-benzyl-PhTX-di-2',3'-N,N-BOC-334 in 3 mL of CHCl$_3$ was added 3 mL of TFA and this mixture was stirred at room temperature for 15 min. After evaporation of the solvent, the crude oil was loaded onto a silica flash column and eluted with a step gradient of 15:5:1 and 3:3:1 CHCl$_3$/CH$_3$OH/i-PrNH$_2$ which yielded 0.072 g (67%) of the desired product. This pure free amine was dissolved in 3 mL of CH$_3$OH and this solution was stirred with 0.07 of 5% Pd/C under a hydrogen atmosphere at room temperature for 12 hr. The reaction was terminated by filtration and washing through celite with CH$_3$OH followed by removal of solvent in vacuo and then loading onto a silica flash column, eluting with a step gradient of 15:5:1 and 3:3:1 CHCl$_3$/CH$_3$OH/i-PrNH$_2$ yielding 0.045 g (75%) of the desired product as a clear oil. CI-MS (C$_{23}$H$_{41}$N$_5$O$_3$): m/z 436 (M+1)$^+$; NMR: δ0.67 (3H, t, J=7.4 Hz), 1.35 (2H, sextet, J=7.4 Hz), 1.99 (2H, t, J=7.3 Hz), 4.20 (1H, t, J=7.5 Hz), 6.52 (2H, d, J=8.3 Hz), 6.86 (2H, d, J=8.3 Hz); HPLC retention time: 8.43 min, natural product 9.63 min.
O-benzyl-PhTX-4'-N-CBZ-433

To a stirred solution of 244 mg (0.52 mmol) of the previously made N-butyryl-O-benzyl-tyrosine-p-nitrophenol ester in 1 mL of CH$_3$OH was added 200 mg (0.65 mmol) of the previously made 4'-N-CBZ-1',2',3'-tri-N-BOC-thermospermine in 1 mL of CH$_3$OH. This mixture was stirred for 15 min at room temperature. After evaporation of the solvent, the crude yellow oil was loaded onto a silica gel column and the desired product was eluted with a step gradient of 2% CH$_3$OH/CHCl$_3$ and 15:5:1 CHCl$_3$/CH$_3$OH/i-PrNH$_2$ which yielded 5 mg (23%).
PhTX-433

A mixture of 310 mg (0.47 mmol) of O-benzyl-PhTX-4'-N-CBZ-433 and 310 mg of 5% Pd/C in 1 mL of CH$_3$OH was stirred under hydrogen atmosphere for 12 hr. The mixture was then filtered and washed through; celite with CH$_3$OH before loading onto a silica flash column and eluting with a step gradient of 15:5:1 and 3:3:1 CHCl$_3$/CH$_3$OH/i-PrNH$_2$. Thus 100 mg (49%) of the desired compound was obtained in the form of a clear oil. CI-MS (C$_{23}$H$_{41}$N$_5$O$_3$): m/z 436 (M+1)$^+$; NMR: δ0.58 (3H, t, J=7.4 Hz), 1.90 (2H, t, J=7.2 Hz), 4.16 (1H, t, J=8.4 Hz), 6.44 (2H, d, J=4 Hz), 6.78 (2H, d, J=8.4 Hz); HPLC retention time: 9.63 min, natural product 9.63 min, co-injection of synthetic and natural products eluted as one peak at 9.63 min.
Moiety D
(i) O-benzyl-PhTX-343-N-α-N$^G$,N$^{G'}$-tri-CBZ-L-arginine-amide To a 5 mL DMF solution of 0.452 g (0.816 mmol) of N-butyryl-O-benzyl-L-tyrosine-spermineamide was added 0.58 g (0.86 mmol) of N-α-N$^G$,N$^{G'}$-tri-CBZ-L-arginine-N-hydroxysuccinimide ester (Bachem), and this solution was stirred overnight at room temperature. The reaction was worked up by evaporation of the solvent and extraction of the slightly yellow oil with CHCl$_3$ and washing the organic extracts with aqueous NaHCO$_3$, water, and brine. The crude product was chromatographed on silica with 9:1 CHCl$_3$/CH$_3$OH and 15:5:1 CHCl$_3$/CH$_3$OH/i-PrNH$_2$ to yield 0.817 g (91%) of the desired product. NMR: δ0.82 (3H, dt*, J=1.5, 7.5 Hz), 2.11 (2H, complex*), 4.25 (1H, br s*), 4.52 (1H, br s*), 4.52 (1H, br s*). 5.0–5.2 (8H, complex*), 6.85 (2H, d, J=8.6 Hz), 7.10 (2H, d, J=8.6 Hz), 7.30 (20H, complex).
*Complex couplings were due to a mixture of conformational isomers.

(ii) PhTX-343-L-arginine-amide

To a 10 mL $CH_3OH$ solution of 0.81 g (0.74 mmol) of O-benzyl-PhTX-343-N-α-$N^G$,$N^{G'}$-tri-CBZ-L-arginine-amide was added 0.05 g of 5% Pd/C followed by hydrogenolysis at room temperature overnight. The reaction mixture was filtered and washed through a column of 12 g of silica eluting with a step gradient of 1:1 $CH_3OH/CHCl_3$, 2:2:1 $CHCl_3/CH_3OH/i$-$PrNH_2$ and 2:2:1:1 $CHCl_3/CH_3OH/i$-$PrNH_2/H_2O$. After evaporation of the eluent solvent, the precipitated silica was filtered off and washed thoroughly with 1:1 $CH_3OH/CHCl_3$. The desired product was obtained as a clear foam, 0.25 g (56%). CI-MS ($C_{29}H_{53}N_9O_4$: m/z 592 (M+1)$^+$; NMR: δ0.53 (3H, t, J=7.4 Hz), 4.15 (1H, t, J=7.5 Hz), 6.37 (2H, d, J=8.2 Hz), 6.71(2H, d, J=8.2 Hz).

Moiety C (i) N-decanoyl-O-benzyl-L-tyrosine-p-nitrophenol ester

To a solution of 1.5 g (3.05 mmol) of N-BOC-O-benzyl-L-tyrosine-p-nitrophenol in 15 mL of $CHCl_3$ was added 8 mL of TFA and this mixture was stirred at room temperature. After roughly 2 hours when all of the starting material was consumed according to TLC (silica, 35% EtOAc/hexane), the solution was evaporated to dryness. The resulting solid was suspended in 15 mL of $CHCl_3$ with stirring and to this suspension was added simultaneously 0.697 g (3.66 mmol) of decanoyl chloride and 1.27 mL (9.15 mmol) of $Et_3N$. The slightly yellow solution was stirred at room temperature. After 90 minutes the solution was evaporated to a slightly yellow solid and recrystallized with EtOH or chromatographed on silica with $CHCl_3$ yielding 1.48 g (89%) of the desired product. NMR: δ0.87 (3H, t, J=7.7 Hz), 2.22 (2H, t, J=7.8 Hz), 3.20 (2H, d, J=6.8 Hz), 5.01 (1H, t, J=6.8 Hz), 5.06 (2H, s), 6.96 (2H, d, J=8.1 Hz), 7.12 (2H, d, J=8.1 Hz), 7.17 (2H, d, J=8.1 Hz), 7.41 (5H, complex), 8.24 (2H, d, J=8.1 Hz).

(ii) N-decanoyl-O-benzyl-L-tyrosine-spermine-amide and Bis-spermine-amide

To a 10 mL $CH_3OH$ solution of 1.45 g (2.38 mmol) of N-decanoyl-O-benzyl-L-tyrosine-p-nitrophenol ester was added dropwise a 10 mL $CH_3OH$ solution of 0.58 g (2.85 mmol) of spermine with stirring at room temperature. After 1 hour, the reaction mixture was concentrated to a yellow, semi-crystalline oil and 10 mL of $CHCl_3/CH_3OH$ (1:1) was added to enhance crystallization of the p-nitrophenol. This suspension was filtered through celite and washed with 10 mL of $CHCl_3/CH_3OH$ (1:1) solution. The filtrate was concentrated to a clear yellow oil and then chromatographed on 25 g of silica with a step gradient of 9:1 $CHCl_3/CH_3OH$ and 15:5:1 $CHCl_3/CH_3OH/i$-$PrNH_2$, eluting the "Bis" adduct 0.322 g (27%). NMR: δ0.70 (6H, t, J=6.5 Hz), 1.98 (4H, t, J=6.5 Hz), 4.29 (2H, t, J=8.0 Hz), 4.85 (4H, s), 6.73 (4H, d, J=8.7 Hz), 6.95 (4h, d, J=8.7 Hz), 7.16 (10H, complex). The column elution was continued with 4:4:1 $CHCl_3/CH_3OH/i$-$PrNH_2$ which yielded 0.322 g (58%) of a clear, light yellow oil. NMR: δ0.70 (3H, t, J=5.2 Hz), 1.97 (2H, t, J=7.3 Hz), 4.30 (1H, t, J=7.2 Hz), 4.86 (2H, s), 6.72 (2H, d, J=8.7 Hz), 6.97 (2H, d, J=8.7 Hz), 7.18 (5H, complex).

(iii) C10-PhTX-343(compound 20)

To a 2mL $CH_3OH$ solution containing 0.055 g (0.090 mmol) of N-decanoyl-O-benzyl-L-tyrosine-spermine-amide was added roughly 0.02 g of 5% Pd/C. This solution was purged several times with hydrogen and then stirred for 12 hours. The reaction was terminated by filtration through celite and careful washing of the carbon with copious volumes of $CH_3OH$. After evaporation of the solvent, the clear oil was chromatographed on 10 g of silica with 10:1 $CHCl_3/CH_3OH$ and 4:4:1 $CHCl_3/CH_3OH/i$-$PrNH_2$. The desired product, 0.26 g (55%) was obtained as a clear oil. CI-MS ($C_{29}H_{53}N_5O_3$): m/z 520 (M+1)$^+$; NMR: δ0.70 (3H, t, J=6.6 Hz), 2.97 (2H, t, J=6.3 Hz), 4.26 (1H, t, J=7.6 Hz), 6.48 (2H, d, J=7.9 Hz), 6.83 (2H, d, J=7.9 Hz).

(iv) Bis-C10-PhTX-343(compound 45)

A 3 mL $CH_3OH$ solution of 0.110 g (0.108 mmol) Bis-spermineamide was treated in the same manner as for the above synthesis of PhTX-343 above with roughly 0.05 g of 5% Pd/C. The product was purified on a silica flash column with 15:5:1 $CHCl_3/CH_3OH/i$-$PrNH_2$. yielding 0.072 g (80%) of the desired product. CI-Ms ($C_{48}H_{80}N_6O_6$): m/z 859(M+Na)$^+$, 837 (M+1)+1; NMR: δ0.67 (6H, t, J=6.9 Hz), 2.97 (4H, br t, J=6.3 Hz), 4.21 (2H, t, J=7.6 Hz), 6.48 (4H, d, J=8.4 Hz), 6.82 (4H, d, J=8.4 Hz).

Moiety B (i) N-butyryl-L-glycine-p-nitrophenol

To a solution of N-BOC-L-glycine-p-nitrophenol ester (Sigma), 0.25 g (0.834 mmol) in 3 mL of $CHCl_3$ was added 2 mL of TFA at room temperature with stirring. This solution was stirred for 30 minutes before the solvent was evaporated. The white powder was suspended in 3 mL of $CHCl_3$ and to this solution was added simultaneously 0.35 mL (2.5 mmol) of $Et_3N$ and 0.10 mL (1.00 mmol) of butyryl chloride. This solution was stirred for 30 minutes before evaporation of the solvent and loading of the crude oil onto a silica flash column from which the pure product was eluted with $CHCl_3$ in 85% yield (0.188 g), NMR ($CDCl_3$): δ1.54 (3H, t, J=7.4 Hz), 2.25 (2H, m), 2.82 (2H, t, J=7.5 Hz), 4.78 (2H, s) 7.95 (2H, d, J=9.6 Hz), 8.84 (2H, d, J=9.6 Hz).

(ii) N-butyryl-L-glycine-spermine-amide (compound 16)

To a 7 mL $CH_3OH$ solution of spermine 0.171 g (0.848 mmol) was added dropwise a 7 mL $CH_3OH$ solution of N-butyryl-L-glycine-p-nitrophenol ester 0.188 g (0.71 mmol) with stirring at room temperature. This mixture was stirred for 30 minutes before evaporation of the solvent to a yellow, semi-crystalline oil. Roughly 10 mL of $CHCl_3/CH_3OH$ (1:1) was added to enhance crystallization of the p-nitrophenol. This suspension was filtered and washed through celite with 10 mL of $CHCl_3/CH_3OH$ (1:1) solution. The filtrate was evaporated to a clear yellow oil nd then chromatographed on 6.8 g of silica with a step gradient system of 9:1 $CHCl_3/CH_3OH$, 15:5:1 $CHCl_3/CH_3OH/i$-$PrNH_2$ and 4:4:1 $CHCl_3/CH_3OH/i$-$PrNH_2$ yielding 0.118 g (51%) of a clear, light yellow oil. FAB-MS ($C_{16}H_{35}N_5O_2$): m/z 352 (M+Na)$^+$, 330 (M+1)$^+$; NMR: δ0.90 (3H, t, J=7.4 Hz), 2.17 (2H, t, J=7.5 Hz), 3.74 (2H, s).

Moiety A (i) PhTX-43 (compound 4)

The corresponding O-benzyl-tyrosyl-amine was deprotected in the same manner as for PhTX-343 in 89% yield from 0.189 g of starting material. CI-MS ($C_{20}H_{34}N_4O_3$): m/z 379 (M+1)$^+$; NMR: δ0.64 (3H, t, J=7.4 Hz), 1.94 (2H, t, J=7.6 Hz), 4.26 (1H, t, J=7.6 Hz), 6.47 (2H, d, J=8.4 Hz), 6.82 (2H, d, J=8.4 Hz).

(ii) PhTX-4 (compound 5)

The corresponding O-benzyl-tyrosyl-amine, 0.220 g (0.535 mmol) was deprotected in the same manner as above in 88% yield. CI-MS ($C_{17}H_{27}N_3O_3$): m/z 322 (M+1)$^+$; NMR: δ0.66 (3H, t, J=7.5 Hz), 1.96 (2H, t, J=7.5 Hz), 4.28 (1H, t, J=7.5 Hz), 6.49 (2H, d, J=8.5 Hz), 6.84 (2H, d, J=8.5 Hz).

(iii) PhTX-0 (compound 6)

To a stirred solution of $NH_4OAc$ 0.166 g (2.16 mmol) in 2 mL of DMF was added 0.200 g (0.433 mmol) of N-butyryl-O-benzyl-tyrosine-p-nitrophenol ester dissolved in 3 mL of DMF; this mixture was stirred for 5 minutes before terminating the reaction by pouring it into 0.1 N NaOH aq. and extracting with EtOAC. The combined organic extracts were washed with brine and dried over $MgSO_4$ before evaporation of the solvent and elution from a silica flash column with 2% $CH_3OH/CHCl_3$ yielding 0.129 g (88%) of pure product. This clear oil was then dissolved in 15 mL of $CH_3OH$ and treated with 0.130 g of 5% Pd/C and hydrogen for 1 hour. The reaction mixture was purified first by filtration and washing through celite, followed by evaporation of the solvent and recrystallization from 1:2 $CH_3OH/CHCl_3$, yielding 0.036 g (38%) of pure product. The mother liquid was reevaporated and recrystallized from the 1:1:2 $CH_3OH/Et_2O/CHCl_3$ to give another 0.02 g, a total yield of 50%. CI-MS ($C_{13}H_{18}N_2O_3$): m/z 251 (M+1)$^+$; NMR: δ0.64 (3H, t, J=7.4 Hz), 1.33 (2H, m), 1.94 (2H, t, J=7.6 Hz), 2.58 (1H, dd, J=13.9, 9.0 Hz), 2.86 (1H, dd, J=13.9, 5.7 Hz), 4.37 (1H, dd, J=9.0, 5.7 Hz), 6.50 (2H, d, J=8.4 Hz), 6.87 (2H, d, J=8.4 Hz).

(iv) N-[2-(1-(butyl)cyanoethyl)]-butane-1,4-diamine

To a 10 mL dry THF solution at −78° C. of 0.44 g (3.15 mmol) of 2-(diaminobutyl)-ethylnitrile, was added 1.38 mL of 2.5 molar n-butyl lithium in hexane (Aldrich) (3.45 mmol) and this mixture was stirred for 5 minutes. To this suspension was added dropwise 0.33 mL of 1-bromobutane (3.1 mmol) and then the reaction temperature was raised to 0° C. After stirring for another 5 minutes, the reaction temperature was allowed to rise to room temperature. After quenching by addition of $H_2O$, the solvent was evaporated and the residue suspended in water was extracted 3 times with $CHCl_3$. The combined organic layers were washed with brine, dried over $MgSO_4$, and then evaporated to yield a mixture of mono- and di-alkylation products (ca 1:1) in 746 yield. This mixture was purified on silica gel with 10% $CH_3OH$ in $CHCl_3$. NMR ($CDCl_3$): δ0.95 (3H, t, J=6 Hz), 1.1–1.7 (11H, complex), 2.6–3.9 (5H, complex), 3.75 (1H, t, J=6.3 Hz).

(v) PhTX-(butyl)433 (compound 8)

N-butyryl-O-benzyl-L-tryrosyl-butyl-thermospermine-433 was deprotected in the same manner as for PhTX-343 yielding 0.081 g (28%) of pure product. FAB-MS ($C_{27}H_{49}N_5O_3$): m/z 492 (M+1)$^+$; NMR: δ0.84 (3H, t, J=7.5 Hz), 0.87 (3H, t, J=5.9 Hz), 2.14 (4H, t, J=7.7 Hz), 4.44 (1H, t, J=7.)Hz), 6.72 (2H d, J=8.4 Hz), 7.00 (2H, d, J=8. Hz)

Method B (i) N-CBZ-L-tyrosyl-spermine-amide

To a 3 mL DMF solution of 0.56 g (2.75 mmol) of spermine was added dropwise a 3 mL DMF solution of 1.0 g (2.29 mmol) of N-CBZ-L-tyrosine p-nitrophenol ester resulting in the instant formation of a bright yellow color. After completion of the ester addition, the solution was stirred for another 30 min. The desired product was obtained by evaporating the solvent, adding 20 mL of $CHCl_3$ and evaporating again. The bright yellow oily suspension was suspended in 10 mL of $CH_3OH/CHCl_3$ (1:1) and filtered through celite followed by rinsing with the same solution. Upon evaporation of the clear yellow solution, the yellowish crude oil was purified on 15 g of silica eluting the desired product with a gradient of 9:1 $CHCl_3/CH_3OH$, 15:5:1 $CHCl_3/CH_3OH/i-PrNH_2$, and 4:4:1 $CHCl_3/CH_3OH/i-PrNH_2$ This purification yielded 0.58 g (51%) of the desired product. FAB-MS ($C_{27}H_{41}N_5O_4$): m/z 500 (M+1)$^+$; NMR: δ4.21 (H, br, s) 5.02 (2H, s), 6.67 (2H, d, J=8.4 Hz), 6.96 (2H, d, J=8.4 Hz), 7.25 (5H, s).

(ii) N-CBZ-L-tyrosyl-spermine-Nα, Nε-di-BOC-L-lysine-diamide

To a 5 mL DMF solution of 0.62 g (1.2 mmol) of N-CBZ-L-tyrosyl spermine amide was added dropwise a 5 mL DMF solution of 0.39 g (1.2 mmol) of Nα, Nε-di-BOC-L-lysine p-nitrophenol ester. This solution was stirred at room temperature for 30 minutes. The reaction was worked up by evaporation of DMF under high vacuum followed by addition of 6 mL of $CH_3OH/CHCl_3$ (1:1); this suspension was filtered and washed through celite with the same (1:1) solution. The clear yellow oil obtained after filtration and evaporation of the solvent was chromatographed on 32 g of silica and eluted with 9:1 $CHCl_3/CH_3OH$ and 15:5:1 $CHCl_3/CH_3OH/i-PrNH_2$ by which 0.59 g (71%) of the desired product was obtained as a white foam. FAB-MS ($C_{43}H_{69}N_7O_9$): m/z 828(M+1)$^+$; NMR: δ1.33 (18H, s), 3.84 (1H, dd, J=8.1, 4.7 Hz), 4.12 (1H, t, J=7.5 Hz), 4.88 (1H, d, J=13.0 Hz), 4.97 (1H, d, J=13.0 Hz), 6.59 (2H, d, J=8.2 Hz), 7.03 (2H, d, J=8.2 Hz), 7.30 (5H, m).

(iii) N-CBZ-O-BOC-L-tyrosyl-di-BOC-spermine-Nα,Nε-di-BOC-L-lysine-diamide

To a 10 mL $CH_3OH$ solution containing 0.59 g (0.88 mmol) of the above diamide was added 0.81 mL (3.51 mmol) of BOC anhydride and 0.07 mL (0.88 mmol) of pyridine, and this mixture was stirred at room temperature for 12 hr. the clear oil was purified by evaporation of the solvent and by elution from 10.5 g of silica with 2% $CH_3OH/CHCl_3$. The resulting product was obtained as a clear oil in 82% yield, (0.08 g). NMR: δ1.38 and 1.45 (each s, total 45H), 3.87 (1H, br m), 4.24 (1H, br m), 4.92 (1H, d, J=12 Hz), 5.00 (1H, d, J=12 Hz), 6.95 (2H, d, J=8.6 Hz), 7.18 (2H, d, J=8.6 Hz), 7.20 (5H, m).

(iv) O-BOC-L-tyrosyl-di-BOC-spermine-Nα,Nε-di-BOC-L-lysine-diamide

In a 10 mL of $CH_3OH$, 0.48 g (0.44 mmol) of the above N-CBZ-O-BOC-diamide was dissolved and roughly 0.150 g of 5% Pd/C was added. This suspension was stirred under hydrogen atmosphere at room temperature for 12 hr. The reaction was worked up by filtration through celite and washing with copious volumes of $CH_3OH$. The filtrate was concentrated leaving a clear oil which was chromatographed on silica with a 1 to 5% $CH_3OH/CHCl_3$ step gradient. The desired product was obtained in pure form weighing 0.32 g (77%). NMR: δ1.35 and 1.41 (each s, total 45H), 3.86 (2H, br m), 6.98 (2H, d, J=8.5 Hz), 7.17 (2H, d, J=8.5 Hz).

(v) N-(ρ-azidobenzamide)-O-BOC-L-tyrosyl-di-2',3'-N, N-BOC-spermine-Nα,Nε-di-BOC-L-lysine-triamide In 6 mL of DMF containing 0.32 g (0.34 mmol) of the above-per-BOC-diamide was added with stirring 0.06 g (0.37 mmol) of p-azidobenzoic acid and 0.08 mL (0.37 mmol) of diphenylphosphoryl azide. Finally, 0.08 mL (0.37 mmol) of $Et_3N$ was added and this mixture was stirred overnight. The reaction was worked up by pouring the reaction mixture into 15 mL of water and extracting 3 times with EtOAc. The combined organic layers were washed twice with brine and dried over $MgSO_4$. After evaporation of the solvent, the crude oil was chromatographed on silica with $CHCl_3$ followed by 2.55 $CH_3OH/CHCl_3$. The product was obtained in 69% yield (0.25 g). NMR: δ1.37 and 1.44 (each s, total 45H), 3.88 (1H, br s), 4.68 (1H, br s), 6.96 (2H, d, J=8.6 Hz), 7.05 (2H, d, J=8.6 Hz), 7.24 (2H, d, J=8.6 Hz), 7.75 (2H, d, J=8.6 Hz).

(vi) N-(p-azidobenzamide)-L-tyrosyl-spermine-L-lysine-triamide (compound 40)

BOC deprotection of the above per-BOC-azido-triamide, 0.12 g (0.129 mmol) was effected in 4 mL $CHCl_3$ with 3 mL of TFA for 1 hour at room temperature with stirring. After 3 repetitive evaporations of $CHCl_3$, the crude oil was chromatographed on silica with 15:5:1 $CHCl_3/CH_3OH/i-PrNH_2$, and 5:5:1 $CHCl_3/CH_3OH/i-PrNH_2$. The desired product was obtained in 70% yield. FAB-MS ($C_{32}H_{50}N_{10}O_4$): m/z 661 (M+Na)$^+$, 639 (M+1)$^+$; NMR (TFA salt): δ3.58 (1H, t, J=7.6 Hz), 4.28 (1H, t, J=7.6 Hz), 6.43 (2H, d, J=8.6 Hz), 6.80 (2H, d, J=8.6 Hz), 6.84 (2H, d, J=8.6 Hz), 7.53 (2H, d, J=8.6 Hz).

(vii) N-(ρ-azidobenzamide)-di-iodo-L-tyrosyl-spermine-L-lysine-triamide (compound 42)

To a 1.3 mL solution $H_2O/CH_3OH$ (5:1) containing 27.4 mg (0.025 mmol) of 40, 10.8 mg (0.065 mmol) of KI, and 17.4 mg (0.10 mmol) of K$_2$HP$_4$ was added dropwise by pipette with rapid stirring 9.8 mg (0.065 mmol) of N-bromo succinimide dissolved in 1 mL of CH$_3$OH/H$_2$O (1:1). All solutions were degassed with argon. The reaction mixture was stirred for 30 minutes and then lyophilized to dryness. The brownish powder was loaded onto a silica pipette column and eluted with 15:5:1 CHCl$_3$/CH$_3$OH/i-PrNH$_2$, and 4:4:1 CHCl$_3$/CH$_3$OH/i-PrNH$_2$. FAB-MS (C$_{32}$H$_{48}$N$_{10}$O$_4$I$_2$): m/z 891 (M+1)$^+$; NMR (D$_2$O, TFA salt): δ3.72 (1H, br, s), 4.38 (1H, br s), 6.98 (2H, d, J=7.5 Hz), 7.52 (2H, s), 7.70 (2H, d, J=7.5 Hz).

Alternate Method

Heptanoylspermine-amide (compound 48) and Bis-heptanoylspermine-amide (compound 51)

To a solution of 0.126 g (0.50 mmol) of p-nitrophenol heptanoate in 3.0 mL of CH$_3$OH was added a 3 mL CH$_3$OH solution of 0.145 g (0.717 mmol) of spermine. This solution was stirred at room temperature for 2 hr before evaporation of solvent, followed by filtration and washing of the cloudy, yellow suspension through celite with 1:1 CH$_3$OH/CHCl$_3$. The resulting filtrate was evaporated and the clear yellow oil loaded onto a silica flash column from which was eluted first a mixture of p-nitrophenol and the "Bis" product, 51, with 15:5:1 CHCl$_3$/CH$_3$OH/i-PrNH$_2$. A CHCl$_3$ solution of the impure "Bis" product was washed with sat. NaHCO$_3$ and brine, dried over MgSO$_4$ before evaporation and re-elution of 20 mg (19%) of pure "Bis" product from a second silica flash column with 3:1:0 and 4:4:1 CHCl$_3$/CH$_3$OH/i-PrNH$_2$. CI-MS (C$_{24}$H$_{50}$N$_4$O$_2$): m/z 427 (M+1)$^+$; NMR: δ0.72 (6H, t, J=6.8 Hz), 1.112 (10H, br s), 1.43 (12H, complex), 1.98 (4H, t, J=7.7 Hz), 2.40 (8H, m), 3.03 (4H, t, J=6.8 Hz). The original flash column elution was continued with 4:4; 1 and 1:1:1 CHCl$_3$/CH$_3$OH/i-PrNH$_2$ yielding pure mono-acylated product 48, 0.099 g (63%). CI-MS (C$_{17}$H$_{38}$N$_4$O): m/z 315 (M+1)$^+$; NMR: δ0.73 (3H, t, J=6.8 Hz), 1.13 (8H, br s), 1.3–1.6 (10H, complex), 1.99 (2H, t, J=7.6 Hz), 2.3–2.6 (4H, complex), 3.04 (2H, t, J=6.8 Hz).

Synthesis of 7', O-Benzyl-L-tyrosine methyl ester (1'). To 10 ml of cold methanol, 0.465 ml of thionyl chloride was added dropwise, followed by 1.0523 g of tyrosine. After stirring at 4° C. for 2 hr, reaction was terminated by evaporating solvents. Water (20 ml) was added to dissolve the residue; i-PrNH$_2$ was added to neutralize the aqueous solution. After extracting with ether (3×20 ml), organic layers were combined and dried over MgSO$_4$. Filtration and concentration in vacuo provided the expected product. NMR: δ(CDCl$_3$): 7.3–7.45 (m, 5H), 6.85–7.15 (m, 4H), 5.3 (s, 1H), 5.0 (s, 2H), 3.7 (s, 3H), 2.8–3.1 (m, 2H), 1.65 (br s, 2H).

O-Benzyl-butyl amine-tyrosine methyl ester (2'). To an acetonitrile solution of 1' (0.7918 g) was added 0.54 g KF/celite. Butyl bromide (0.149 ml) was injected under an argon atmosphere. The mixture was refluxed for 4 hr, filtered through celite, concentrated, and then the residue was subjected to column chromatography to afford pure 2'. NMR: δ(CDCl$_3$): 7.3–7.5 (m, 5H), 6.9–7.1 (m, 4H), 5.05 (s, 2H), 3.6 (s, 3H), 3.5 (t, 1H), 2.9 (m, 2H), 24–3.6 (m, 2H), 1.4 (m, 3H), 1.3 (m, 2H), 0.9 (t, 3H).

O-Benzyl-Boc-butyl amine-tyrosine methyl ester (3'). To dichloromethane solution of 2' (98 mg) was added 150.1 mg (Boc)$_2$O. The mixture was stirred for 8 hr under Ar and then concentrated. The residue was subjected to column chromatography to afford pure 3'. NMR: δ(CDCl$_3$): 7.3–7.5 (m, 5H), 6.9–7.1 (m, 4H), 5.05 (s, 2H), 3.7 (s, 3H), 3.0–3.3 (m, 3H), 2.5–2.7 (m, 1H), 1.45 (s, 9H), 1.3 (m, 2H), 1.2 (m, 2H), 0.85 (t, 3H).

O-Benzyl-Boc-butyl amine-tyrosine alcohol (4'). To a dichloromethane solution of 3' (0.5749 g) at 0° C. under Ar was added excess DIBAL. After stirring for 1 hr, the reaction was quenched with 1N HCl, and then extracted by with CH$_2$Cl$_2$(3×). The organic layers were combined, washed with sat'd NaCl and concentrated to provide a crude product suitable for use in the next step. NMR: δ(CDCl$_3$): 7.3–7.5 (m, 5H), 6.9–7.1 (m, 4H), 5.05 (s, 2H), 3.5–3.8 (m, 4H), 2.7–3.1 (m, 4H), 1.45 (s, 9H), 1.2–1.4 (m, 4H), 0.9 (t, 3H).

O-Benzyl-Boc-butyl amine-tyrosine aldehyde (5'). To a solution of oxalyl chloride (9.8 ml) in 5 ml CH$_2$Cl$_2$ in a 25 ml round-bottom flask under Ar was added DMSO (15 ml) at –50° C. The mixture was stirred for a few minutes, then the alcohol (50.8 mg) in CH$_2$Cl$_2$ was added dropwise in 5 min. The mixture was stirred for 15 min. Et$_3$N was then added, and the mixture was stirred for another 5 min. After warming to room temperature, water (10 ml) was added. The mixture was extracted with CH$_2$Cl$_2$ and the organic layer was concentrated to provide the expected product. NMR: δ(CDCl$_3$) 9.6 (d, 1H), 7.3–7.5 (m, 5H), 6.9–7.1 (m, 4H, 5.05 (s, 2H), 2.9–3.6 (mm, 4H), 2.3–2.4 (m, 1H), 1.45 (ds, 9H), 1.2–1.4 (mm, 4H), 0.9 (t, 3H).

O-Benzyl-Boc-PhTX-C$_4$-amine -343 (6'). To an ethanolic solution of 5' (100 mg) and spermine (123 mg) was added 341 mg of Na$_2$SO$_4$. After stirring for 48 hr under Ar, the mixture was filtered through glass wool. NaBH$_4$ (92 mg) was added to the filtrate. After stirring for 24 hr, 2 ml of H$_2$O was added quench the reaction. EtOH was removed by rotary evaporation. The residue was extracted by CH$_2$Cl$_2$ (3×). The organic layers were combined and dried over Mg$_2$SO$_4$. After concentrating, the residue was subject to column chromatography to afford a pure product. NMR: δ(CDCl$_3$): 7.3–7.4 (m, 5H), 6.8–7.1 (m, 4H), 5.0 (s, 2H), 2.5–3.0 (mm, 22H), 1.65 (m, 4H), 1.5 (m, 4H), 1.4 (s, 9H), 1.2 (m, 4H), 0.85 (m, 3H).

O-Benzyl-PhTX-C$_4$-amine -343 (7'). To a dichloromethane solution of 6' was added TFA. After stirring for 30 min, the mixture was concentrated to provide a reaction product sufficiently pure for subsequent use. NMR: δ(CDCl$_3$): 7.3–7.5 (m, 5H), 6.9–7.25 (m, 4H), 5.1 (s, 2H), 4.95 (s), 3.3 (s, 2H), 2.75–3.25 (mm, 12H), 2.0–2.2 (m, 2H), 1.8 (m , 3H), 1.65 (m, 4H), 1.45 (m, 10H), 1.3 (d, 2H), 0.95 (m, 3H). MS: FAB (M+H)$^+$499

Synthesis of C10-Trp-343 (10'). N-Boc-L-tryptophan p-nitrophenyl ester (8'): This compound was prepared as described above for N-Boc-L-tyrosine p-nitrophenyl ester.
N-Decanoyl-L-tryptophan p-nitrophenyl ester (9'): This compound as described for the corresponding tyrosine ester N-butyramide. Butyryl chloride and N-Boc-O-benzyl-L-tyrosine p-nitrophenyl ester were replaced by decanoyl chloride and N-Boc-L-tryptophan p-nitrophenyl ester, respectively. NMR: δ(CDCl$_3$): 8.2 (d, 2H), 7.6 (d, 1H), 7.0–7.4 (m, 6H), 6.0 (d, 1H), 5.1 (q, 1H), 3.45 (t, 2H), 2.2 (t, 2H), 1.2 (s, 14H), 0.9 (t, 3H)

C10-Trp-343 (10').

To a 10 ml MeOH solution of 1.1 g (2.3 mmole) of N-decanoyl-L-tryptophan p-nitrophenyl ester 9' was added dropwise a 10 ml MeOH solution of 0.65 g (3.2 mmole, 1.4 equivalents of spermine with stirring at room temperature. After 3 hr, the reaction mixture was concentrated to yellow oil and 10 ml of MeOH/CH$_2$Cl$_2$ (1:1) was added to enhance crystallization of p-nitrophenol. The resulting suspension was filtered and washed through Celite with 10 ml of the same solution. The filtrate was concentrated to a clear yellow oil and then purified by silica gel flash column chromatography using a step gradient of CH$_2$Cl$_2$/MeOH (9:1) and CH$_2$Cl$_2$/MeOH/i-PrNH$_2$ (15:5:1) eluting bis[N-decanoyl-L-tryptophan] spermine di-amide. The column elution was continued with CH$_2$Cl$_2$/MeOH/i-PrNH$_2$ (4:4:1) which yielded 0.62 g (52%) of N-decanoyl-tryptophan spermine amide as a light yellow oil. DCI-MS (NH$_3$, C$_{31}$H$_{54}$N$_6$O$_2$): m/z 543 (M+1)$^+$; $^1$H-NMR (250 MHz, CD$_3$OD) δ7.45–7.40 (d, J=7.5 Hz, 1H), 7.18–7.12 (d, J=7.5 Hz, 1H), 6.95–6.80 (m, 3H), 4.46–4.42 (t, J=7.2 Hz, 1H), 3.2–2.85 (m, 4H), 2.7–2.2 (m, 10H), 2.10–2.05 (t, J=7.0 Hz, 2H), 1.6–0.9 (m, 22H), 0.80–0.75 (t, J=7.0 Hz, 3H).

Polyamine-3×3 (Boc)$_2$ (11'). 0.40 g (2.3 mmole) of mono N-Boc protected 1,3-diaminopropane in 7 ml EtOH was added to a suspension of 154 mg (1.15 mmole) p-terphthaldehyde and 0.3 mg molecular sieves 3Å in 3 ml EtOH while stirring at room temperature. The reaction mixture immediately turned colorless. After stirring for 3 hr, a fresh NaBH$_4$ (350 mg) suspension in 10 ml EtOH was added to the previous reaction mixture, and the reduction allowed to proceed for 4 hr at room temperature. To quench the reaction, 5 ml of water was carefully added to the mixture. After stirring was continued for 1 hr, the precipitate was filtered through a pad of celite. The filter plug was washed with MeOH (5 ml); the filtrate was evaporated in vacuo, affording an opaque oily material. The crude product was pure enough by TLC (R$_f$=0.65 in 8:4:1 CH$_2$Cl$_2$/MeOH/i-PrNH$_2$) and NMR analysis for the next step, and was used without further purification.

Polyamine-3×3 (12'). 437 mg of polyamine-3×3 (Boc)$_2$ was dissolved in 9 ml of TFA/CH$_2$Cl$_2$ (1:2). The solution was stirred for 6 hr at room temperature. The solvent was completely removed in vacuo to afford the expected product as an oily material in quantitative yield. After dissolving the residue in de-ionized water, and freezing, the frozen solid was lyophilized to provide a solid product. FAB-MS (3-nitrobenzyl alcohol matrix, C$_{14}$H$_{26}$N$_4$): m/z 251 (M+1)$^+$.

PhTX-3×3 (13'). To a stirred suspension of 137 mg (0.37 mmole) N-butyryl-L-tyrosine p-nitrophenyl ester in 5 ml MeOH was added 5 ml MeOH solution of 260 mg (0.37 mmole) of polyamine-3×3 TFA salt and 59 mg (1.5 mmole) of NaOH. The reaction mixture was stirred for 12 hr at room temperature. MeOH was evaporated to yield an yellow oily residue. The crude product was purified by silica gel flash chromatography using 16:4:1 CH$_2$Cl$_2$/MeOH/i-PrNH$_2$. The product was obtained as a pale yellow amorphous powder or oil in 45% yield (80 mg). FAB-MS (3-nitrobenzyl alcohol matrix, C$_{27}$H$_{41}$N$_5$O$_3$): m/z 484 (M+1)$^+$; $^1$H-NMR (400 MHz, CD$_3$OD δ7.30 (C$_6$H$_4$; s, 4H), 7.03–7.01 (d, J=8.8 Hz, 2H), 6.70–6.67 (d, J=8.8 Hz, 2H), 4.46–4.43 (HNCHCO; t, J=8.4 Hz, 1H), 3.70–3.68 (HNCH$_2$Ph; ds, 4H), 3.22–3.10 (CONHCH$_2$; m, 2H), 2.93–2.88 (NHCHCH$_2$Ar; dd, J=7.2 Hz, 13.6 Hz, 1H), 2.76–2.71 (t, J=7.2 Hz, 2H), 2.68–2.57 (t, J=7.2 Hz, 2H), 2.48–2.45 (t, J=7.2 Hz, 2H), 2.15–2.11 (COCH$_2$CH$_2$; t, J=7.6 Hz, 2H), 1.73–1.71 (quintet, J=7.2 Hz, 2H), 1.70–1.57 (quintet, J=7.2 Hz, 2H), 1.55–1.48 (COCH$_2$CH$_2$; sextet, J=7.6 Hz, 2H), 0.85–0.81 (COCH$_2$CH$_2$CH$_3$; t, J=7.6 Hz, 3H).

Synthesis of 23'. N-Cyanoethyl-1,4-diaminobutane (14'). To a methanol solution (containing 10 ml MeOH) of 1,4-diaminobutane (3 ml) was added acrylnitrile by syringe pump over 5 hr. The mixture was stirred overnight, and then concentrated in vacuo. The residue was purified by column chromatography.

Di-Boc-N-cyanoethyl-1,4-diaminebutane (15'). To a solution of 1.5983 g of 14' in 10 ml CH$_2$Cl$_2$ was added excess (Boc)$_2$O. After stirring overnight, the reaction mixture was concentrated in vacuo. The residue was subjected to column chromatography to afford the desired product.

Di-Boc-4,3-amine (16'). A solution of 0.6340 g of 15' in 10 ml of glacial acetic acid was hydrogenated over Pd(OH)$_2$ at 50 psi hydrogen pressure for 2 hr. The catalyst was removed by filtration through celite. Evaporation of the solvent gave crude product which was dissolved in 50 ml of CH$_2$Cl$_2$, washed with 1 N NaOH (2×) and dried over Na$_2$SO$_4$. The solution was concentrated and subjected to column chromatography to afford the desired product.

Cyanoethyl-di-Boc-4,3-amine (17'). To 10 ml of MeOH of 0.5366g of 16' was added acrylnitrile by syringe under Ar. After stirring for 8 hr, the reaction mixture was concentrated and subjected to column chromatography to afford the expected product. NMR: δ(CDCl$_3$): 4.6 (br s, 1H), 3.5 (t, 2H), 3.25 (t, 2H), 3.15 (m, 8), 2.6 (m, 2H), 1.75 (m, 2H), 1.45 (m, 29H).

Cyanoethyl-tri-Boc-4,3-amine (18'). The same general procedure followed to prepare compound 15' was used to prepare compound 18'. NMR: δ(CDCl$_3$): 4.7 (br s, 1H), 3.0–3.3 (m, 12H), 2.7 (m, 2H), 2.2 (m, 2H), 1.7 (m, 4H), 1.4 (m, 32H).

Tri-Boc-4,3,3-amine (19'). The same general procedure followed to prepare compound 16' was used to prepare compound 19'.

Cyanoethyl-tri-Boc-4,3,3-amine (20'). The same general procedure followed to prepare compound 17' was used to prepare compound 20'. NMR: δ(CDCl$_3$): 4.6 (br s, 1H), 3.1–3.3 (m, 12H), 2.9 (t, 2H), 2.6 (m, 2H), 2.5 (t, 2H), 1.7 (m, 4H), 1.4 (m, 29H).

Tetra-Boc-4,3,3-amine (21'). The same general procedures followed to prepare compounds 15' and 16' were used to prepare compound 21'. NMR: δ(CDCl$_3$): 4.7 (br s, 1H), 3.1–3.3 (m, 14H), 2.7 (t, 2H), 1.7 (m, 8H), 1.4 (m, 40H). MS: M$^+$659

O-Benzyl-Boc-PhTX-C$_{10}$-amine-4333 (22'). To an ethanolic solution containing equivalent amounts of O-benzyl-Boc-decanoyl amine-tyrosine aldehyde and compound 21' was added excess solid anhydrous Na$_2$SO$_4$. After stirring for 36 hrs, the reaction mixture was filtered through a glass wool plug. Solid NaBH$_4$ was added, and the resulting suspension was stirred overnight. Aqueous work-up gave crude product suitable for use in the next step. NMR: δ(CDCl$_3$): 7.4 (m, 8H), 7.1 (m, 2H), 6.9 (d, 2H), 5.0 (s, 2H), 3.15 (m, 15H), ca. 2.7 (6H), 1.7 (m, 6H), 1.4 (s, 49H), 1.25(s, 16H), 0.9 (t, 3H). MS: (FAB) (M+H)$^+$1138

O-Benzyl-PhTX-C$_{10}$-amine-4333 (23'). To a dichloromethane solution of 22' was added neat TFA by syringe. After stirring for 1 hr, the mixture was concentrated and purified by column chromatography. NMR: δ(CHCl$_3$): 7.2–7.4 (m, 7H), 7.0 (d, 2H), 5.1 (s, 2H), 4.9 (s, 4H), 3.8 (m, 1H), 3.4 (dd, 1H), 3.3 (s, 7H) 2.9–3.2 (m, 10H), 2.1 (m, 6H), 1.6–1.6 (m, 6H), 1.3 (br s, 14H), 0.9 (t, 3H). MS: FAB: (M+H)$^+$640

Pharmacology

The retractor unguis muscle and its nerve were dissected from the metathoracic legs of adult, female locusts (*Schistoecerca gregaria*) and mounted in a Perspex perfusion chamber as described by Usherwood and Machili (21) and Bateman, et al. (14). The muscle was stretched to maximal body length and attached at its tendon or apodeme to a Grass FT 10-strain gauge by a short length of nylon thread. The volume of the muscle bath was about 0.5 ml and its contents could be exchanged within 1 sec. The preparation was perfused continuously at the rate of 5–10 ml min$^{-1}$ except during the application of toxin (see below) with standard locust saline of the following composition (mM): NaCl, 180; KCl, 10; CaCl$_2$, 2; Hepes, 10; buffered to pH 6.8. The retractor unguis muscle is innervated by two excitatory motoneurons (30) and an inhibitory motoneuron (19,32), but the influence of the latter on the responsiveness of the muscle is slight. Maximal stimulation of the retractor unguis nerve at 0.2 Hz produced a series of twitch contractions of constant amplitude, which were maintained for many hours in good preparations. The test compounds were kept at −20° C. They were dissolved in locust saline on the day of the assay and tested at room temperature. The compounds were applied by pipette to a nerve-muscle preparation such that the contents of the perfusion bath were completely replaced by the test solution. Exposure to the test compound lasted 20 min. Because of the limited availability of some of the compounds, the preparation was not perfused during this period. However, the amplitude of the retractor unguis muscle twitch rarely changed by more than 5–10% over a 20 minute period. During application of the test solutions the stimulation frequency was raised to 0.6 Hz for brief periods to test for stimulus frequency-dependent effects on twitch amplitude (31,37). Dose-inhibition data were obtained by testing the effects, on single retractor unguis muscle preparations, of a range of concentrations of the test compounds. Each concentration of the respective samples was tested at least thee times, and each compound was assayed usually over a 100-fold concentration range (a total of 7–10 concentrations). The standard deviations for twitch inhibition for any given concentration of a toxin rarely exceed 10%. Those compounds for which the deviation was greater than this are identified in Tables 1–7. There was some variation in the potency of PhTX-343 and the test compounds between nerve-muscle preparations. In order to compensate for this, the following procedure was adopted: PhTX-343 was assayed at a variety of concentrations on eight retractor unguis nerve-muscle preparations to give a cumulative dose-inhibition relationship for this toxin. The concentration of PhTX-343 which reduced the twitch contraction by 50% ($IC_{50}$) was then determined by fitting a curve to the data using the following equation:

$$I = \frac{I_{MAX}}{1 + (IC_{50}/[T])^{n'}}$$

where: [T]=toxin concentration, I=% inhibition, $I_{max}$= maximum inhibition=100% and n' represents the Hill slope coefficient. PhTX-343, at its $IC_{50}$ concentration ($2.3 \times 10^{-5}$ M) was then applied at an appropriate time during assay of each of the test compounds. The ratio of the actual reduction in twitch amplitude obtained with this single concentration of PhTX-343 and the 50% reduction that was anticipated from the cumulative dose-inhibition relationship for this toxin, was then used as a factor to normalize the data for the test compound. There were differences in the

TABLE 1

MODIFICATIONS TO REGION A OF PhTX-343 AND THE EFFECTS ON ANTAGONISM OF THE NEURALLY-EVOKED TWITCH CONTRACTION OF THE LOCUST (*Schistocerca gregaria*), METATHORACIC EXTENSOR TIBIAE MUSCLE

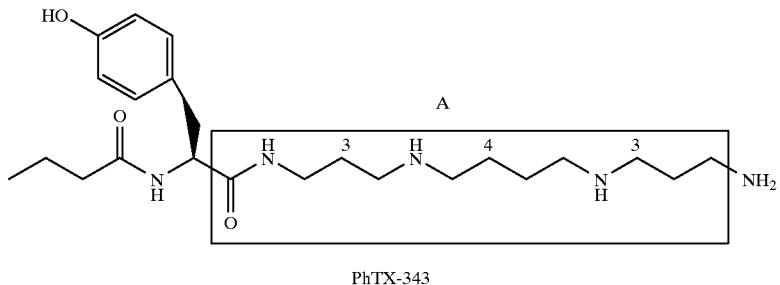

| Compound No. | | $IC_{50}$ (M) | Relative Potency |
|---|---|---|---|
| 1. | | $2.3 \times 10^{-5}$ | 1.0 |
| 2. | | $1.8 \times 10^{-5}$ | 1.3 |
| 3. | | $1.5 \times 10^{-5}$ | 1.5 |
| 4. | | $3.9 \times 10^{-5}$ | 0.6 |
| 5. | | $2.0 \times 10^{-3}$ | 0.01 |

TABLE 1-continued

MODIFICATIONS TO REGION A OF PhTX-343 AND THE EFFECTS ON ANTAGONISM OF THE NEURALLY-EVOKED TWITCH CONTRACTION OF THE LOCUST (*Schistocerca gregaria*), METATHORACIC EXTENSOR TIBIAE MUSCLE 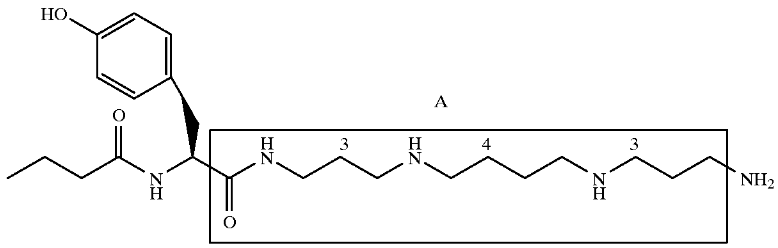 PhTX-343

| Compound No. | | $IC_{50}$ (M) | Relative Potency |
|---|---|---|---|
| 6. | 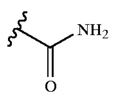  | $5.0 \times 10^{-4}$** | 0.05 |
| 7. | 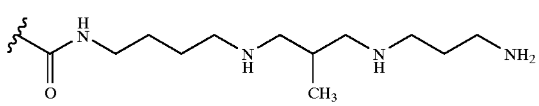  | $4.0 \times 10^{-5}$ | 0.6 |
| 8. | 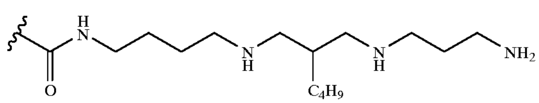  | $4.0 \times 10^{-6}$ | 5.6 |
| 9. | 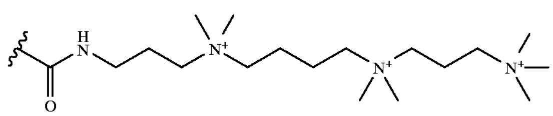  | $1.3 \times 10^{-4}$ | 0.2 |

**SD < 30%

Modifications In Region B (Table 2)

Removal of hydroxyl group in analog 10 increased potency about three-fold, whereas conversion of the tyrosyl analog to the 3,5-diiodo-tyrosyl analog 13 increased potency 4.5-fold (Table 2). The increased potency of analog 13 was especially useful since it allowed for radio-iodine labelling. It is conceivable that the iodine atoms are assisting in hydrophobic binding. However, it is difficult then to account for the unchanged potencies of the O-acetyl analog 11 and the O-benzyl analog 12. When the tyrosyl moiety was replaced by other amino acids, such as leucine analog 14 and alanine analog 15 the potency was either unchanged or slightly reduced, respectively. However, replacement by tryptophan as in analog 17 increased potency 10-fold: the tryptophan moiety may provide a subtle balance between hydrophilic (NH) and hydrophobic (aromatic) influences. The greatly reduced activity of the glycine analogs 16 suggests the necessity of an anchoring functionality in this region.

TABLE 2

EFFECTS OF MODIFICATIONS TO REGION B OF PhTX-343 ON ANTAGONISM OF LOCUST MUSCLE TWITCH CONTRACTION

| Compound No. | | $IC_{50}$ (M) | Relative Potency |
|---|---|---|---|
| 1. | 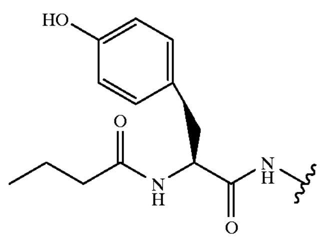  | $2.3 \times 10^{-5}$ | 1 |
| 10. | 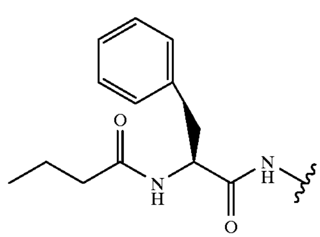  | $6.7 \times 10^{-6}$ | 3.4 |
| 11. | 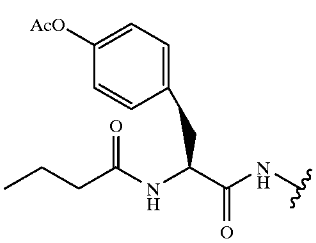  | $3.3 \times 10^{-5}$ | 0.7 |
| 12. | 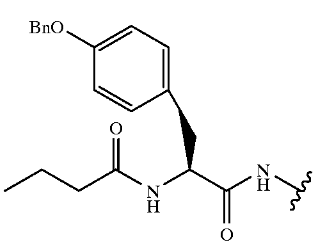  | $2.4 \times 10^{-5}$ | 1.0 |

TABLE 2-continued

EFFECTS OF MODIFICATIONS TO REGION B OF PhTX-343 ON ANTAGONISM OF LOCUST MUSCLE TWITCH CONTRACTION

| Compound No. | | $IC_{50}$ (M) | Relative Potency |
|---|---|---|---|
| 13. | 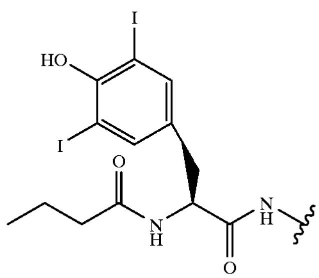  | $5.3 \times 10^{-6}$ | 4.4 |
| 14. | 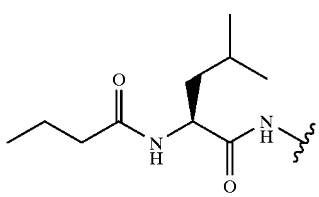  | $2.3 \times 10^{-5}$ | 1.0 |
| 15. | 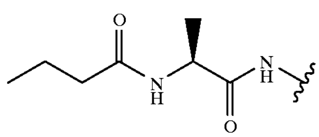  | $4.5 \times 10^{-5}$ | 0.5 |
| 16. | 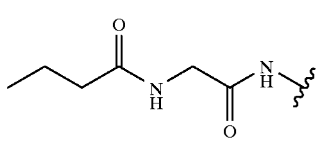  | $1.3 \times 10^{-4}$* | 0.2 |

TABLE 2-continued

EFFECTS OF MODIFICATIONS TO REGION B OF PhTX-343 ON ANTAGONISM OF LOCUST MUSCLE TWITCH CONTRACTION

| Compound No. | | $IC_{50}$ (M) | Relative Potency |
|---|---|---|---|
| 17. | | $2.5 \times 10^{-6}$ | 9.2 |

*SD < 20%

Modifications In Region C (Table 3)

Shortening the butyryl group as in analog 18 resulted in slight but significant reduction in potency. However, increasing the length of the chain from 4 to 7 (compound 19) and then to 10 (compound 20) produced successive increases in potency. Compound 21, which contains two double bonds in a six-carbon moiety was also very potent. The potency of the cyclohexane analogue 22 was equal to that of compound 19, whereas the phenyl analog 23 was equipotent with the $C_{10}$ analog 20. These results indicate the importance of hydrophobicity in this region, the weak potency of compound 22 being attributable to the steric bulk of its cyclohexane moiety.

The phenyl acetyl derivative 24, which differs from compound 23 by the presence of a methylene group located between the phenyl and carbonyl carbon, was less potent than PhTX-343. However, insertion of a double bond between the aromatic ring and the carbonyl moiety (compound 25) led to a greatly increased potency. Substitution of an azido moiety on the aromatic ring (compound 26), which nominally produces a photosensitive affinity label, produced reasonably active compounds compared with PhTX-343, whereas the diazo analog 27 was only weakly active. The potencies of the two dinitrophenyl analogs (compounds 28 and 29) were similar to PhTX-343. Introduction of hydrophilic groups in region C reduces activity. However, introduction of a hydrophobic spacer, as in compound 29, compensates for this change. The 2,4-dinitrophenol moieties in compounds 28 and 29 were introduced in order to produce molecules for use in the preparation of IgG affinity columns. Compounds 30 and 31 containing biotin moieties were prepared as possible candidates for use in avidin affinity chromatography. However, the low solubility of these four analogs rendered them impracticable in this respect.

TABLE 3

MODIFICATIONS TO REGION C OF PhTX-343 ON ANTAGONISM OF
LOCUST MUSCLE TWITCH CONTRACTION

PhTX-343

| Compound No. | | $IC_{50}$ (M) | Relative Potency |
|---|---|---|---|
| 1. | (butyramide) | $2.3 \times 10^{-5}$ | 1.0 |
| 18. | (acetamide) | $5.0 \times 10^{-5}$* | 0.7 |
| 19. | (heptanamide) | $1.0 \times 10^{-5}$ | 2.7 |
| 20. | (decanamide) | $1.4 \times 10^{-6}$ | 16.0 |
| 21. | (hexa-2,4-dienamide) | $1.6 \times 10^{-6}$ | 14.0 |
| 22. | (cyclohexanecarboxamide) | $9.3 \times 10^{-6}$ | 2.5 |
| 23. | (benzamide) | $2.83 \times 10^{-6}$ | 8.2 |
| 24. | (phenylacetamide) | $1.2 \times 10^{-5}$* | 0.5 |

TABLE 3-continued

MODIFICATIONS TO REGION C OF PhTX-343 ON ANTAGONISM OF LOCUST MUSCLE TWITCH CONTRACTION

C

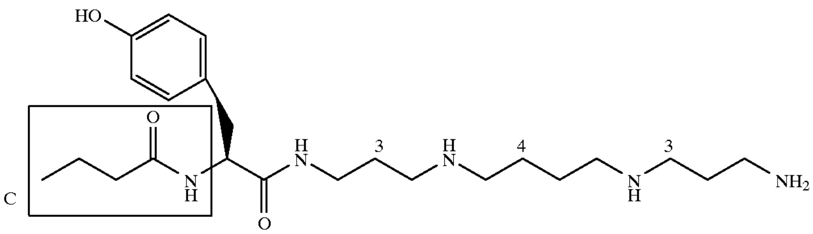

PhTX-343

| Compound No. | | $IC_{50}$ (M) | Relative Potency |
|---|---|---|---|
| 25. | 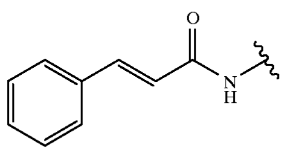  | $2.0 \times 10^{-6}$ | 12.0 |
| 26. | 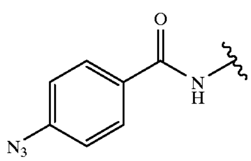  | $4.2 \times 10^{-6}$ | 5.5 |
| 27. | 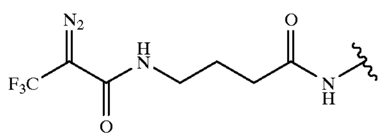  | $2.9 \times 10^{-4}$ | 0.1 |
| 28. | 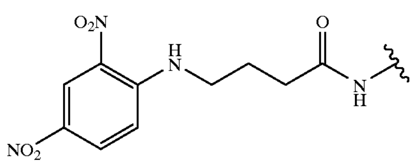  | $5.3 \times 10^{-5}$** | 0.4 |
| 29. | 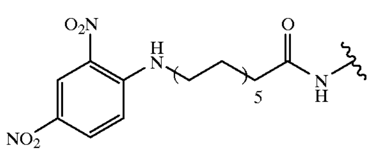  | $1.4 \times 10^{-5}$ | 1.6 |
| 30. | 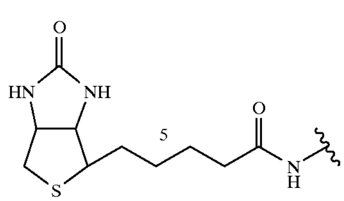  | insoluble | |

TABLE 3-continued

MODIFICATIONS TO REGION C OF PhTX-343 ON ANTAGONISM OF
LOCUST M

TABLE 4-continued

MODIFICATION TO REGION C OF PhTX-343 ON ANTAGONISM OF LOCUST MUSCLE TWITCH CONTRACTIONS

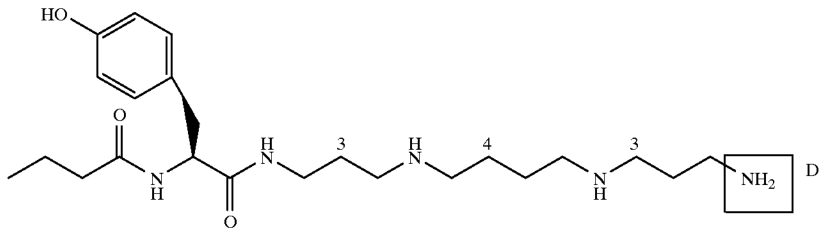

PhTX-343

| Compound No. | | $IC_{50}$ (M) | Relative Potency |
|---|---|---|---|
| 32. | 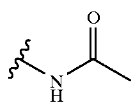  | $3.0 \times 10^{-4}$ | 0.08 |
| 33. | 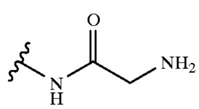  | $1.0 \times 10^{-4}$ | 0.2 |
| 34. | 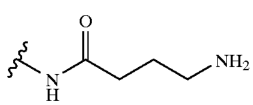  | $6.8 \times 10^{-5}$ | 0.3 |
| 35. | 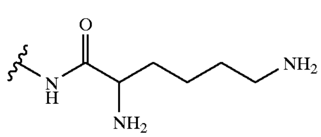  | $1.3 \times 10^{-5}$ | 1.8 |
| 36. | 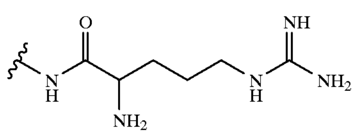  | $6.3 \times 10^{-6}$ | 3.7 |
| 37. | 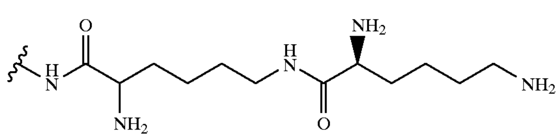  | $1.1 \times 10^{-5}$* | 2.1 |

*SD < 20%

Modifications In More Than One Region (Table 5)

Interesting results were obtained when changes were made in more than one of the regions of PhTX-343. One such compound, diiodo-PhTX-lysine (compound 38) is more potent than PhTX-343 as is diiodo-PhTX-arginine (compound 39). The triplet analog 41, which contains changes in three regions of PhTX-343 was also more potent than the latter. There appears to be synergism between regional modifications, because the combination of diiodo substitution in region B and arginine substitution in region D raises potency much greater than was anticipated from the effects of single substitutions of this type.

TABLE 5

MODIFICATIONS TO MORE THAN ONE REGION OF PhTX-343 ON ANTAGONISM OF LOCUST MUSCLE TWITCH CONTRACTIONS

| Compound No. | | $IC_{50}$ (M) | Relative Potency |
|---|---|---|---|
| 38. | 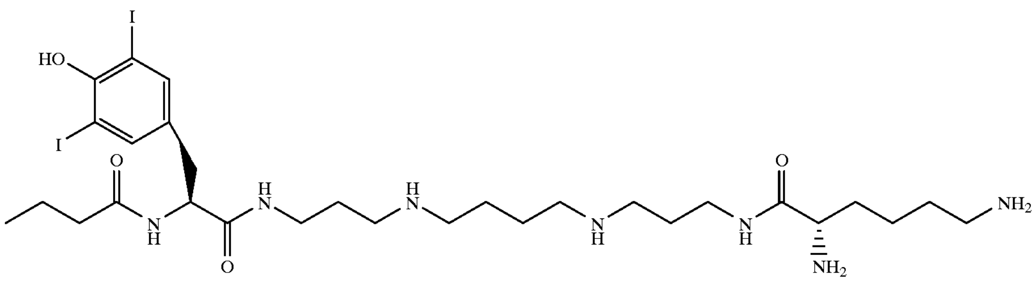  | $1.7 \times 10^{-6}$ | 14 |
| 39. | 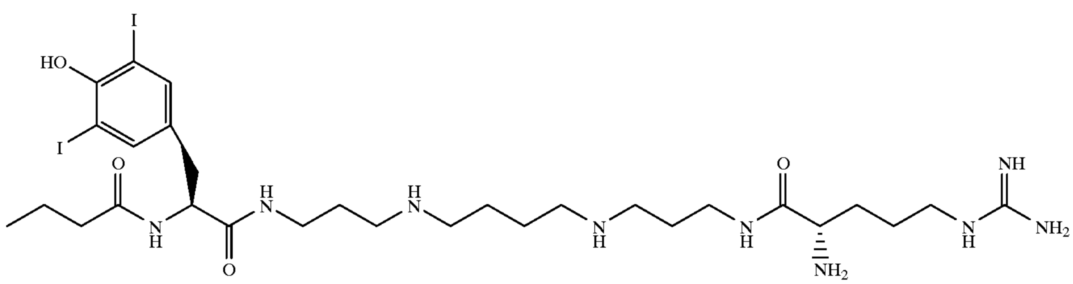  | $0.7 \times 10^{-6}$ | 33 |
| 40. | 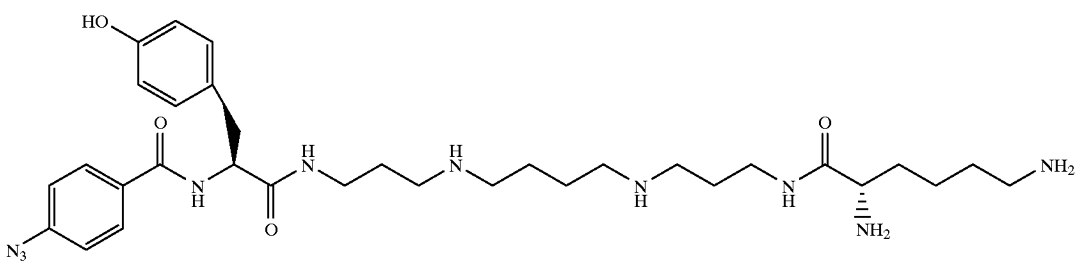  | $3.3 \times 10^{-6}$ | 7 |

TABLE 5-continued

MODIFICATIONS TO MORE THAN ONE REGION OF PhTX-343 ON ANTAGONISM OF LOCUST MUSCLE TWITCH CONTRACTIONS

| Compound No. | | $IC_{50}$ (M) | Relative Potency |
|---|---|---|---|
| 41. | 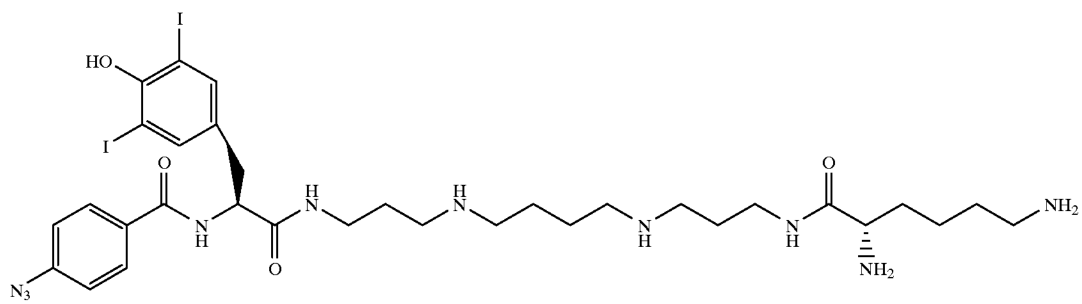  | $1.8 \times 10^{-6}$ | 13 |

Other Modifications (Tables 5 and 7)

The Bis-PhTX analogs surprisingly contained compounds (Table 6) which excited rather than inhibited locust muscle. However, one must exercise some caution in interpreting data obtained from an assay which does not clearly differentiate between a variety of possible pre- and postsynaptic sites of action. Further studies on these molecules, using microelectrode recording techniques will, hopefully, shed further light on their excitatory or "agonist-like" properties.

The mono- and bis-spermine (compounds 47–52) (Table 7) were prepared in order to check whether chain analogs with a hydrophobic end and a polyamine chain would have activity. The low potencies of the mono- and bis-spermine analogs (compounds 48, 49, 50) suggest that geometric constraints and the presence of both hydrophobic and hydrophilic moieties are essential for activity. However, compound 52, bis-$C_{10}$-spermine is as active as PhTX-343. The potency results, ranging from agonistic to weak to moderate antagonism, as yet, cannot be accounted for, but the relatively high potencies of analogs 49 and 52 could result from the additional anchoring (either in a hydrophobic pocket in the QUIS-R or through association with the lipid bilayer) afforded to these molecules by their aliphatic chains, which compensates for the loss of the aromatic moiety.

TABLE 6

BIS ANALOGUES OF PhTX-343: A SINGLE MOLECULE SYMMETRICALLY ACYLATED N-ALKYL-TYROSINE

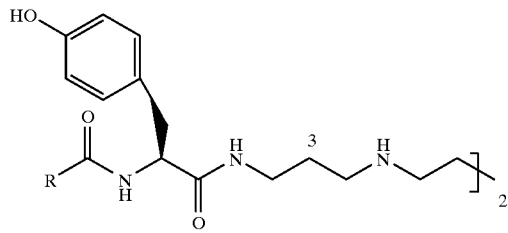

| Compound No. | | IC$_{50}$ (M) | Relative Potency |
|---|---|---|---|
| 42. | 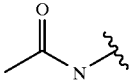 | a-1 | — |
| 43. | 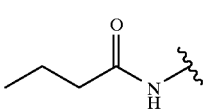 | a-1 | — |
| 44. |  | insol. | — |
| 45. |  | insol. | — |
| 46. | 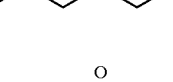 | $1.1 \times 10^{-4}$ | 0.2 |

TABLE 7

POTENCIES OF MONO- AND BIS-SPERMINE ANALOGUES

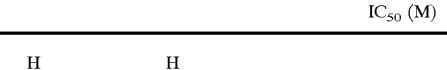

| Compound No. | | IC$_{50}$ (M) | Relative Potency |
|---|---|---|---|
| 47. | 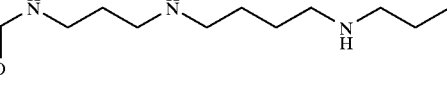 | agonist | — |
| 48. |  | $1.0 \times 10^{-4}$ | 0.2 |
| 49. | 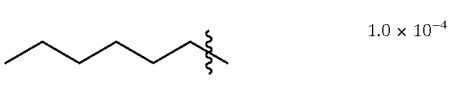 | $1.0 \times 10^{-5}$ | 2.3 |

TABLE 7-continued

POTENCIES OF MONO- AND BIS-SPERMINE ANALOGUES

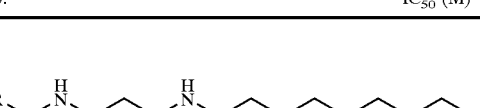

| Compound No. | | IC$_{50}$ (M) | Relative Potency |
|---|---|---|---|
| 50. |  | $2.3 \times 10^{-3}$ | 0.1 |
| 51. |  | agonist | — |
| 52. | | $2.3 \times 10^{-5}$ | 1.0 |

TABLE 8
RELATIVE POTENCIES AT N AND Q RECEPTORS
$IC_{50}$ (relative to PhTX-343)
QUIS-R, muscle contraction: 1.0 [$2.30 \times 10^{-5}$ M]
nAch-R, [$^3$H]H$_{12}$-HTX binding: 1.0 [$2.60 \times 10^{-6}$ M]
| Compound No. | Structure | Name | Relative Potency Q | Relative Potency N | References |
|---|---|---|---|---|---|
| 1. | 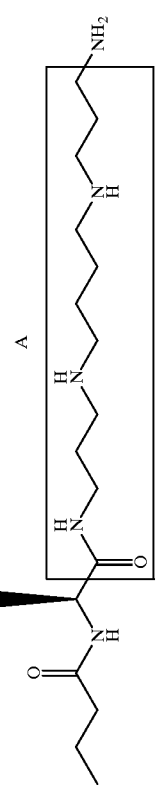 | PhTX-343 | 1.0 | 1.0 | 1, 3, 5, 7, 8, 9 |
| 2. | 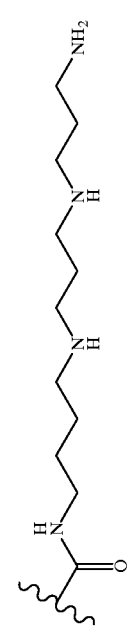 | 433 | 1.3 | 2.4 | 1, 3, 5, 7, 8, 9 |
| 3. | 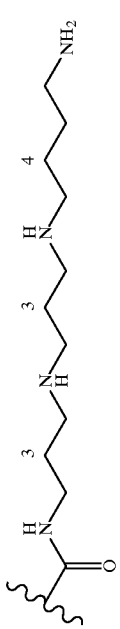 | 334 | 1.5 | | 1, 3, 5, 7, 8 |

TABLE 8-continued

RELATIVE POTENCIES AT N AND Q RECEPTORS

| # | Structure | Label | | | |
|---|---|---|---|---|---|
| 4. | (amide-NH-(CH2)4-NH-(CH2)3-NH2) | | 43 | 0.5 | 2.9 | 1, 3, 5, 8, 9 |
| 5. | (amide-NH-(CH2)4-NH2) | | 4 | 0.01 | 0.05 | 1, 3, 5, 8, 9 |
| 6. | (amide-NH2) | | | 0.05 | 0.0261 | 5, 8, 9 |
| 7. | (amide-NH-(CH2)3-NH-CH(CH3)-CH2-NH-(CH2)3-NH2) | Me-433 | | 0.6 | 5.2 | 1, 5, 8, 9 |
| 8. | (amide-NH-(CH2)3-NH-CH(C4H9)-CH2-NH-(CH2)3-NH2) | Bu-433 | | 5.6 | 18.6 | 1, 3, 5, 7, 8, 9 |
| 9. | (amide-NH-(CH2)3-N+(CH3)2-(CH2)4-N+(CH3)3) | PerMe | | 0.2 | | 1, 3, 5, 8 |

TABLE 8-continued

RELATIVE POTENCIES AT N AND Q RECEPTORS $IC_{50}$ (relative to PhTX-343)
QUIS-R, muscle contraction: 1.0 [$2.30 \times 10^{-5}$ M]
nAch-R, [$^3$H]H$_{12}$-HTX binding: 1.0 [$2.60 \times 10^{-6}$ M]

| Compound No. | | Name | Relative Potency Q | Relative Potency N | References |
|---|---|---|---|---|---|
| 10. | | PhTX | 1.0 | 1.0 | 1, 3, 5, 8, 9 |

TABLE 8-continued

RELATIVE POTENCIES AT N AND Q RECEPTORS

| | | | | |
|---|---|---|---|---|
| 11. | ![structure with Phe] | Phe | 3.4 | 2.8 1, 3, 5, 7, 8, 9 |
| 12. | ![structure with OAc] | OAc | 0.7 | 1, 3, 5, 8 |
| 13. | ![structure with OBn] | OBn | 1.0 | 1, 3 |

TABLE 8-continued
RELATIVE POTENCIES AT N AND Q RECEPTORS
| | | | | |
|---|---|---|---|---|
| 14. |  | I$_2$ | 4.4 | 8.7 1, 3, 4, 5, 8, 9 |
| 15. |  | Leu | 1.0 | 8.7 1, 3, 4, 5, 8, 9 |
| 16. |  | Ala | 0.5 | 4.6 1, 3, 4, 5, 8, 9 |
| 17. |  | Gly | 0.2 | 4.2 1, 3, 4, 5, 8, 9 |

TABLE 8-continued

RELATIVE POTENCIES AT N AND Q RECEPTORS

| | | | | | |
|---|---|---|---|---|---|
| 18. | | Trp | 9.2 | 9.0 | 1, 3, 4, 5, 8, 9 |
| 19. | | Cl₂ | 1.3 | | 3, 4 |
| 20. | | Br₂ | 2.0 | | 3, 4 |

TABLE 8-continued

RELATIVE POTENCIES AT N AND Q RECEPTORS

| 21. | [structure with F, HO on ring, butanoyl amide] | F | 0.6 | 3, 4 |
| 22. | [structure with NO$_2$, HO on ring, butanoyl amide] | NO$_2$ | 1.2 | 3, 4 |
| 23. | [structure with HO on ring, butanoyl amide, hashed wedge] | D | 0.5 | 3, 4 |

TABLE 8-continued
RELATIVE POTENCIES AT N AND Q RECEPTORS
| Compound No. | | | | |
|---|---|---|---|---|
| 24. | 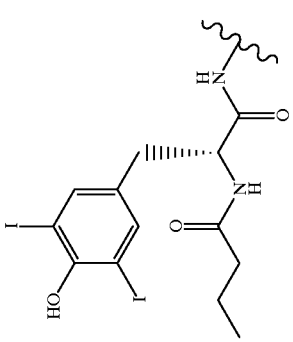 | $I_2$-D | 0.9 | 3, 4 |
IC$_{50}$ (relative to PhTX-343)
QUIS-R, muscle contraction: 1.0 [2.30 × 10$^{-5}$ M]
nAch-R, [$^3$H]H$_{12}$-HTX binding: 1.0 [2.60 × 10$^{-6}$ M]
| | | Name | Relative Potency | | References |
|---|---|---|---|---|---|
| | | | Q | N | |
| 25. | 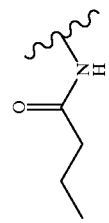 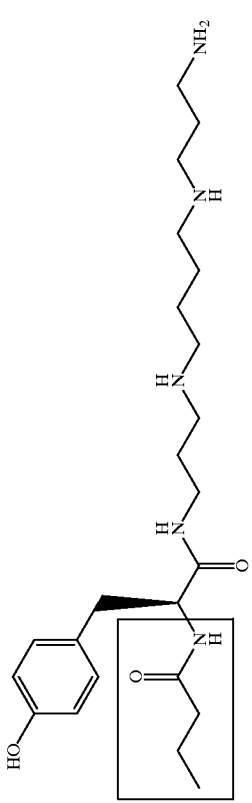 | PhTX | 1.0 | 1.0 | 1, 7, 8, 9 |

TABLE 8-continued

RELATIVE POTENCIES AT N AND Q RECEPTORS

| # | Structure | Group | Value | Refs |
|---|---|---|---|---|
| 26. | acetamide | $C_2$ | 0.7 | 1, 5, 8, 9 |
| 27. | heptanamide | $C_7$ | 2.7 | 6.5 1, 3, 4, 5, 8, 9 |
| 28. | decanamide | $C_{10}$ | 16.0 | 10.4 1, 3, 4, 5, 8, 9 |
| 29. | hexadienamide | Diene | 14.0 | 1, 3, 4, 8, 9 |
| 30. | cyclohexanecarboxamide | CH | 2.5 | 1, 3, 4, 5, 8, 9 |
| 31. | benzamide | Ph | 8.2 | 1, 3, 4, 5, 8, 9 |

TABLE 8-continued
RELATIVE POTENCIES AT N AND Q RECEPTORS
| | | | | |
|---|---|---|---|---|
| 32. | 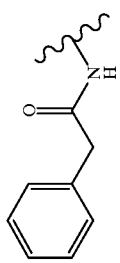 | Bn | 0.5 | 18.4 1, 3, 4, 5, 8, 9 |
| 33. | 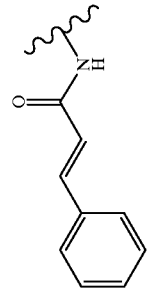 | Cin | 12.0 | 15.3 1, 3, 4, 5, 8, 9 |
| 34. | 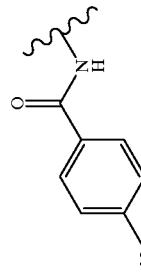 | N₃Ph | 5.5 | 12.4 1, 3, 4, 5, 8, 9 |
| 35. | 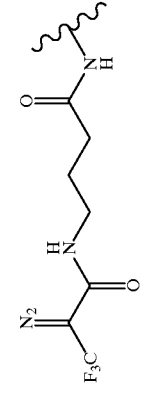 | Diazo | 0.1 | 1, 8 |
| 36. | 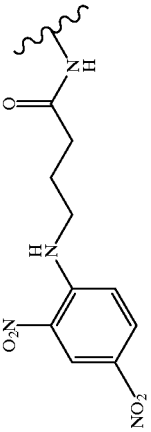 | DNP4 | 0.4 | 5.4 1, 3, 4, 5, 8, 9 |

TABLE 8-continued

RELATIVE POTENCIES AT N AND Q RECEPTORS

| # | Structure | Value | DNP12 | Refs |
|---|---|---|---|---|
| 37. | (2,4-dinitrophenyl-NH-(CH2)5-C(O)NH-) | 1.6 | DNP12 | 5.8 1, 3, 4, 8, 9 |
| 38. | (HOOC-CH(NH2)-CH2-CH2-C(O)NH-) | 0.15 | | 3 |
| 39. | (HOOC-CH2-CH2-CH(COOH)-NH-(CH2)3-C(O)NH-) | <0.1 | | 3 |
| 40. | (biotinyl-NH-CH(CH2CH2COOH)-C(O)NH-) | <0.05 | | 3 |

TABLE 8-continued

RELATIVE POTENCIES AT N AND Q RECEPTORS

| Compound No. | | Name | Relative Potency Q | N | References |
|---|---|---|---|---|---|
| 41. | B-1 | | insoluble | | 1, 5, 8 |
| 42. | B-2 | | insoluble | | 1, 8 |

$IC_{50}$ (relative to PhTX-343)
QUIS-R, muscle contraction: 1.0 [$2.30 \times 10^{-5}$ M]
nAch-R, [$^3$H]H$_{12}$-HTX binding: 1.0 [$2.60 \times 10^{-6}$ M]

TABLE 8-continued

RELATIVE POTENCIES AT N AND Q RECEPTORS

| | | | | | |
|---|---|---|---|---|---|
| 41. | (structure) | PhTX-343 | 1.0 | 1.0 | 1, 7, 8, 9 |
| 42. | (structure) | N-Ac | 0.08 | | 1, 8, 9 |
| 43. | (structure) | Gly | 0.2 | 7.0 | 1, 4, 5, 8, 9 |
| 44. | (structure) | GABA | 0.3 | | 1, 3, 4, 5, 8, 9 |
| 45. | (structure) | Lys | 1.8 | 7.2 | 1, 3, 4, 5, 8, 9 |
| 46. | (structure) | Arg | 3.7 | 14.4 | 1, 3, 4, 5, 8, 9 |

TABLE 8-continued
RELATIVE POTENCIES AT N AND Q RECEPTORS
| Compound No. | | Name | Relative Potency Q | N | References |
|---|---|---|---|---|---|
| 47. | | Lys$_2$ | 2.1 | 9.6 | 1, 3, 4, 5, 8, 9 |
| 48. | | I$_2$-343-Lys | 14 | 8.1 | 1, 5, 8, 9 |
IC$_{50}$ (relative to PhTX-343)
QUIS-R, muscle contraction: 1.0 [2.30 × 10$^{-5}$ M]
nAch-R, [$^3$H]H$_{12}$-HTX binding: 1.0 [2.60 × 10$^{-6}$ M]
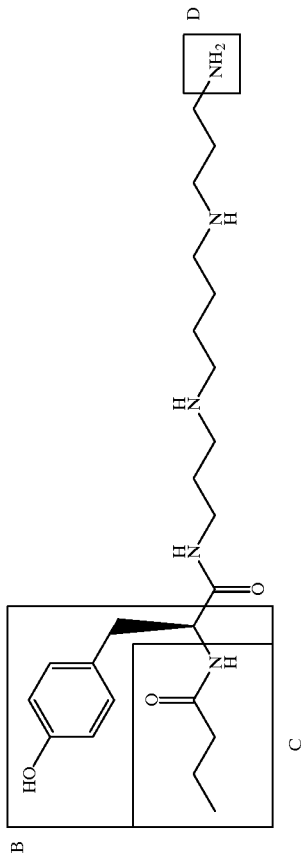

TABLE 8-continued

RELATIVE POTENCIES AT N AND Q RECEPTORS

| # | Structure | Name | | | |
|---|---|---|---|---|---|
| 49. | | $I_2$-343-Arg | 33 | 13.7 | 1, 5, 8, 9 |
| 50. | | $N_3Ph$-343-Lys | 7 | 6.5 | 1, 5, 8, 9 |
| 51. | | $N_3Ph$-$I_2$-343-Lys | 13 | 3.2 | 1, 5, 8, 9 |

TABLE 8-continued

RELATIVE POTENCIES AT N AND Q RECEPTORS

| 52. | [structure] | $N_3Cin-I_2$-343-Arg | 9.0 | 3 |
| 53. | [structure] | $N_3Cin$-343-Arg | 2.8 | 3 |
| 54. | [structure] | $N_3Cin-I_2$-343 | 4 | 3 |

TABLE 8-continued

RELATIVE POTENCIES AT N AND Q RECEPTORS

| | | | | |
|---|---|---|---|---|
| 55. | [structure] | $N_3Cin-I_2$-343 | 10 | 3 |
| 56. | [structure] | $N_3Ph-C_6$-343-Arg | 2.8 | 3 |
| 57. | [structure] | $C_{10}-I_2$-343-Arg | 5.0 | 3 |

TABLE 8-continued

RELATIVE POTENCIES AT N AND Q RECEPTORS

| Compound No. | | Name | Relative Potency Q | References |
|---|---|---|---|---|
| 58. | [structure] | $C_{10}$-Trp-343-Arg | 10.0 | 3 |
| 59. | [structure] BISPRODUCT | $C_2$—$C_2$ | | 5, 9 |

TABLE 8-continued

RELATIVE POTENCIES AT N AND Q RECEPTORS

| | | | |
|---|---|---|---|
| 60. | (structure) | $C_4$—$C_4$ | 0.38 9 |
| 61. | (structure) | $C_7$—$C_7$ | 7.9 9 |

TABLE 8-continued

RELATIVE POTENCIES AT N AND Q RECEPTORS

| 62. | (structure) | $C_{10}-C_{10}$ | 7.2 | 9 |

SPERMINE ANALOGS

| 63. | (structure) | Bis-$C_4$ | 0.1 | 5, 8 |
| 64. | (structure) | Bis-$C_7$ | agonist | 5, 8 |
| 65. | (structure) | Bis-$C_{10}$ | 1.0 | 5, 8 |

TABLE 8-continued

RELATIVE POTENCIES AT N AND Q RECEPTORS

| | | | | |
|---|---|---|---|---|
| 66. | [structure] | $C_4$ | agonist | 5, 8 |
| 67. | [structure] | $C_7$ | 0.27 | 5, 8 |
| 68. | [structure] | $C_{10}$ | 2.3 | 5, 8 |
| 69. | [structure] | ArgTX-533 | 7 | 2 |
| 70. | [structure] | OMe | 8 | 2 |

TABLE 8-continued
RELATIVE POTENCIES AT N AND Q RECEPTORS
| | | N | Q |
|---|---|---|---|
| 71. | 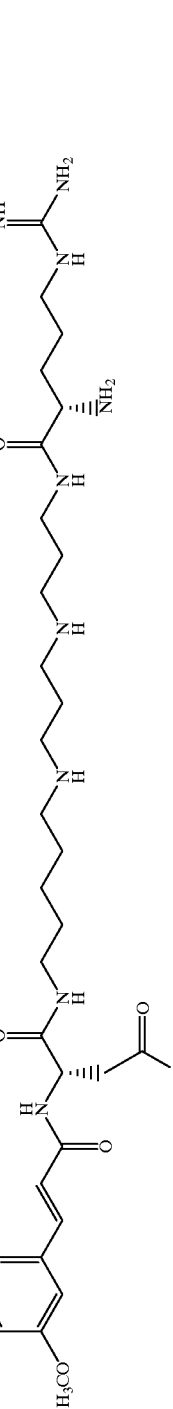 | 15 | 2 |
| 72. | 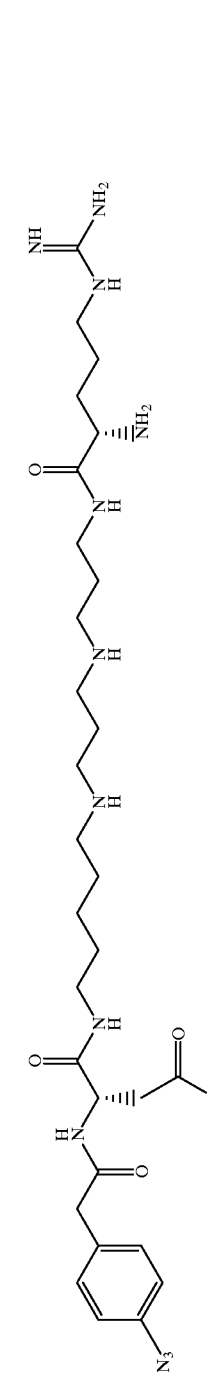 | 6 | 2 |
| 73. | 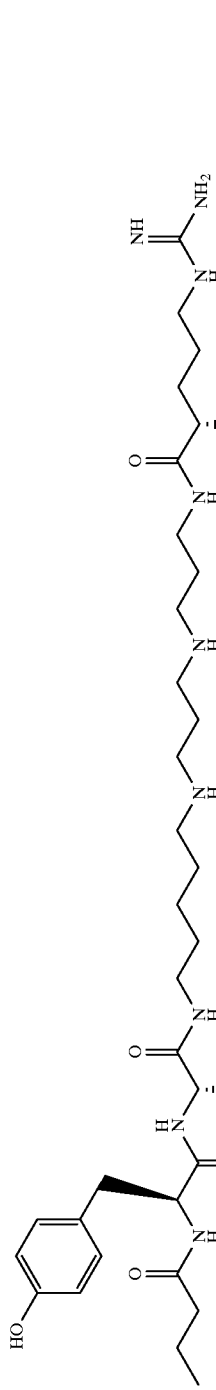 | 6 | 2 |

TABLE 8-continued
RELATIVE POTENCIES AT N AND Q RECEPTORS
| | | | |
|---|---|---|---|
| 74. | 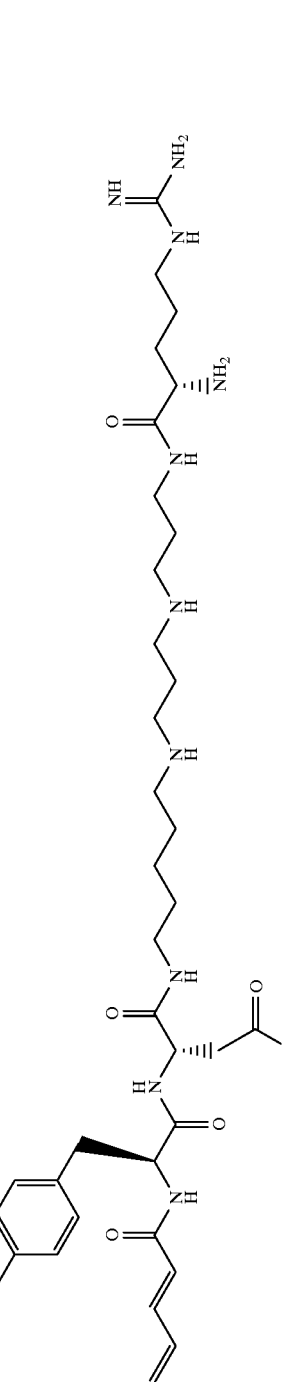 | 8 | 2 |
| 75. | 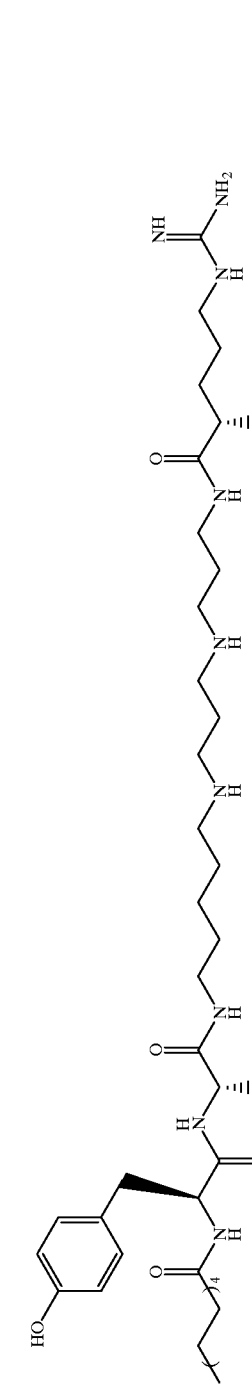 | 16 | 2 |

TABLE 8-continued

RELATIVE POTENCIES AT N AND Q RECEPTORS

| Compound No. | | Relative Potency Q |
|---|---|---|
| 76. | (structure) | 0.2  2 |

UNPUBLISHED DATA

| Compound No. | Name | Relative Potency Q |
|---|---|---|
| 77. | $C_{10}$-Arg | 5.0 |

TABLE 8-continued

RELATIVE POTENCIES AT N AND Q RECEPTORS

| | Structure | Label | Potency |
|---|---|---|---|
| 78. | (3,5-diiodo-Tyr derivative with C$_9$H$_{19}$ acyl, propyl-NH-butyl-NH$_2$ chain) | C$_{10}$-I$_2$ | 7.0 |
| 79. | (Trp derivative with C$_9$H$_{19}$ acyl, propyl-NH-butyl-NH$_2$ chain) | C$_{10}$-Trp | 8.0 |
| 80. | (4-fluoro-Phe derivative with butyryl, propyl-NH-butyl-NH$_2$ chain) | | 1 |

TABLE 8-continued
RELATIVE POTENCIES AT N AND Q RECEPTORS
| | | |
|---|---|---|
| 81. 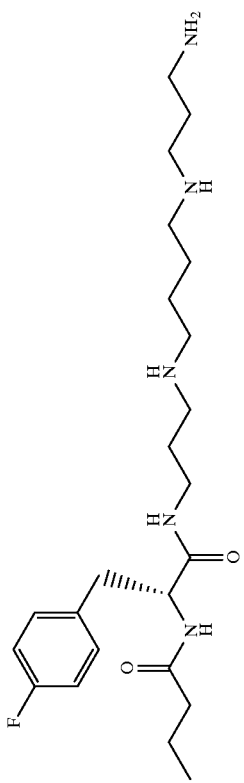 | 82. 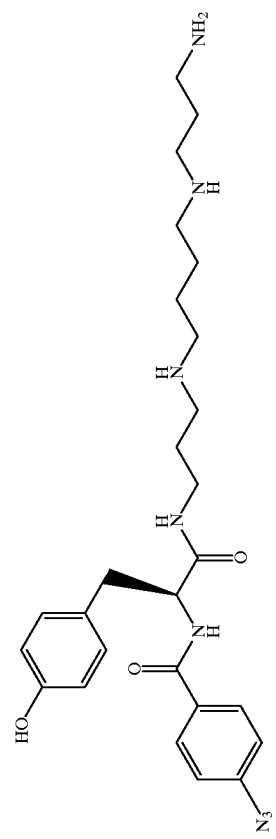 | 83. 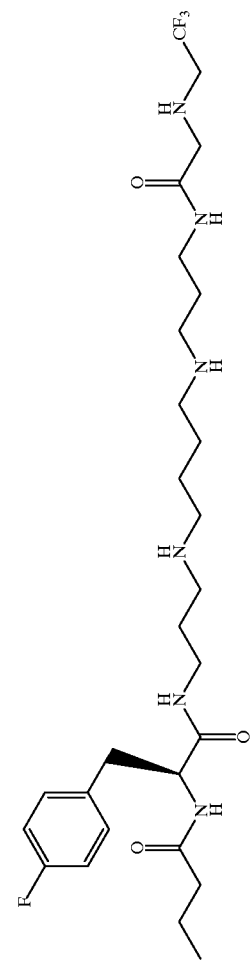 |

TABLE 8-continued

RELATIVE POTENCIES AT N AND Q RECEPTORS

| # | Structure | Value |
|---|---|---|
| 84. | (structure) | 0.6 |
| 85. | (structure) | |
| 86. | (structure) | 0.4 |

TABLE 8-continued

RELATIVE POTENCIES AT N AND Q RECEPTORS

| 87. | $C_{10}$-343-$N_3$Cin | 0.55 |
| 88. | | 1.5 |
| 89. | | |
| 90. | | |

TABLE 8-continued

RELATIVE POTENCIES AT N AND Q RECEPTORS

| | | |
|---|---|---|
| 91. | (structure) | >1–2 |
| 92. | (structure) | 15 |
| 93. | (structure) | |

TABLE 8-continued

RELATIVE POTENCIES AT N AND Q RECEPTORS

| # | Structure | Label | Value |
|---|---|---|---|
| 94. | (structure) | | 1 |
| 95. | (structure) | Diene-N₃Ph-343 | 2 |
| 96. | (structure) | C₁₀-N₃Ph-343 | |

TABLE 8-continued
RELATIVE POTENCIES AT N AND Q RECEPTORS
| | | |
|---|---|---|
| 97. | 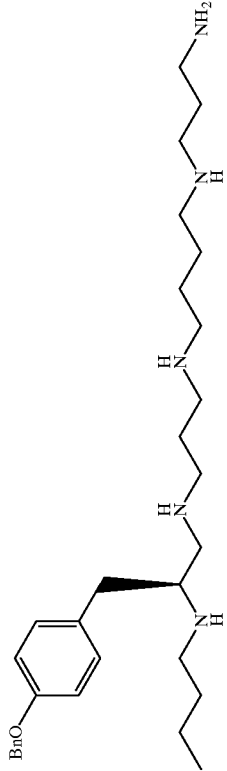 | 5.0 |
| 98. | 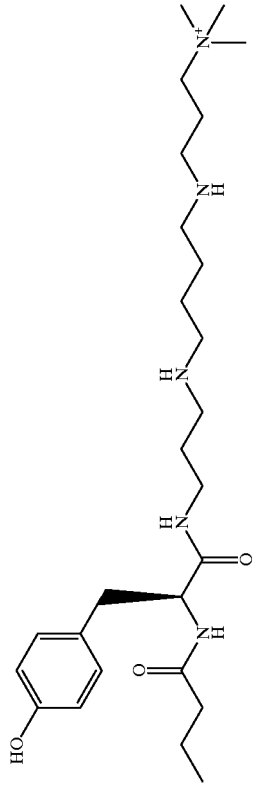 | 0.7 |
| 99. | 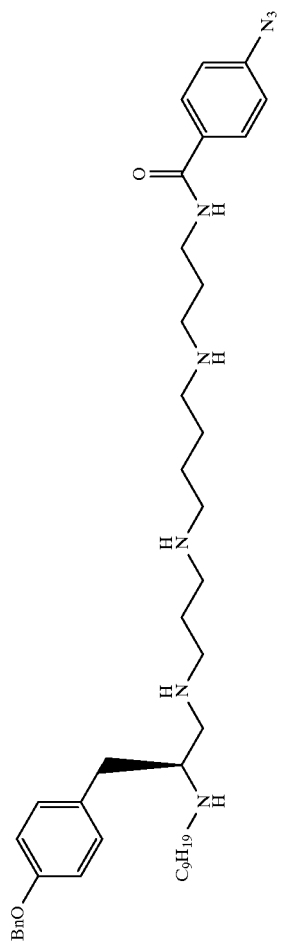 | |

TABLE 8-continued

RELATIVE POTENCIES AT N AND Q RECEPTORS

| | | |
|---|---|---|
| 100. | (structure) | |
| 101. | (structure) | 0.5 |
| 102. | (structure) | 0.5 |

TABLE 8-continued
RELATIVE POTENCIES AT N AND Q RECEPTORS
| 103. | 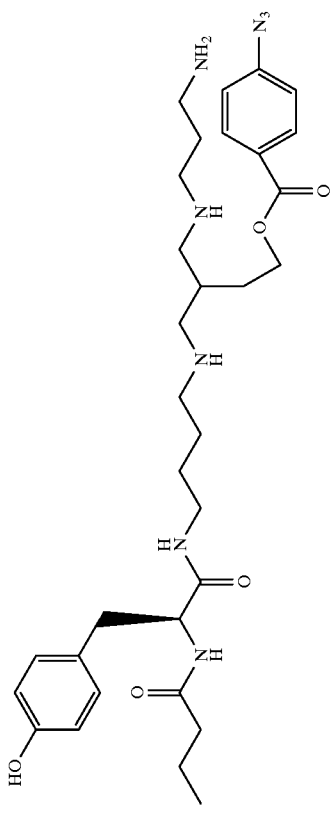 | 0.1 |
| 104. | 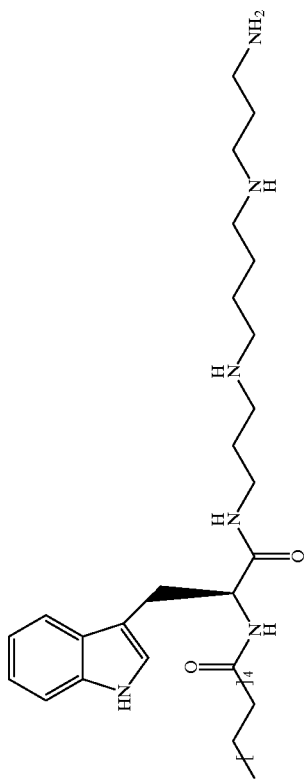 | 8.0 C10-Trp |

TABLE 8 RELATIVE POTENCIES AT N AND Q RECEPTORS

REFERENCES:

1. M. Bruce, B. Bukownik, A. T. Eldefrawi, R. Goodnow, Toxicon Vol. 28, No. 11, pp 1333–1346, 1990
2. Seok-Ki Chio, Koji Nakanishi, Tetrahedron Vol. 49, No. 26, pp 5777–5790, 1993
3. I. R. Duce, Neurotox '91
4. Koji Nakanishi, Robert Goodnow, Alfred Benzon Symposium 33, p 139–149
5. R. Goodnow, K. Konno, M. Niwa, K. Nakanishi, Tetrahedron, Vol. 46, pp 3267–3286, 1990
6. A. Kalivretanos, K. Nakanishi, J.O.C. Vol. 58, pp 6596–6608, 1993
7. A. Eldefrawi, M. Eldefrawi, K. Nakanishi, P. Usherwood, Proc. Natl. Acad. Sci. USA, Vol. 85, pp 4910–4913, 1988
8. K. Nakanishi, R. Goodnow, K. Konno, M. Niwa, P. Usherwood, A. Eldefrwai, M. Eldefrawi, Pure & Appl. Chem. Vol. 62, pp 1223–1230, 1990
9. N. Anis, S. Sherby, R. Goodnow, K. Nakanishi, P. Usherwood, A. Eldefrawi, M. Eldefrawi, J. Pharmacol. EXP. Ther. Vol. 254, pp 764–772, 1990.

Discussion

In assessing the results of these studies it is important to bear in mind the limitations of the assay that was employed. Some of these problems have been alluded to under Materials and Methods. Although care was taken to show that all of the compounds identified as antagonists inhibited the muscle response to L-glutamate as well as that resulting from motor nerve stimulation, it would not be correct to assume that PhTX-343 and its analogues are simply non-competitive antagonists of the postsynaptic receptors present at excitatory synapses on locust retractor unguis muscle. Reduction of twitch contraction amplitude by most of the analogues was enhanced when the nerve stimulation frequency was increased. This suggests that inhibition is use-dependent and lends support to the view that they are non-competitive antagonists of QUIS-R. However, the assay does not unequivocally differentiate between presynaptic and postsynaptic sites of action, both of which could, in principle, be influenced by stimulation frequency. Some of the compounds, particularly those in which the aromatic end of PhTX was made more hydrophobic, initially potentiated the neurally-evoked twitch contraction. This could have arisen from enhancement of transmitter release or block of transmitter uptake (34), but it is equally possible that the toxins interact with a site or sites distinct from those involved in their antagonism of QUIS-R (38).

This structure-activity study has produced several molecules which are more potent non-competitive antagonists of locust muscle QUIS-R than the natural philanthotoxin, PhTX-433. Hydrophobicity of the aromatic moiety is an important potency determinant and this is also true for the butyryl side chain, although in the latter case there is clear evidence that steric factors are also significant. Perhaps the role of these groups is to anchor the toxin in a hydrophobic pocket of the receptor channel to support the binding of the polyamine moiety to the channel wall (36). The increased potency seen in compound 8 is less easily reconciled with this model, although one might anticipate, perhaps, the presence of additional pockets of hydrophobicity in the region of the channel to which the polyamine moiety binds. If one were to seek a generalization from the results of these studies it would be the identification of a molecule which embraces the structures of the four moieties which produced the most potent ligands. This molecule, decanoyl-tryptophan-butylspermine-arginine is currently being synthesized.

PhTX-343 binds to the QUIS-R channel, possible at a site located within its selectivity filter (35,36). Other studies in our laboratories have shown that antagonism of locust muscle QUIS-R by PhTX-343 and compound 13, the diiodo analogue, is voltage-dependent, as one might expect for open channel blockers carrying a net positive charge. Interestingly, at high membrane potentials (above about −100 mV) the block is relieved, presumably as the toxin is dissociated from its binding site in the channel. Ashford, et al. (39) demonstrated a similar phenomenon when studying non-competitive antagonism of locust muscle QUIS-R by chlorisondamine, and Magazanik, et al. (40) have recently shown that high membrane potentials relieve channel block of insect muscle QUIS-R caused by the polyamine amide spider toxin, argiotoxin-636. Cation-selective membrane channels are generally envisaged as aqueous pores lined by fixed negative charges. In the case of the amphibian nicotinic acetylcholine receptor the latter are thought to be concentrated in three clusters in the vicinity of the selectively filter (41). Although we do not yet have equivalent information on the QUIS-R channel, there is clear evidence from our studies that an increase in the number of protonated groups on the PhTX molecule is accompanied by increased potency. If PhTX blocks the QUIS-R channel by binding to the channel wall, then it seems likely that this results from interaction between the protonated groups in the toxin molecule and fixed negative charges on the wall of the channel. The relative disposition and number of protonated groups on the toxin seems to be important in determining potency, which appears to be maximized for a given number of protonated groups when these have a constant spacing of three methylenes on their equivalents.

It may be unwise to conclude from these and other data on the polyamine amide toxins that they interact exclusively with cation-selective channels of specific transmitter receptors (6,8,35). The polyamine, spermine, which is also a non-competitive antagonist of locust muscle QUIS-R (33), is known to stabilize membranes by cross-linking phospholipids (42). PhTX-343 and analogs might also bind to acidic phospholipids it membranes of excitable cells, thereby reducing membrane fluidity. The increased potency seen with increasing hydrophobicity of the PhTX-343 analogues could arise through the closer association of toxin molecule with the cell membrane lipid. The number and disposition of positive charges on the toxin relative to those on the membrane phospholipids would also play a role in determining the affinity of the toxin. In fact, the presence of negatively charged groups on the outer face of membrane proteins could, in principle, enable these compounds to bridge across the lipid-protein interface. If membrane stabilization reduces the capacity of receptor molecules to undergo the conformational changes required for channel gating, then one could envisage non-competitive antagonism of QUIS-R arising through relatively non-specific binding of PhTX-343 to membrane phospholipids, but it is difficult to understand how this model could account for the open channel block and the striking voltage dependencies associated with PhTX-343 antagonism.

REFERENCES

1. Cotman, C. W. and Iversen, L. L., *Trends Neurosci.* 1987; 10:263–265.
2. Robinson, M. B. and Coyle, J. T., *FASEB J.* 1987; 1:446–455.

3. Silverstein, F. S., Torke, L., Barks, J. and Johnston, M. V., *Developmental Brain Res.* 1987; 34:33–39.
4. Young, A. B., et al., *Science* 1988; 241:981–983.
5. Greenamyre, J. T., et al., *Science* 1985; 227:1496–1499.
6. Usherwood, P. N. R. (1987a) In: "Site of Action for Neurotoxin Pesticides," pp. 298–314 (Hollingworth, R. M. and Green, M. B., Eds.) Washington, DC: American Chemical Society.
7. Wong, E. H. F., Kemp, J. A., Priestley, T., Knight, A. R., Woodruff, G. N. and Iversen, L. L., *Proc. Natl. Acad. Sci. USA*, 1986; 83:7104–7108.
8. Usherwood, P. N. R. (1987b) In: "Neurotoxins and their Pharmacological Implications, pp. 131–151 (Jenner, P., Ed.) New York: Raven Press.
9. Watkins, J. C. and Evans, R. H., *Ann. Rev. Pharmac. Toxicol.* 1981; 21:165–204.
10. Kemp, J. A., Foster, A. C. and Olverman, H. J., *Trend Neurosci.* 1987; 10:265–272.
11. Usherwood, P. N. R., *Adv. Comp. Physiol. Biochem.* 1978; 7:222–309.
12. Kawai, A., Miwa, T. and Abe, T., *Brain Res.* 1982; 247:169–171.
13. Boden, P., Duce, I. R. and Usherwood, P. N. R., *J. Britt. Pharmac.* 1984; 83:221P.
14. Bateman, A., Boden, P., Dell, A., Duce, I. R., Quicke, D. L. J. and Usherwood, P. N. R., *Brain Res.* 1985; 339:237–244.
15. Grishin, L. G., Voldova, T. M., Arsoniev, A., Reshetova, A. S. Onorprienko, V. V. Magazanic, L. G., Antonov, S. M. and Fedorova, I. M., *Bioorg. Khim.* 1986; 12:1121–1124.
16. Piek, T., Mantel, P. and Engels, E., *Comp. Gen. Pharmacol.* 1971; 2:317–331.
17. Piek, T. and Njio, K. D., *Toxicon.* 1975; 13:199–201.
18. Piek, T., Mantel, P. and Jas, H., *J. Insect Physiol.* 1980; 26:345–349.
19. Clark, R. B., Donaldson, P. L., Gration K. A. F., Lambert, J. J., Piek, T., Ramsey, R. L., Spanjer, W. and Usherwood, P. N. R., *Brain Res.* 1982; 171:360–364.
20. Gration, K. A. F., Clark, R. B. and Usherwood, P. N. E., *Brain Res.* 1979; 171:360–364.
21. Usherwood, P. N. R. and Machili, P., *J. EXP. Biol.* 1968; 49:341–361.
22. Ohshima, T., *J. Biol. Chem.* 1979; 254:8720–8722.
23. Humora, M. and Quick, J. *Org. Chem.* 1970; 44:1166–1168.
24. Hashimoto, Y., Skudo, K., Aramaki, Y., Kawai, N. and Nakajima, T., *Tetrahedron Lett.* 1987; 28:3511–3514.
25. Adams, M. E., Candy, R. L., Enderlin, F. E., Fu, T. E., Jarema, M. A., Li, J. P., Miller, C. A., Schooley, D. A., Shapiro, M. J. and Venema, V. J., *Biochem. Biophys. Res. Comm.* 1987; 348:678–683.
26. Foster and Wong, *Brit. J. Pharmacol.* 1987; 91: 403.
27. Jackson, H. and Usherwood, P. N. R., *Trends Neurosci.* 1988; 11:278=283.
28. Grishink, E. V., et al., *Bioorg. Khim.* 1986; 12:1121–1124.
29. Aramaki, Y., et al., *Proc. Japan Acad., Ser. B.* 1986; 62:359–362.
30. Usherwood, P. N. R., *Am. Zool.* 1967; 7:553–582.
31. Eldefrawi, A., et al., *Prod. Natl. Acad. Sci. U.S.A.* 1988; 85: 4910–4913.
32. Walther, C., *J. Exp. Biol.* 1980; 87:99–119.
33. Robinson, N. L., In: "Insect Neurobiology and Pesticide Action," (*Neurotox.*, 79) pp. 237–239, London: Society of Chemical Industry.
34. Piek, T., et al., In: Neurotox '88: Molecular Basis of Drug and Pesticide Action, pp. 61–76 (Lunt, G. G., Ed.) Amsterdam: Elsevier (1988).
35. Usherwood, P. N. R. and Blagborough, I. S., In: "Progress and Prospects in Insect Control," pp. 45–58 (McFarlane, N. R., Ed.) British Crop Protection Monograph No. 43, British Crop Protection Council (1989).
36. Usherwood, P. N. R. and Blagborough, I. S., In: "Insecticide Action: From Molecule to Organism, pp. 13–41 (Narahashi, T. and Chambers, J. E., Ed.) New York: Plenum Press (1990).
37. Usherwood, P. N. R., et al., *J. Physiol. Paris* 1984; 87:99–119.
38. Brackley, P., et al., *Neurosci. Lettrs.* 1990; 114:51.
39. Ashford, M. L., et al., *J. Exp. Biol.* 1988; 134:131–154.
40. Magazanik, L. G., et al., *Biol. Membran.* 1986; 3:1204–1219.
41. Imoto, K. et al., *Nature* 1988; 335:645–648.
42. Ballas, S. K., et al., *Proc. Natl. Acad. Sci. U.S.A.* 1983: 80:1942–1946.

What is claimed is:
1. A compound having the structure:

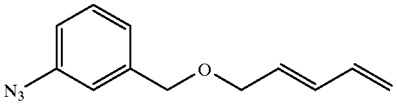

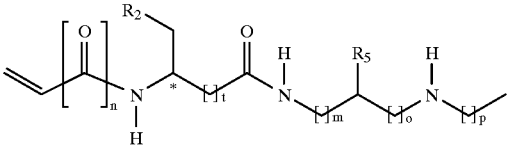

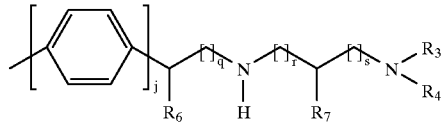

wherein $R_2$ is a 2-indolyl, 3-indolyl, 4-indolyl, 5-indolyl, 4-hydroxyphenyl, 4-(arylalkyloxy)phenyl, 3,4-dihalophenyl, 4-hydroxy-3,5-dihalophenyl, 4-azidophenyl or 4-halophenyl group; wherein $R_3$ is H, a linear or branched chain alkyl or alkenyl group, or a phenyl, 2-azidophenyl, 3-azidophenyl, 4-azidophenyl group, or a 4-azidobenzoyl group, or an alkenylacyl, N-[N-(N-{4-azidobenzoyl} aminopropyl)aminopropyl], cis- or trans-cinnamyl, 2-amino-2-[(4'-azidophenyl)acetyl], N-(2,2,2-trifluoroethyl)-glycyl or D- or L-arginyl or lysyl group bonded through the α-carbonyl moiety thereof; $R_4$ is H, or a linear or branched chain alkyl group; wherein, $R_5$, $R_6$, $R_7$ are independently the same or different and are H, a linear or branched chain alkyl group, an aryl group or an arylalky group; wherein n is 1, j and t are each 0; wherein m, o, q, r and s are 1; wherein p is 2; wherein * denotes a D or L configuration.

2. A compound having the structure:
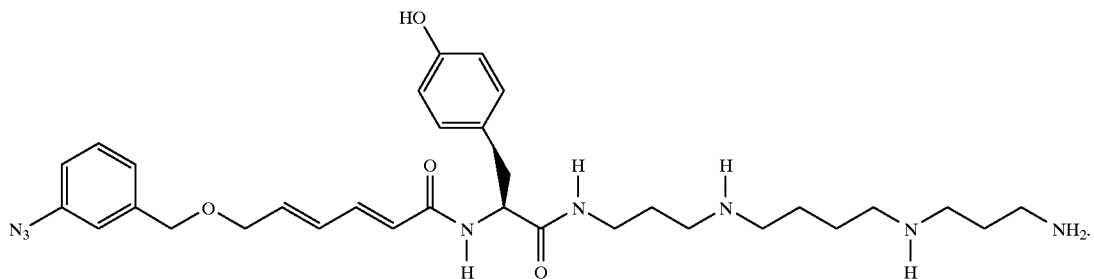
3. A compound having the structure:
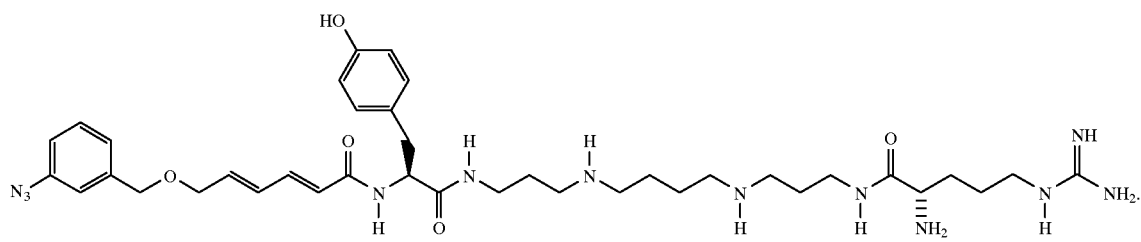
4. A compound having the structure:
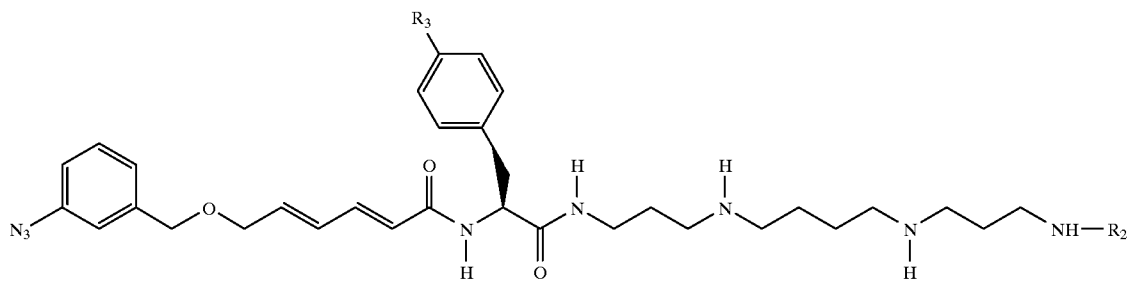
wherein $R_2$ is selected from the group:
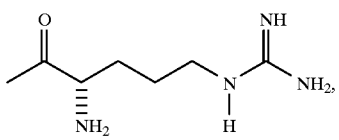
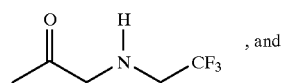, and
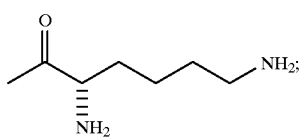
and wherein $R_3$ is selected from the group of F, OH and $N_3$.
5. The compound of claim 4 wherein $R_2$ is
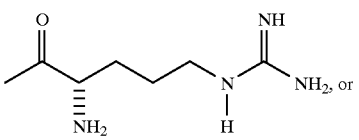, or
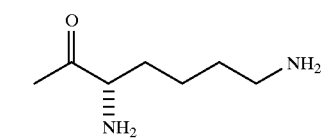
wherein $R_3$ is OH.

6. The compound of claim 5, wherein $R_2$ is

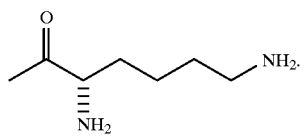

7. A compound having the structure:

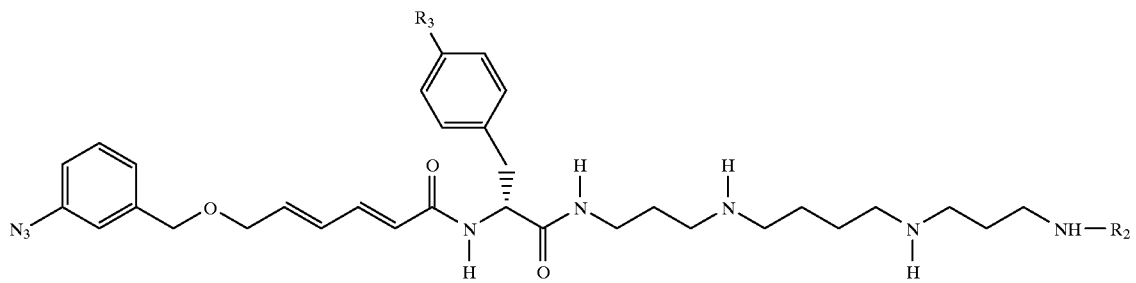

wherein $R_2$ is selected from the group consisting of H, $H_2$+,

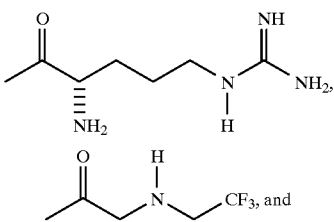

-continued

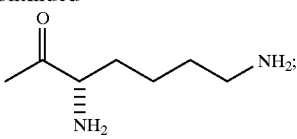

and wherein $R_3$ is selected from the group of F, OH and $N_3$.

8. An insecticidal composition which comprises an effective amount of the compound of claim 1 and a suitable carrier.

9. A pharmaceutical composition which comprises an effective amount of the compound of claim 1 and a pharmaceutically acceptable carrier.

* * * * *